US009850275B2

(12) United States Patent
Nielsen et al.

(10) Patent No.: US 9,850,275 B2
(45) Date of Patent: Dec. 26, 2017

(54) PHOTOLABILE LINKER FOR THE SOLID-PHASE SYNTHESIS OF HYDRAZIDES AND PYRANOPYRAZOLES

(71) Applicant: DANMARKS TEKNISKE UNIVERSITET, Kgs. Lyngby (DK)

(72) Inventors: Thomas E. Nielsen, Charlottenlund (DK); Katrine Qvortrup, Malmö (SE)

(73) Assignee: DANMARKS TEKNISKE UNIVERSITET, KGS. Lyngby (DK)

( * ) Notice: Subject to any disclaimer, the term of this patent is extended or adjusted under 35 U.S.C. 154(b) by 0 days.

(21) Appl. No.: 14/916,547

(22) PCT Filed: Sep. 11, 2014

(86) PCT No.: PCT/EP2014/069392
§ 371 (c)(1),
(2) Date: Mar. 3, 2016

(87) PCT Pub. No.: WO2015/036481
PCT Pub. Date: Mar. 19, 2015

(65) Prior Publication Data
US 2016/0272672 A1 Sep. 22, 2016

(30) Foreign Application Priority Data

Sep. 11, 2013 (EP) .................................... 13183944
Feb. 13, 2014 (EP) .................................... 14155016

(51) Int. Cl.
| | | |
|---|---|---|
| C07K 1/12 | (2006.01) | |
| C07D 233/64 | (2006.01) | |
| C07C 243/18 | (2006.01) | |
| C07C 281/02 | (2006.01) | |
| C07K 1/04 | (2006.01) | |
| C07D 491/052 | (2006.01) | |
| C07K 5/065 | (2006.01) | |
| C07K 5/083 | (2006.01) | |
| C07K 5/087 | (2006.01) | |
| C07K 5/097 | (2006.01) | |
| C07K 7/06 | (2006.01) | |

(52) U.S. Cl.
CPC ............ *C07K 1/124* (2013.01); *C07C 243/18* (2013.01); *C07C 281/02* (2013.01); *C07D 233/64* (2013.01); *C07D 491/052* (2013.01); *C07K 1/042* (2013.01); *C07K 5/06078* (2013.01); *C07K 5/0806* (2013.01); *C07K 5/0808* (2013.01); *C07K 5/0812* (2013.01); *C07K 5/0823* (2013.01); *C07K 7/06* (2013.01); *C07B 2200/11* (2013.01); *Y02P 20/55* (2015.11)

(58) Field of Classification Search
CPC ...... C07K 1/124; C07D 233/64; C07C 243/18
See application file for complete search history.

(56) References Cited

U.S. PATENT DOCUMENTS

2013/0005611 A1   1/2013 Fang et al.

FOREIGN PATENT DOCUMENTS

| EP | 1200484 | 10/2011 |
|---|---|---|
| WO | WO 96/00148 | 1/1996 |
| WO | WO 2004/105685 | 12/2004 |
| WO | WO 2011/127933 | 10/2011 |

OTHER PUBLICATIONS

Bycroft et al; "A novel lysine-protecting procedure for continuous flow solid phase synthesis of branched peptides". J. Chem. Soc., Chem. Commun., Jan. 1, 1993.
Camino, Louis A.: "Synthesis and oxidation of 2-amino-2,3-dihydro-1H-benz[de]isoquinoline and 1,2,3,4-tetra-hydronaphtho [1,8-de] [1,2]diazepine and related cyclic 1,2-dibenzylhydrazines". Contribution from the Department of Chemistry, University of Massachusetts, Amherst, Mass, Jan. 24, 1963.
Chang et al; "Fully automated solid phase synthesis of protected peptide hydrazides on rycycling hydroxymethyl resin". J. Org. Chem., vol. 41, No. 20, 1976, Mar. 15, 1976, pp. 3255-3258.
Fang et al; "Protein chemical synthesis by ligation of peptide hydrazides". Angew. Chem. Int. Ed. 2011, 50, Jun. 6, 2011, pp. 7645-7649.
Nelson et al; "A new amino protecting group removable byu reduction. Chemistry of the dithiasuccinoyl (Dts) function". Experimental Chemistry Research, The Upjohn Company Kalamazoo, Michigan 49001, Jul. 11, 1977, pp. 7363-7365.
Ondetti et al; "Side reactions in the synthesis of peptides containing the aspartylglycyl sequence". Biochemistry, vol. 7, No. 11, Nov. 1968.
Perlow et al; "Use of N-Fmoc amino acid chlorides and activated 2-(Fluorenylmethoxy)-5(4H)-oxazolones in solid-phase peptide synthesis. Efficient syntheses of highly N-Alkylated cyclic hexapeptide oxytocin antagonists related to L-365,209". J. Org. Chem. 1992, 57, Apr. 13, 1992, pp. 4394-4400.
Qvortrup et al; "A photolabile linker for the solid-phase synthesis of 4-substituted NH-1,2,3-triazoles". Chem. Commun., 2011, 47, Jan. 5, 2011, pp. 3278-3280.

(Continued)

Primary Examiner — Joseph R Kosack
(74) Attorney, Agent, or Firm — Michael Best & Friedrich LLP

(57) ABSTRACT

The photolabile hydrazine linker of the present invention is based on the o-nitro-veratryl group, which is capable of releasing hydrazide derivatives upon UV irradiation. The linker allows for a new solid-phase peptide synthesis (SPPS) strategy which is fully orthogonal to the most commonly used protecting groups and chemical methods in SPPS and shows excellent compatibility with peptide composition, notably the 20 naturally occurring α-amino acid residues (even in their side-chain protected form) are accepted in the C-terminal of the peptide hydrazides. Furthermore, the linker unit can be applied to synthesize combinatorial libraries of biological interesting heterocyclic compounds, such as pyranopyrazoles.

18 Claims, 18 Drawing Sheets

(56) References Cited

OTHER PUBLICATIONS

Sharanin et al; "Cyclization reactions of nitriles. VII.* Synthesis of 6-amino-4-aryl-3-methyl-5-cyano-1H,4H-pyrazolo[3,4-b]pyrans". Plenum Publishing Coproration—022-3271/83/1912-2291$07.50, Dec. 1983, pp. 2291-2296.
Stavropoulos et al; "Preparation of polymer-bound trityl-hydrazines and their application in the solid phase synthesis of partially protected peptide hydrazides". Letters in Peptide Science, 2 (1995), ESCOM, Oct. 26, 1995, pp. 315-318.
Wang, Su-Sun; "Solid-phase synthesis of protected peptide hydrazides. Preparation and application of hydroxymethyl resind and 3-(p-Benzyloxyphenyl)-1,1-dimethylpropylovcarbonylhydrazide resin". J. Org. Chem., vol. 40, No. 9, 1975, pp. 1235-1239.
Wang, Su-Sun; "Solid phase synthesis of protected peptides via photolytic cleavage of the x-methylphenacyl ester anchoring linkage". J. Org. Chem., vol. 41, No. 20, 1976, pp. 3258-3261.
Wang et al; "Preparation of a t-Alkyloxycarbonylhydrazide resin and its application to solid phase peptide synthesis". Journal of the American Chemical Society, 91:23, Nov. 5, 1969, pp. 6488-6491.
Yuasa et al; "Facile synthesis of B-keto esters from methyl acetoacetate and acid chloride: The barium oxide/methanol system". Organic Process Research & Development, Sep. 3, 1998, vol. 2, No. 6, pp. 412-414.
Zhang et al; "A method for removal of N-BOC protecting groups from substrates on TFA-sensitive resins". Tetrahedron Letters 39, Jul. 17, 1998, pp. 7439-7442.
Wang, Su-Sun; "p-Alkoxybenzyl Alcohol Resin and EP, PC, p-Alkoxybenzyloxycarbonylhydrazide Resin for Solid Phase Synthesis of Protected Peptide Fragments". Journal of the American Chemical Society, ACS PUblications, US, vol. 95, No. 4, Feb. 21, 1973, pp. 1328-1333.

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr(tBu)
<220> FEATURE:
<221> NAME/KEY: MOD_RES
<222> LOCATION: (3)..(3)
<223> OTHER INFORMATION: Arg(Pbf)
<220> FEATURE:
<221> NAME/KEY: MOD_RES
<222> LOCATION: (5)..(5)
<223> OTHER INFORMATION: Tyr(tBu)
<220> FEATURE:
<223> OTHER INFORMATION: C-term NHNH2

<400> SEQUENCE: 1

Leu Tyr Arg Ala Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NHNH2

<400> SEQUENCE: 2

Leu Tyr Arg Ala Tyr
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Tyr Arg Ala Tyr Cys Lys Tyr Met His
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Lys Tyr Met His
1               5
```

PHOTOLABILE LINKER FOR THE SOLID-PHASE SYNTHESIS OF HYDRAZIDES AND PYRANOPYRAZOLES

CROSS-REFERENCE TO RELATED APPLICATION(S)

This is a U.S. national stage entry of International Patent Application No. PCT/EP2014/069392, filed on Sep. 11, 2014, which claims priority to European Patent Application No. 14155016.0, filed on Feb. 13, 2014, and European Patent Application No. 13183944.1, filed on Sep. 11, 2013, the entire contents of all of which are fully incorporated herein by reference.

SEQUENCE LISTING

The instant application contains a Sequence Listing which has been submitted electronically in ASCII format and is hereby incorporated by reference in its entirety. Said ASCII copy, created on Jun. 6, 2016, is named 030547-9044-US00_SL.txt and is 1,472 bytes in size.

TECHNICAL FIELD

The present invention relates to photolabile hydrazine linkers, which are capable of releasing hydrazide derivatives upon UV irradiation. The linker allows for a new peptide chemical synthesis strategy in which the crude peptide hydrazide may be ligated directly (one-pot) to a Cys-functionalized peptide. Furthermore, the linker unit can be applied to synthesize combinatorial libraries of biological interesting pyranopyrazoles.

BACKGROUND OF THE INVENTION

Organic hydrazides are an essential class of molecules with a wide spectrum of important properties. A sense of its importance can be garnered from the observation that the antitubecular drug isoniazid contains this structural motif. Furthermore, organic hydrazides are versatile building blocks for the synthesis of pharmacologically relevant hydrazones and heterocycles as well as advanced materials. Peptide hydrazides have been widely utilized in bioconjugation reactions to form glyco-conjugates and more recently emerged as powerful precursors for peptide ligation. However, their applicability may be limited in two respects: 1) peptide hydrazides remain challenging to synthesize and require post-synthesis purification, which is a laborious, time-consuming process associated with loss of valuable material; and 2) current peptide hydrazide synthesis strategies are not compatible with all amino acid residues nor their typically modified side-chain derivatives. Therefore, an efficient and mild method for peptide hydrazide synthesis would significantly improve these techniques.

Given the importance of hydrazide derivatives in drug and probe discovery efforts, methods for the solid-phase parallel and combinatorial synthesis of protected hydrazides have been subject to many studies. Peptide hydrazides may be directly synthesized from solid-supported ester-linked peptides by hydrazinolysis (Merrifield, R. B., Adv. Enzymol. 1969, 32, 221. Chang, J. K.; Shimizu, M.; Wang, S. S., J. Org. Chem. 1976, 41. 3255. Merrifield, R. B., J. Am. Chem. Soc. 1963, 85, 2149. Perlow, D. S.; Erb, J. M.; Gould, N. P.; Tung, R. D. Freidinger, R. M. Williams, P. D.; Veber, D. F., J. Org. Chem. 1992 57, 4394. Wang, S. S. J. Org. Chem. 1976, 41, 3258). However, this strategy often requires an excess of hydrazine, which complicates post-cleavage purification. Such hydrazinolysis is neither generally compatible with the Boc/Bzl protecting group strategy, as benzyl esters readily react with hydrazine, nor the base-labile amino protecting groups Phth, For, Fmoc, Dde and Nps, and typically associated with several side-reactions causing low yields of desired peptides, such as those containing side-chain-protected cysteine, aspartic or glutamic acid recidues.

To bypass such problems, synthetic strategies that are based on special hydrazine resins have been proposed. Wang et al. (Wang, S. S.; Merrifield, R. B., J. Am. Chem. Soc. 1969, 91, 6488. Wang, S. S., J. Am. Chem. Soc. 1973, 95, 1328. Wang, S. S.; J. Org. Chem. 1975, 40, 1235) have reported methods for synthesizing peptide hydrazides using alkoxycarbonyl hydrazide resins. Release of peptides from the linkers required 50-95% TFA for 2 hours. Other strategies have relied on commercial trityl and 2-Cl-trityl resins followed by solid-phase substitution of chloride with hydrazine to afford a trityl-based hydrazine linker construct (Stavropoulos, G.; Gatos. D.; Magafa, V.; Barlos, K., Lett. Pept. Sci., 1996, 2, 315-318). Post-synthetic release of compounds was achieved by treating the resin-hydrazides with 1% TFA in AcOH-TFE-DCM (1:2:7). These linkers are nevertheless facing several limitations. Firstly, they do not tolerate C-terminal glutamine, asparagine or aspartic acid recidues (Fang, G.-M.; Li, Y.-M.; Shen, F.; Huang, Y.-C.; Li, J.-B., Lin, Y.; Cui, H.-K.; Liu, L. Angew. Chem., Int. Ed. 2011, 50, 7645-7649. Campayo, L.; Jimenez, B.; Manzano, T.; Navarro, P. Synthesis 1985, 197-200) but also other peptide hydrazides remain challenging to synthesize. Secondly, the use of acidic reaction conditions for liberation of material from the solid support may be a synthetic disadvantage, as some compounds and protecting groups, e.g., Boc and Trt are not compatible with acids. Finally, the use of acid-labile linker strategies also limits the range of chemical transformations applicable to the synthesis of hydrazide derivatives.

Thus, there exists in the art a need for other cleavage principles that are attractive for the introduction of chemical diversity including hydrazide functionality.

BRIEF DESCRIPTION OF THE INVENTION

Photolysis offers a method for cleavage, which is fully orthogonal to chemical methods and thus can provide a solution to the problems discussed above. Furthermore, photolytic cleavage offers exceedingly mild conditions, which are attractive for direct applications in biochemical reactions where contamination with cleavage reagents is undesired.

In a first aspect the present invention relates to a photolabile hydrazine linker which is suitable for synthesis of peptide hydrazides and dihydropyrano[2,3-c]pyrazoles on a solid support.

The photolabile hydrazine linker has the formula I:

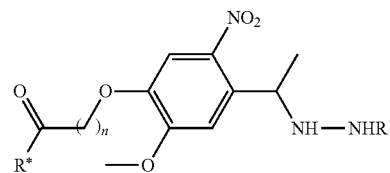

wherein R* is a bond OR', where R' represents hydrogen, $C_{1-12}$ alkyl or substituted $C_{1-10}$ alkyl, aryl, substituted aryl, heteroaryl, substituted heteroaryl or —(CH$_2$—CH$_2$—

O)—$_m$, wherein R is H or a protecting group, m is an integer from 1-100, and n is an integer from 1 to 10.

In one embodiment, the photolabile hydrazine linker is a compound, wherein R* is OH or OR', where R' represents $C_{1-12}$ alkyl or substituted $C_{1-10}$ alkyl, aryl, substituted aryl, heteroaryl, substituted heteroaryl or —(CH$_2$—CH$_2$—O)—$_m$; wherein R is hydrogen or a protecting group, m is an integer from 1-100 and n is an integer from 1 to 10, preferably from 2 to 5, such as from 3 to 5 or n is 3.

In a second aspect, the present invention relates to a method for the synthesis of a photolabile hydrazine linker according to the present invention, wherein R* is OH and R is a protecting group, comprising the steps of a) reacting a compound of formula 2:

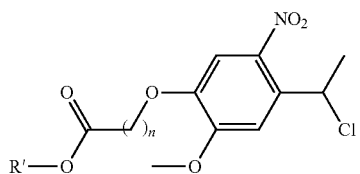

wherein R' represent $C_{1-8}$ alkyl, aryl, heteroaryl or —(CH$_2$—CH$_2$—O)—$_m$, m=1-100, n is an integer from 1 to 10 with PG-carbazate, where PG is a protecting group to obtain a compound of formula 3:

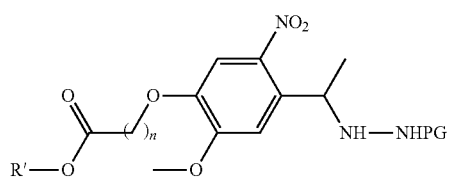

b) hydrolyzing the compound of formula 3 to obtain a compound of formula 4:

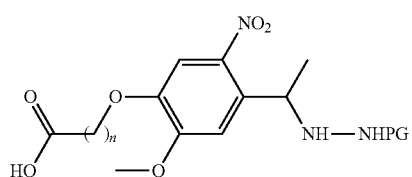

A third aspect of the present invention relates to a solid support comprising the protected hydrazine-functionalized photolabile linker according to the present invention having the formula:

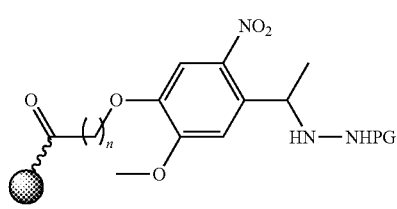

wherein

is a functionalized solid support and PG is a protecting group.

The solid support comprising an immobilized protected hydrazine-functionalized photolabile linker may be synthesized by reacting a functionalized solid support with a protected hydrazine-functionalized photolabile linker according to the present invention defined above, wherein R* is OH and R is a protecting group.

In one embodiment of the invention, the connection between the solid support and the protected hydrazine-functionalized photolabile linker comprises a spacer and/or an orthogonally cleavable linker.

In another embodiment, the solid support comprising a protected hydrazine-functionalized photolabile linker has the following formula:

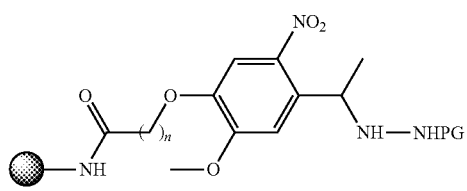

wherein

is an amino-functionalized solid support and PG is a protecting group.

In a further embodiment, the present invention includes a solid support having the formula

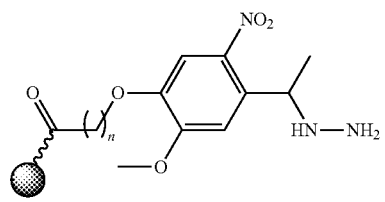

wherein

is a functionalized solid support, wherein the connection between the solid support and the hydrazine-functionalized photolabile linker optionally comprises a spacer and/or an orthogonally cleavable linker.

In yet another embodiment, the present invention includes a solid support comprising an immobilized hydrazine-functionalized photolabile linker having the formula

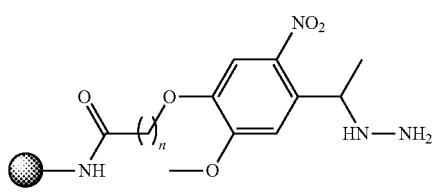

wherein the connection between the solid support and the hydrazine-functionalized photolabile linker optionally comprises a spacer and/or an orthogonally cleavable linker.

In a fourth aspect of the present invention, it relates to the synthesis of peptide hydrazides, wherein the method comprises the steps of:
a) providing a solid support comprising an immobized hydrazine-functionalized photolabile linker according to the present invention,
b) coupling a first N-protected amino acid moiety to said immobilized hydrazine-functionalized photolabile linker,
c) deprotecting said coupled N-protected amino acid moiety,
d) coupling a second N-protected amino acid moiety to said immobilized amino acid moiety,
e) deprotecting said coupled N-protected amino acid moiety,
f) repeating said coupling and deprotecting steps d and e as many times as necessary to synthesize an immobilized peptide as desired,
g) cleaving said immobilized hydrazine-functionalized peptide from the solid support by irradiation of the photolabile linker to obtain the peptide hydrazide.

In one embodiment, the immobilized peptide is cleaving from the solid support by irradiation in the presence of acetone/$CH_3CN$ to obtain a peptide hydrazide protected as it corresponding acetone hydrazone which optionally is deprotected in the presence of water.

The amino acid moieties are selected among all natural and unnatural amino acids and derivatives thereof. The amino acid moiety may also be composed of two or more natural and/or unnatural amino acids or derivatives thereof. Preferably, the amino acids are selected among the natural occurring amino acids.

The synthesis strategy shows excellent compatibility with peptide composition, notably all 20 naturally occurring α-amino acid residues (even the side-chain protected analogs) were accepted at the C-terminal hydrazide moiety. The linker is compatible with most commonly used protecting groups for SPPS and remains intact throughout the multi-step peptide synthesis.

Products are ultimately released as hydrazides (in situ trapped as acetone-derived hydrazone derivatives) from the solid support in high purity using light.

In a fifth aspect of the present invention, the invention relates to the use of the hydrazine-functionalized photolabile linker of the present invention for chemical synthesis of oligo- or polypeptides. Accordingly, the present invention also concerns a method for the synthesis of oligo- or polypeptides, which method comprises the steps of 1) obtaining a peptide hydrazide or acetone hydrazone protected peptide hydrazide in a method as disclosed above, and 2) coupling said peptide hydrazide with a peptide in a ligation reaction to obtain an oligo- or polypeptide.

The direct ligation of a crude peptide hydrazide to a Cys-functionalized peptide provided a 10-mer peptide in high purity and excellent yield. it is envisaged that this one-pot strategy may enable more convergent protein synthesis and render it even more complementary to native chemical ligation.

In a sixth aspect, the present invention relates to the use of the hydrazine-functionalized photolabile linker of the present invention for the synthesis of dihydropyrano[2,3-c]pyrazoles. A two-step synthetic protocol followed by photolytic release provided structurally diverse dihydropyrano[2,3-c]pyrazoles in excellent purity. Accordingly, the present invention also concerns a method for the synthesis of dihydropyrano[2,3-c]pyrazoles of the formula:

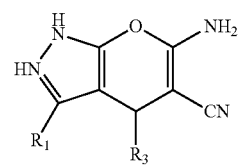

wherein $R_1$ is selected from $C_{1-8}$ alkyl, aryl, mono- or multiply-substituted aryl, heteroaryl, mono- or multiply-substituted heteroaryl, where the substituents may be $C_1$-$C_8$ alkyl, $C_1$-$C_8$ alkoxy, halogen, nitrile or nitro and $R_3$ is selected from aryl, mono- or multiply-substituted aryl, heteroaryl and substituted heteroaryl, where the substituents are the same or different and represent $C_1$-$C_8$ alkyl, $C_1$-$C_8$ alkoxy, halogen, nitrile or nitro comprising the steps of:
a) providing a solid support comprising a hydrazine-functionalized photolabile linker as defined above,
b) reacting said hydrazine-functionalized photolabile linker with a β-keto ester with the formula:

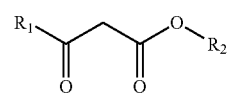

wherein $R_2$ is $C_1$-$C_8$ alkyl, preferably methyl or ethyl, to obtain an immobilized 1H-pyrazol-5(4H)-one with formula:

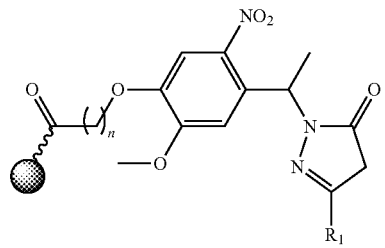

c) reacting the 1H-pyrazol-5(4H)-one with an aldehyde $R_3$—CO, wherein $R_3$ is selected from aryl, substituted aryl, heteroaryl and substituted heteroaryl, in the presence of malononitrile to obtain an immobilized dihydropyrano[2,3-c]pyrazole with the formula:

d) cleaving said immobilized compound from the solid support by irradiation of the photolabile linker to obtain the dihydropyrano[2,3-c]pyrazole.

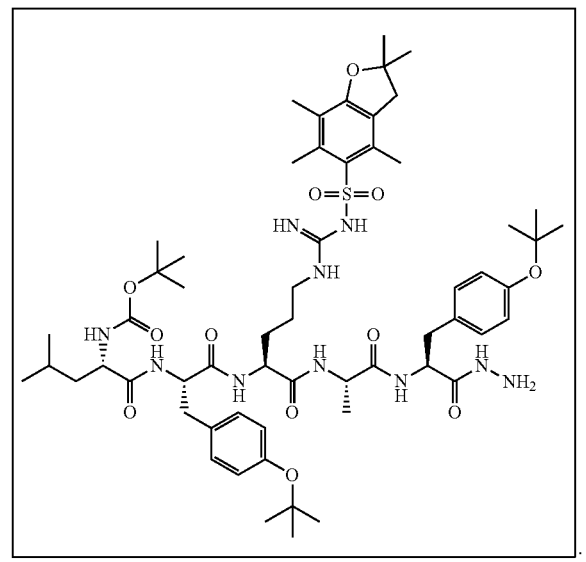 [SMILES: Cc1c(C)c(S(=O)(=O)NC(=N)NCCC[C@H](NC(=O)[C@H](Cc2ccc(OC(C)(C)C)cc2)NC(=O)[C@H](CC(C)C)NC(=O)OC(C)(C)C)C(=O)N[C@@H](C)C(=O)N[C@@H](Cc2ccc(OC(C)(C)C)cc2)C(=O)NN)c(C)c2c1OC(C)(C)C2]

Figure 1:
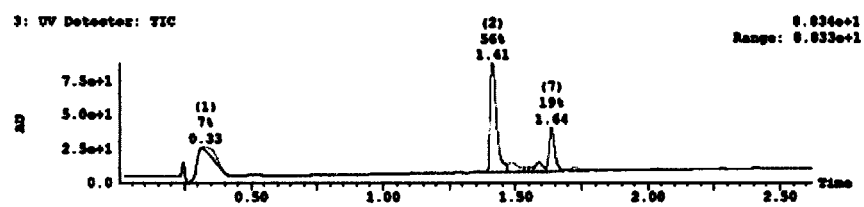
FIG. 1 shows the RP-HPLC of crude 8a and 9a after photorelease in $CH_3CN$/acetone (1:4), where 9a: Rt=1.41, 8a: Rt=1.64.
Figure 2:
FIG. 2 shows the RP-HPLC of crude 8b and 9b after photorelease in $CH_3CN$/acetone (1:4), where 9b: Rt=1.09, 8a: Rt=1.40.
Figure 3:
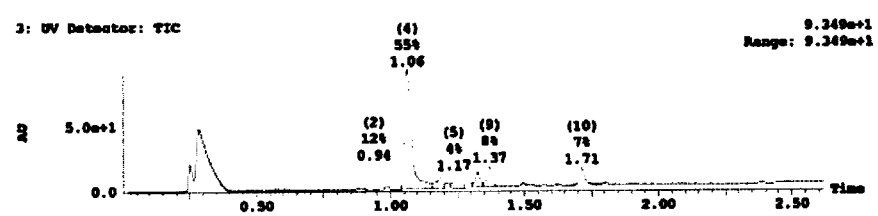
FIG. 3 shows the RP-HPLC of crude 8b and 9b after photorelease in $CH_3CN$/acetone (1:4): followed by removal of excess acetone by evaporation and addition of water/$CH_3CN$ (1:4).
Figure 4:
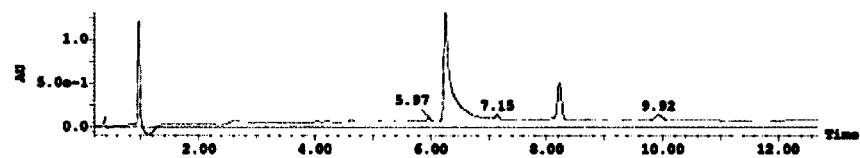
FIG. 4 shows the RP-HPLC of crude 8c and 9c after photorelease in $CH_3CN$/acetone (1:4), where 8c: Rt=6.31, 9c: Rt=8.21.
Figure 5:
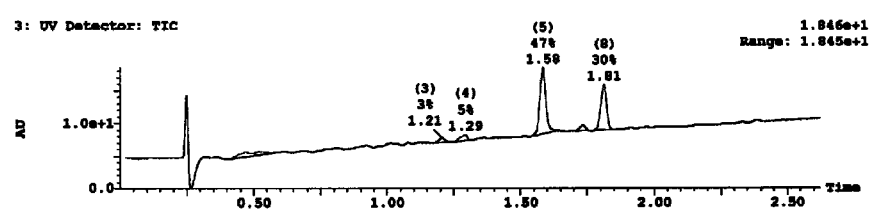
FIG. 5 shows the RP-HPLC of crude 8d and 9d after photorelease in $CH_3CN$/acetone (1:4), where 8d: Rt=1.58 (m/z=490.3), 9d: Rt=1.81.
Figure 6:
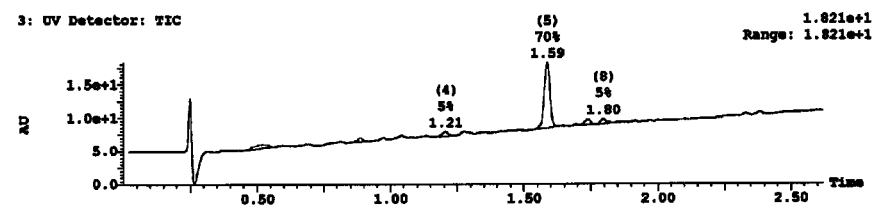
FIG. 6 shows the RP-HPLC of crude 27d and 28d after photorelease in $CH_3CN$/acetone (1:4), followed by removal of excess acetone by evaporation and addition of water/$CH_3CN$ (1:4), where 28d: Rt=1.58.
Figure 7:
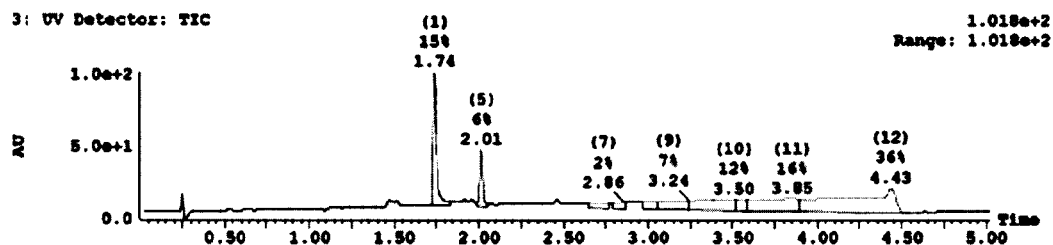
FIG. 7 shows the RP-HPLC of crude 8e and 9e after photorelease in $CH_3CN$/acetone (1:4).
Figure 8:
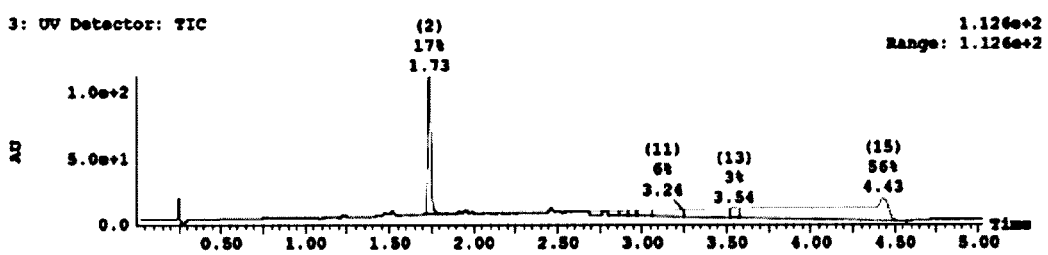
FIG. 8 show the RP-HPLC of crude 8e and 9e after photorelease in $CH_3CN$/acetone (1:4), followed by removal of excess acetone by evaporation and addition of water/$CH_3CN$ (1:4), where 9e: Rt=1.73.
Figure 9:
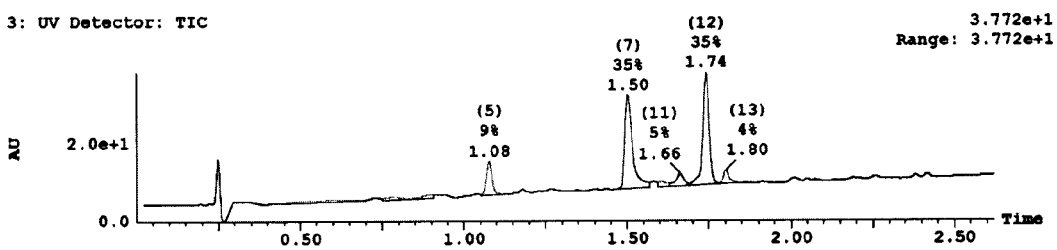
FIG. 9 shows the RP-HPLC of crude 8h and 9h after photorelease in $CH_3CN$/acetone (1:4), where 9h: Rt=1.81 (m/z=464.4)), 8h: Rt=1.83 (m/z=504.4).
Figure 10:
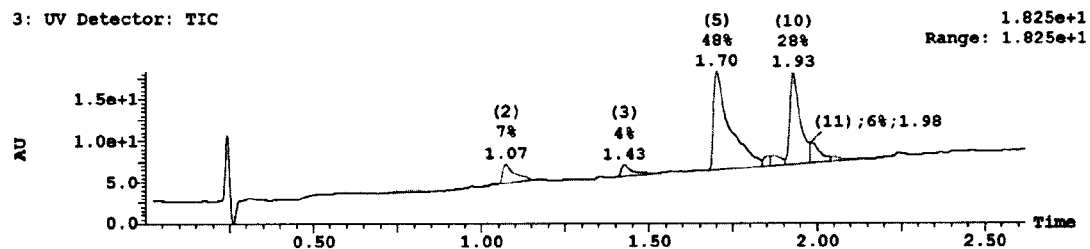
FIG. 10 shows the RP-HPLC of crude 8i and 9i after photorelease in $CH_3CN$/acetone (1:4), where 9i: Rt=1.56 (m/z=524.3), 8i: Rt=1.77 (m/z=564.4).
Figure 11:
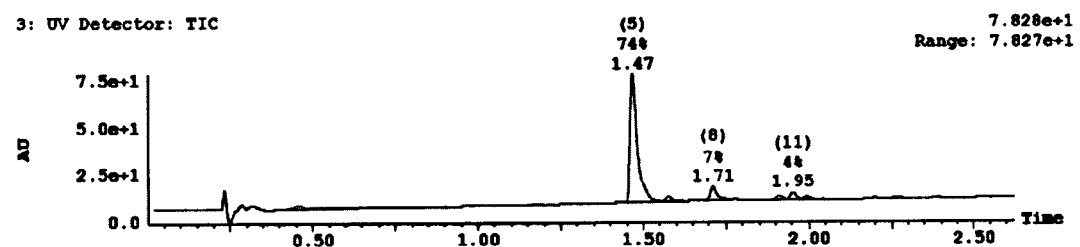
FIG. 11 shows the RP-HPLC of crude 8j and 9j after photorelease in $CH_3CN$/acetone (1:4), where 9j: Rt=1.47, 8j: Rt=1.71.
Figure 12:
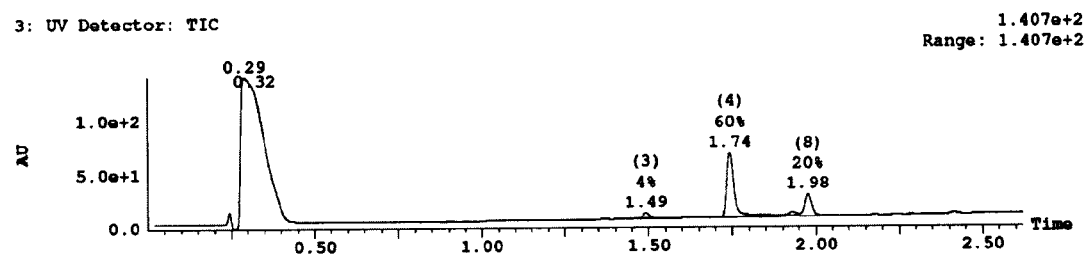
FIG. 12 shows the RP-HPLC of crude 8k and 9k after photorelease in $CH_3CN$/acetone (1:4), where 9i: Rt=1.74, 8i: Rt=1.98.
Figure 13:
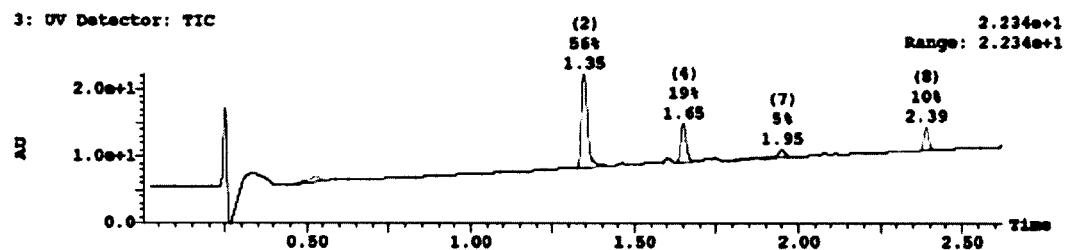
FIG. 13 shows the RP-HPLC of crude 8l and 9l after photorelease in $CH_3CN$/acetone (1:4), where 9l: Rt=1.35, 8l: Rt=1.65.
Figure 14:
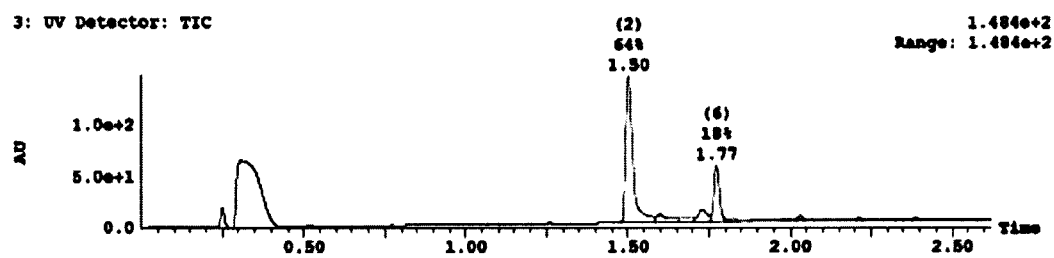
FIG. 14 shows the RP-HPLC of crude 8m and 9m after photorelease in $CH_3CN$/acetone (1:4), where 9m: Rt=1.50, 8m: Rt=1.77.
Figure 15:
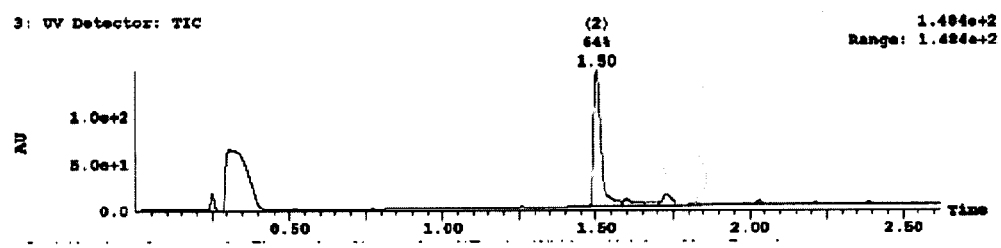
FIG. 15 shows the RP-HPLC of crude 8m and 9m after photorelease in $CH_3CN$/acetone (1:4), followed by removal of excess acetone by evaporation and addition of water/$CH_3CN$ (1:4), where 9m: Rt=1.50.
Figure 16:
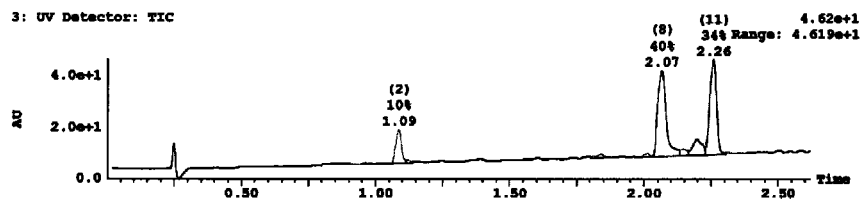
FIG. 16 shows the RP-HPLC of crude 8o and 9o after photorelease in $CH_3CN$/acetone (1:4), where 9O: Rt=2.07 (m/z=612.4), 8o: Rt=2.26 (m/z=652.5).
Figure 17:
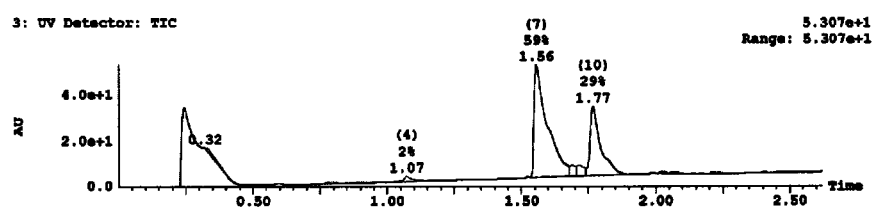
FIG. 17 shows the RP-HPLC of crude 8q and 9q after photorelease in $CH_3CN$/acetone (1:4), where 9q: Rt=1.56 (m/z=537.3), 8q: Rt=1.77 (m/z=577.3).
Figure 18:
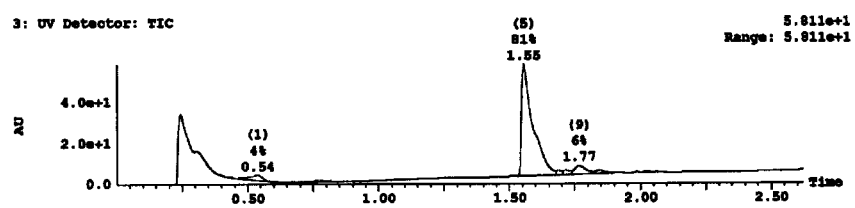
FIG. 18 shows the RP-HPLC of crude 8q and 9q after photorelease in $CH_3CN$/acetone (1:4), followed by removal of excess acetone by evaporation and addition of water/$CH_3CN$ (1:4), where 9q: Rt=1.56 (m/z=537.3), 8q: Rt=1.77 (m/z=577.3).
Figure 19:
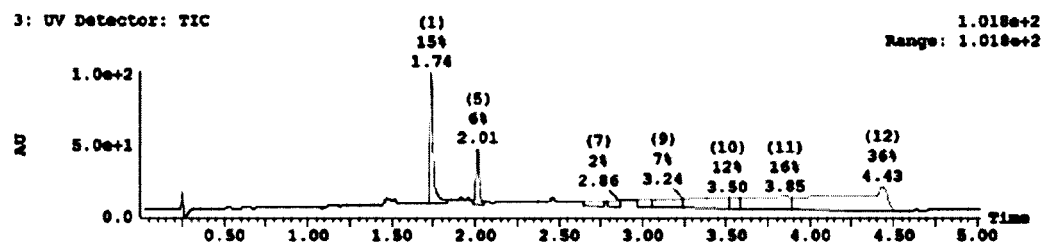
FIG. 19 shows the RP-HPLC of crude 8r and 9r after photorelease in $CH_3CN$/acetone (1:4), where 9r: Rt=1.72, 8r: Rt=1.95.
Figure 20:
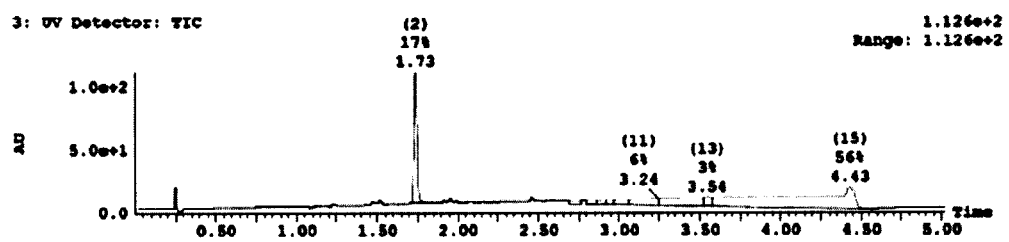
FIG. 20 shows the RP-HPLC of crude 8r and 9r after photorelease in $CH_3CN$/acetone (1:4), followed by removal of excess acetone by evaporation and addition of water/$CH_3CN$ (1:4), where 9r: Rt=1.72.
Figure 21:
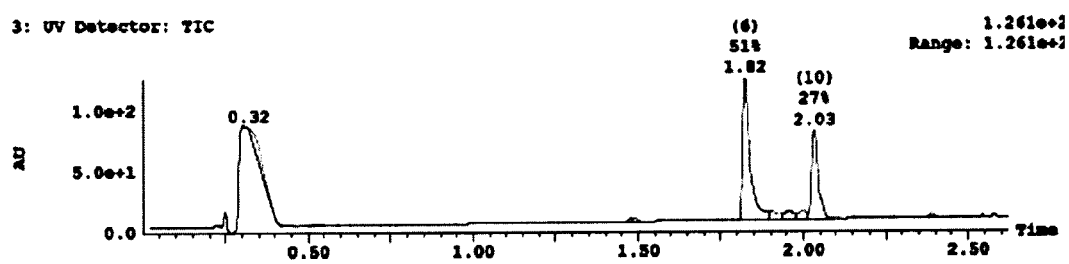
FIG. 21 shows the RP-HPLC of crude 8s and 9s after photorelease in $CH_3CN$/acetone (1:4), where 9s: Rt=1.82, 8s: Rt=2.03.
Figure 22:
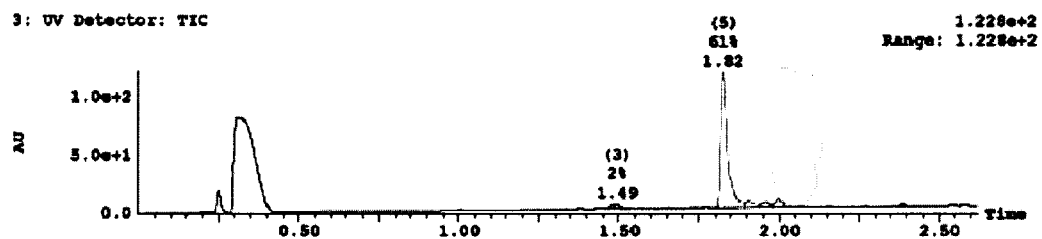
FIG. 22 shows the RP-HPLC of crude 8s and 9s after photorelease in $CH_3CN$/acetone (1:4), followed by removal of excess acetone by evaporation and addition of water/$CH_3CN$ (1:4), where 9s: Rt=1.82.
Figure 23:
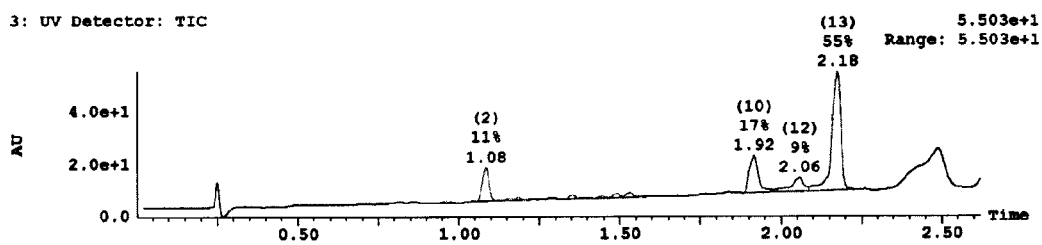
FIG. 23 shows the RP-HPLC of crude 8t and 9t after photorelease in $CH_3CN$/acetone (1:4), where 8t: Rt=1.92 (m/z=550.4), 9t: Rt=2.18 (m/z=590.4).
Figure 24:
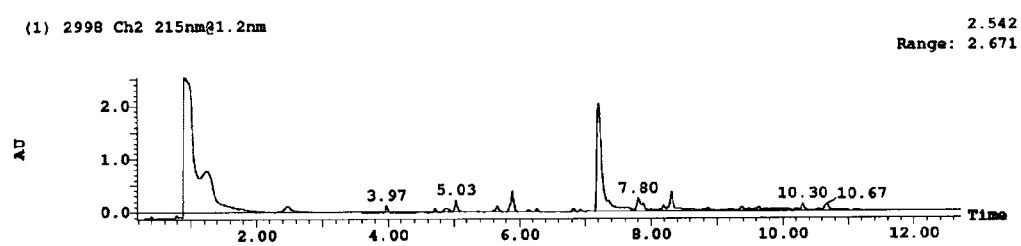
FIG. 24 shows the RP-HPLC of crude 8t and 9t after photorelease in $CH_3CN$/acetone (1:4) followed by removal of excess acetone by evaporation and addition of water/$CH_3CN$ (1:4).
Figure 25:
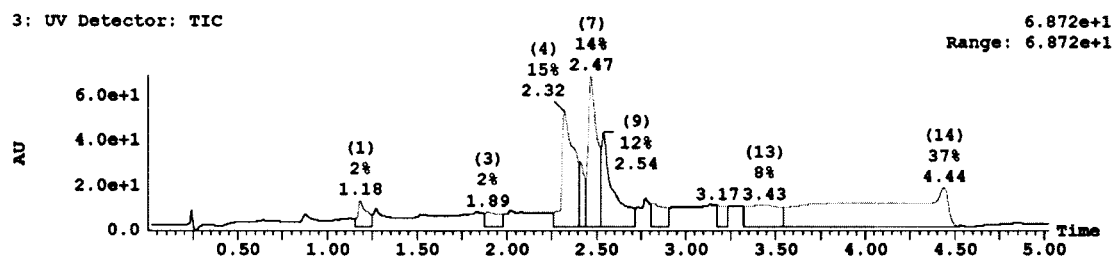
FIG. 25 shows the RP-HPLC of crude 8u and 9u after photorelease in $CH_3CN$/acetone (1:4), where 9u: Rt=2.32 (m/z=779.5), 8u: Rt=2.47 (m/z=819.5).
Figure 26:
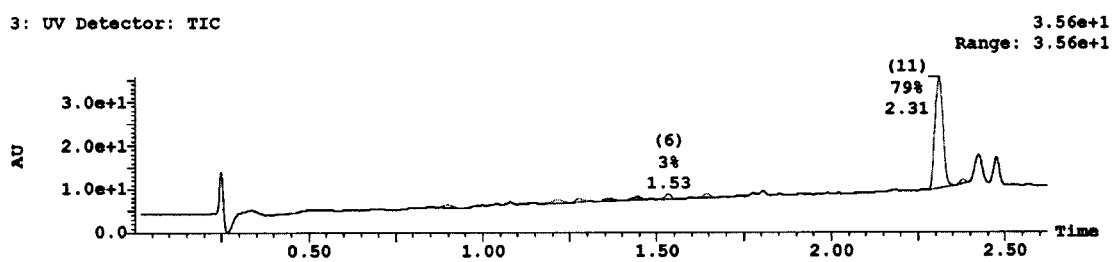
FIG. 26 shows the RP-HPLC of crude 8v and 9v after photorelease in $CH_3CN$/acetone (1:4), followed by removal of excess acetone by evaporation and addition of water/$CH_3CN$ (1:4), where 9v: Rt=2.31 (m/z=763.5).
Figure 27:
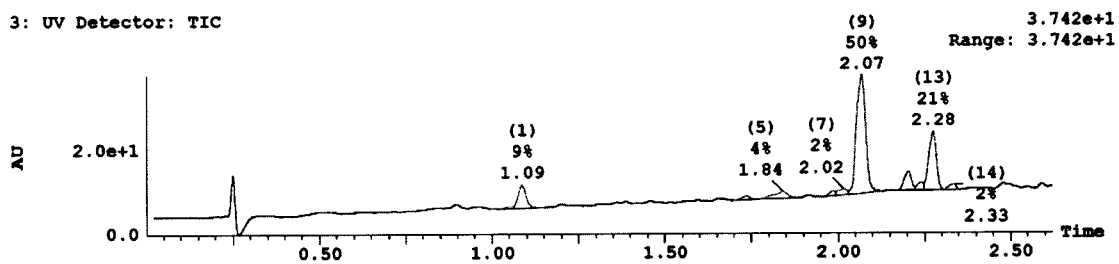
FIG. 27 shows the RP-HPLC of crude 8w and 9w after photorelease in $CH_3CN$/acetone (1:4), where 9w: Rt=2.07 (m/z=584.3), 8w: Rt=2.28 (m/z=624.4).
Figure 28:
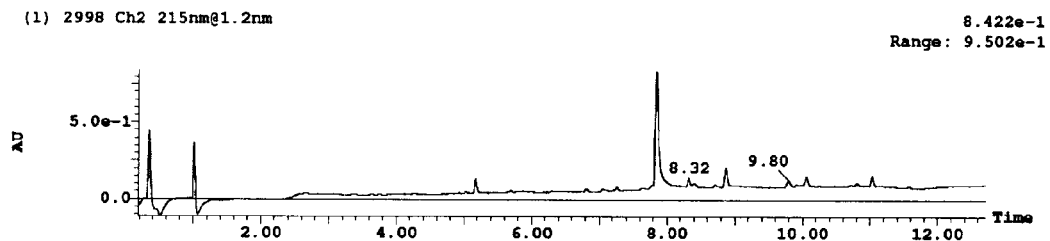
FIG. 28 shows the RP-HPLC of crude 8w and 9w after photorelease in $CH_3CN$/acetone (1:4) followed by removal of excess acetone by evaporation and addition of water/$CH_3CN$ (1:4).
Figure 29:
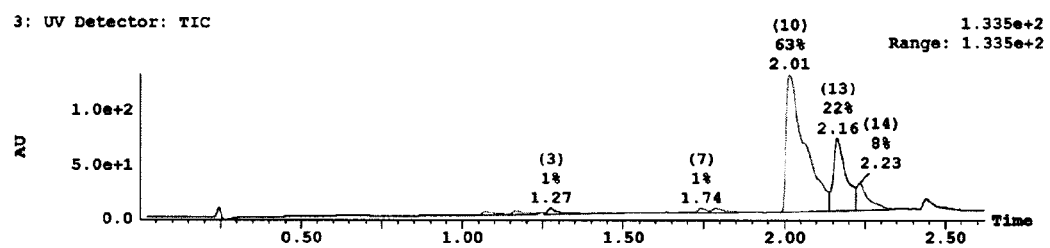
FIG. 29 shows the RP-HPLC of crude 8x and 9x after photorelease in $CH_3CN$/acetone (1:4), where 9x: Rt=2.01 (m/z=831.5), 8x Rt=2.16 (m/z=871.5).
Figure 30:
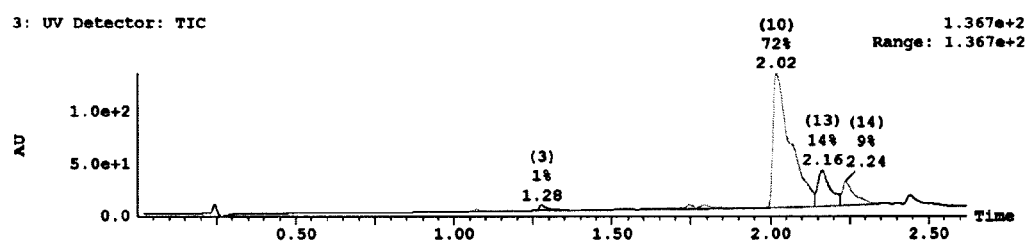
FIG. 30 shows the RP-HPLC of crude 9x and 8x after photorelease in $CH_3CN$/acetone (1:4) followed by removal of excess acetone by evaporation and addition of water/$CH_3CN$ (1:4), where 9x: Rt=2.02 (m/z=831.5), 8x: Rt=2.16 (m/z=871.5).
Figure 31:
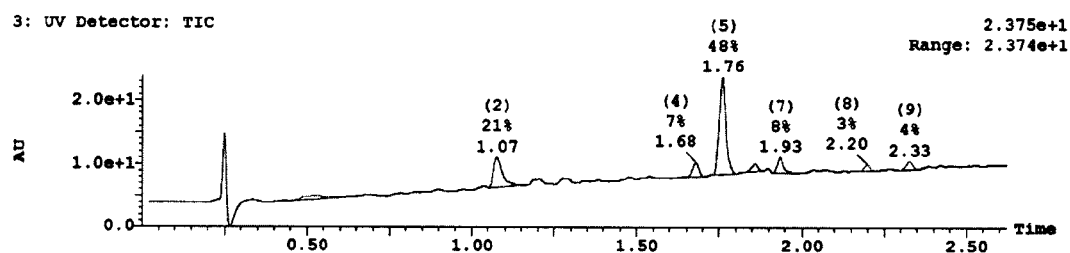
FIG. 31 shows the RP-HPLC of crude 8y and 9y after photorelease in $CH_3CN$/acetone (1:4) followed by removal of excess acetone by evaporation and addition of water/$CH_3CN$ (1:4), where 8y: Rt=1.76 (m/z=616.5), 9y: Rt=1.93, Rt=1.07: 8y-Boc.
Figure 32:
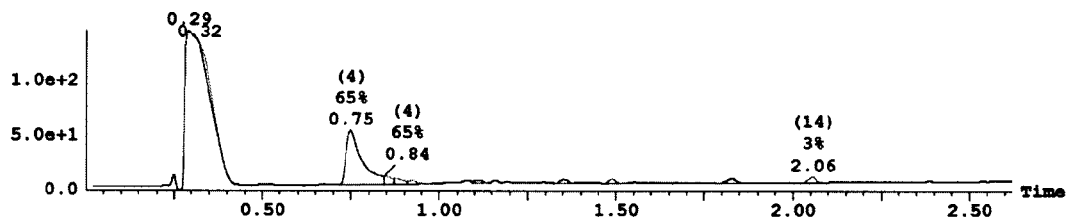
FIG. 32 shows the RP-HPLC of crude 8z and 9z after photorelease in $CH_3CN$/acetone (1:4), where 8z: Rt=0.75.
Figure 33:
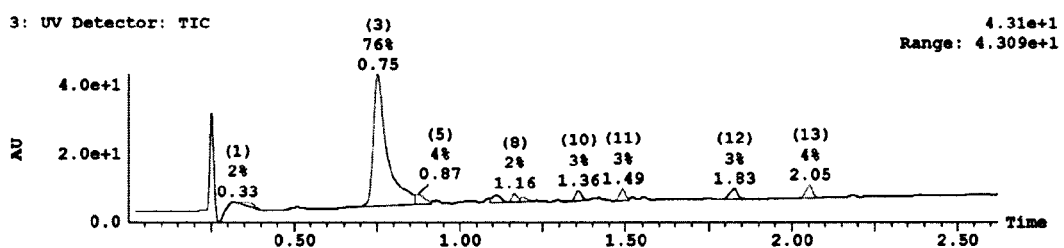
FIG. 33 shows the RP-HPLC of crude 8z and 9z after photorelease in $CH_3CN$/acetone (1:4) followed by removal of excess acetone by evaporation and addition of water/$CH_3CN$ (1:4), where 8z: Rt=0.75.
Figure 34:
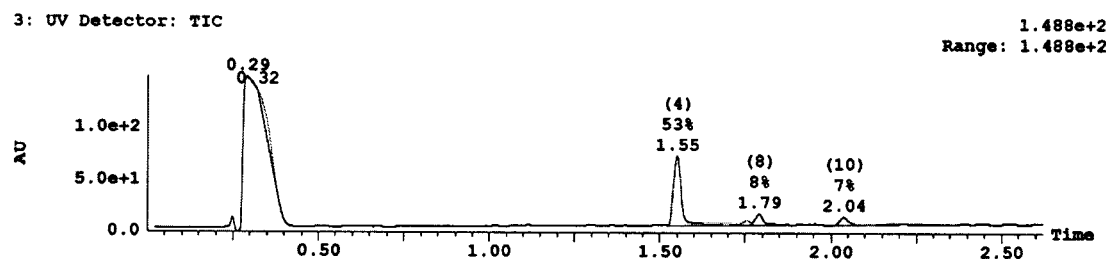
FIG. 34 shows the RP-HPLC of crude 8aa and 9aa after photorelease in $CH_3CN$/acetone (1:4) followed by removal of excess acetone by evaporation and addition of water/ CH$_3$CN (1:4), where 9aa: Rt=1.55, 8aa: Rt=1.79.
Figure 35:
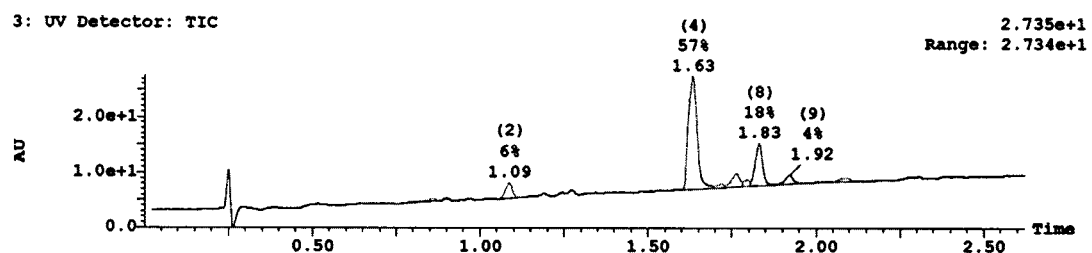
FIG. 35 shows the RP-HPLC of crude 8ab and 9ab after photorelease in CH$_3$CN/acetone (1:4), where 9ab: Rt=1.63 (m/z=579.4), 8ab: Rt=1.83 (m/z=619.5).
Figure 36:
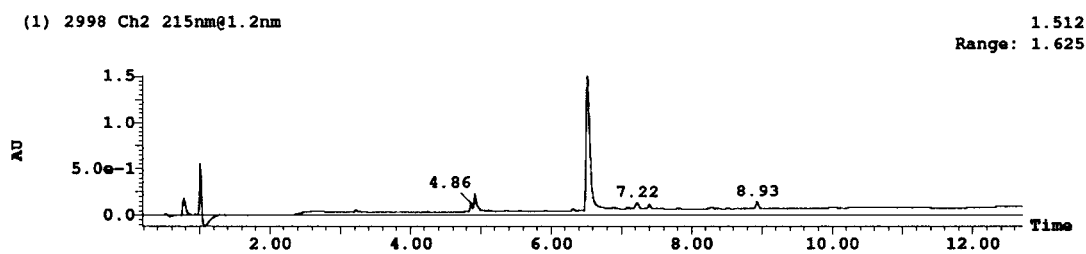
FIG. 36 shows the RP-HPLC of crude 8ab and 9ab after photorelease in CH$_3$CN/acetone (1:4) followed by removal of excess acetone by evaporation and addition of water/ CH$_3$CN (1:4).
Figure 37:
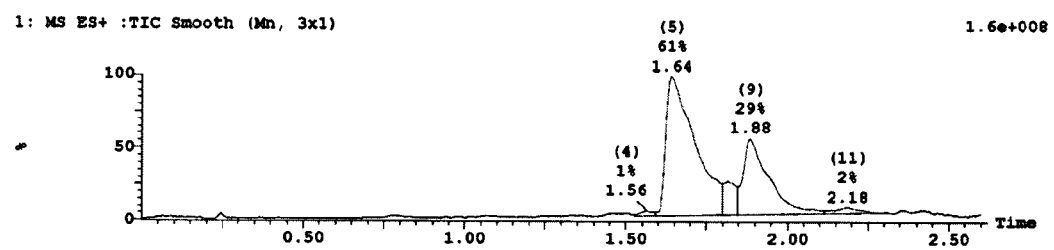
FIG. 37 shows the RP-HPLC of crude 8ac and 9ac after photorelease in CH$_3$CN/acetone (1:4) followed by removal of excess acetone by evaporation and addition of water/ CH$_3$CN (1:4), where 9ac: Rt=1.64 (m/z=451.3), 8ac: Rt=1.89 (m/z=491.3).
Figure 38:
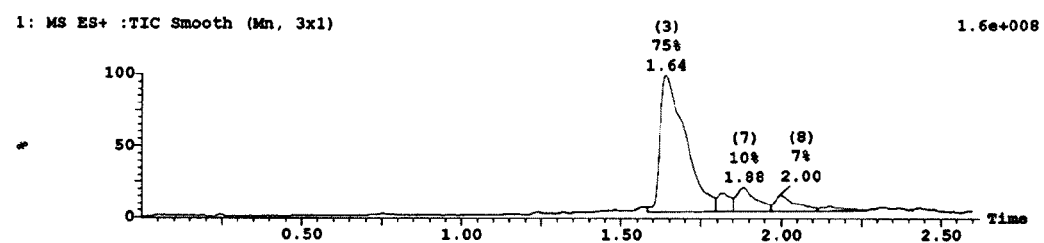
FIG. 38 shows a RP-HPLC of 9ac.
Figure 39:
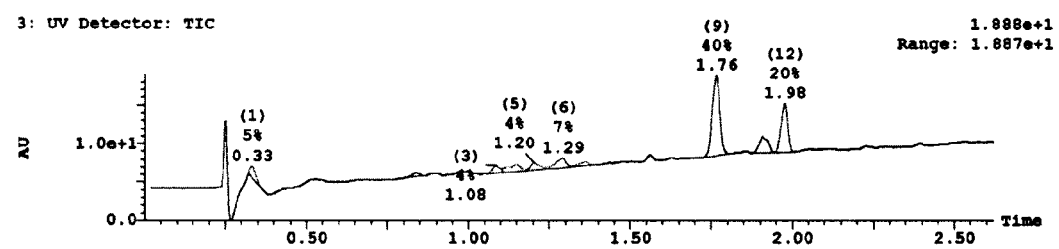
FIG. 39 shows the RP-HPLC of crude 8ad and 9ad after photorelease in CH$_3$CN/acetone (1:4), where 8ac: Rt=1.76 (m/z=562.5), 9ac: Rt=1.98 (m/z=602.5).
Figure 40:
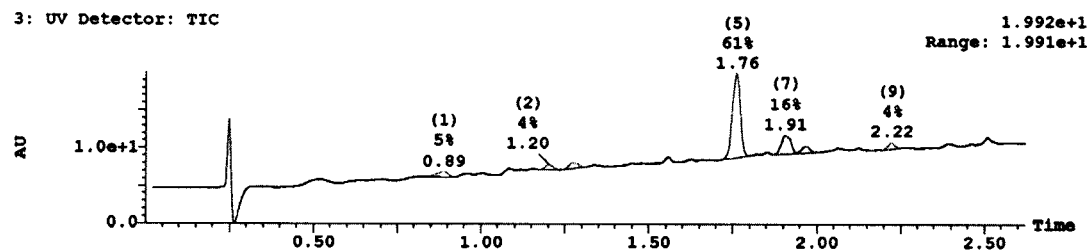
FIG. 40 shows the RP-HPLC of crude 8ac and 9ac after photorelease in CH$_3$CN/acetone (1:4) followed by removal of excess acetone by evaporation and addition of water/ CH$_3$CN (1:4), where 8ac: Rt=1.76 (m/z=562.5).
Figure 41:
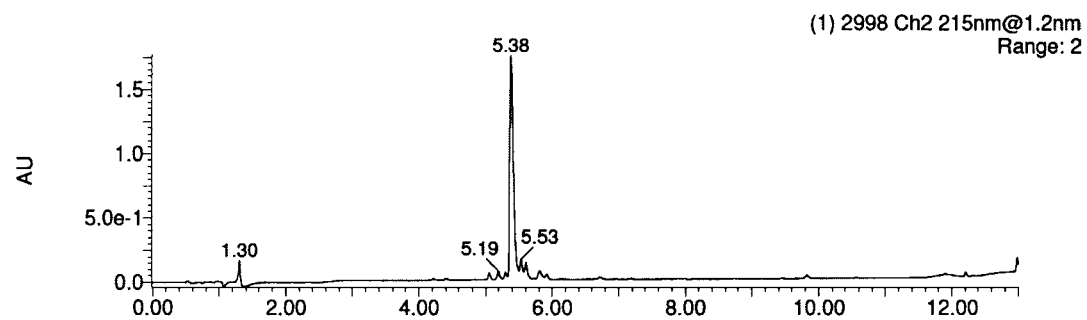
FIG. 41 shows an HPLC of compound 14.
Figure 42:
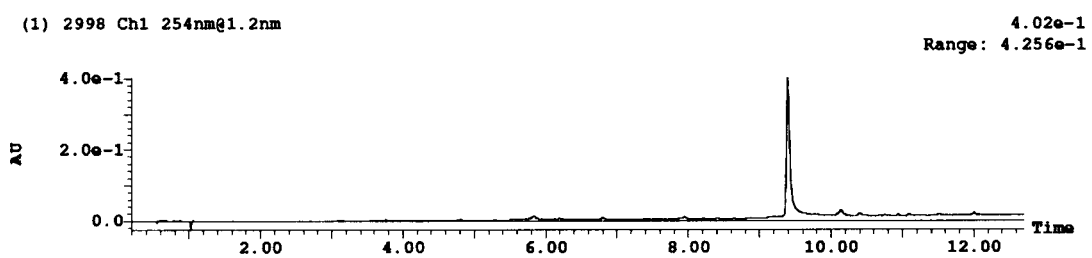
FIG. 42 shows an HPLC of compound
Figure 43:
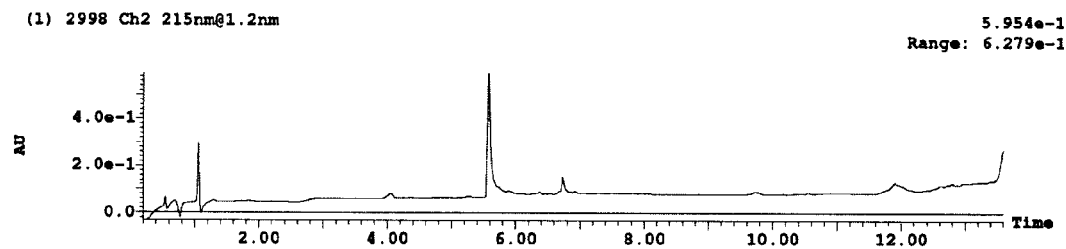

FIG. 43 shows an HPLC of crude H-Leu-Tyr-Arg-Ala-Tyr-NHNH$_2$ (13).

Figure 44A:
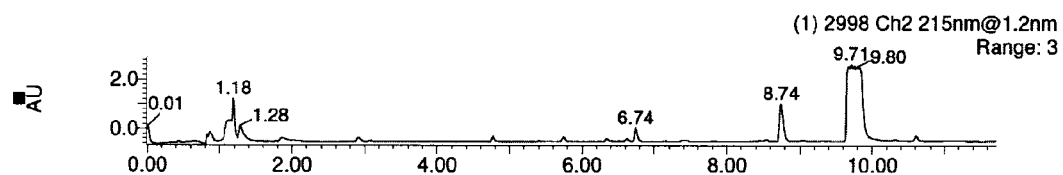

FIG. 44a shows the crude RP-HPLC after 2h of the ligation with cysteine, where 16: Rt=6.74, 13b: Rt=8.74.

Figure 44B:
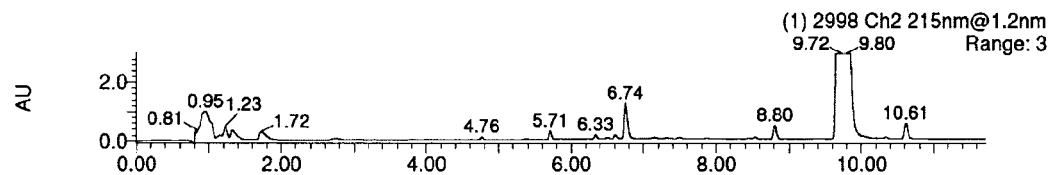

FIG. 44b shows the crude RP-HPLC after 12h of the ligation with cysteine, where 16: Rt=6.74, 13b: Rt=8.80.

Figure 45:
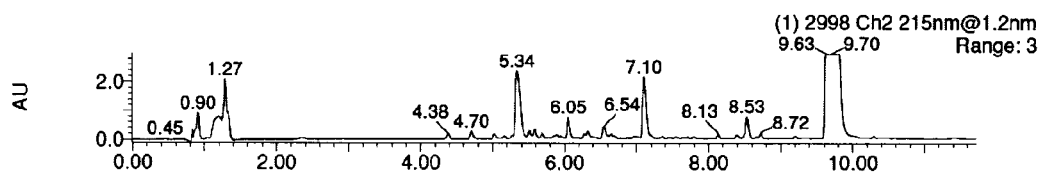

FIG. 45 shows the crude RP-HPLC after 12h of the formation of 15, where 15: Rt=7.19, 14: Rt=5.34, 13b: Rt=8.53.

Figure 46:
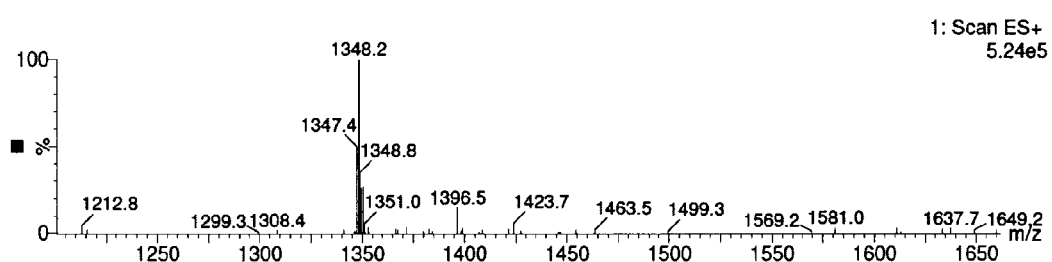

FIG. 46 shows the UPLC-MS traces corresponding to peak rt=7.10.

Figure 47:
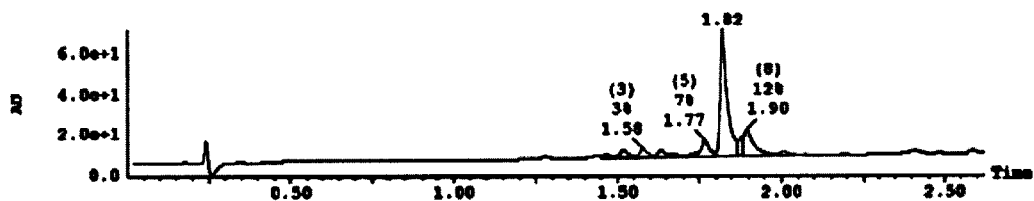

FIG. 47 shows the RP-HPLC of crude 12a after photorelease in H$_2$O/MeOH (1:4), where 12a: Rt=1.82 (Rt=1.90 corresponds to 2,4-dihydro tautomer).

Figure 48:

FIG. 48 shows the RP-HPLC of crude 12b after photorelease in H$_2$O/MeOH (1:4), where 12b: Rt=1.77 (Rt=1.84 corresponds to 2,4-dihydro tautomer).

Figure 49:

FIG. 49 shows the RP-HPLC of crude 18c after photorelease in H$_2$O/MeOH (1:4), where 18c: Rt=1.85 (Rt=1.94 corresponds to 2,4-dihydro tautomer).

Figure 50:
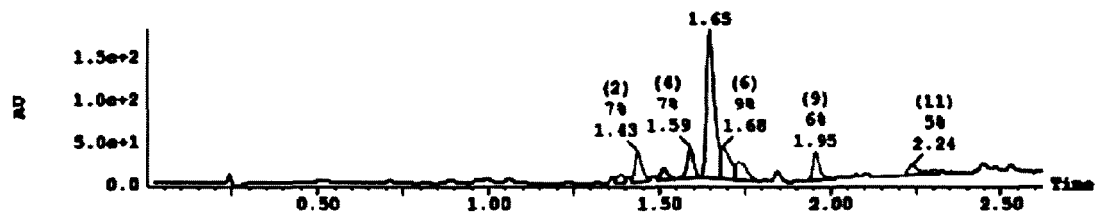

FIG. 50 shows the RP-HPLC of crude 12d after photorelease in H$_2$O/MeOH (1:4), where 12d: Rt=1.65.

Figure 51:
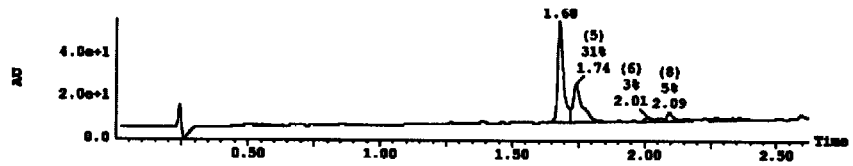

FIG. 51 shows the RP-HPLC of crude 12e after photorelease in H$_2$O/MeOH (1:4), where 12e: Rt=1.68 (Rt=1.74 corresponds to 2,4-dihydro tautomer).

Figure 52:
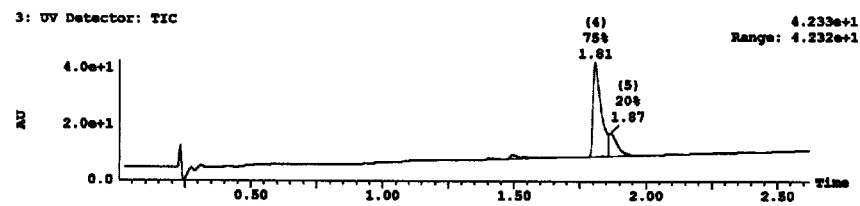

FIG. 52 shows the RP-HPLC of crude 12f after photorelease in H$_2$O/MeOH (1:4), where 12f: Rt=1.81 (Rt=1.87 corresponds to 2,4-dihydro tautomer).

Figure 53:
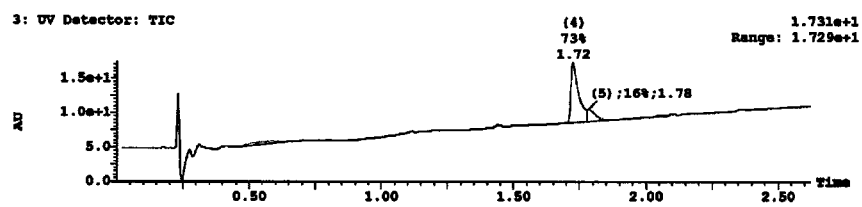

FIG. 53 shows the RP-HPLC of crude 12g after photorelease in H$_2$O/MeOH (1:4), where 12g: Rt=1.72 (Rt=1.78 corresponds to 2,4-dihydro tautomer).

Figure 54:
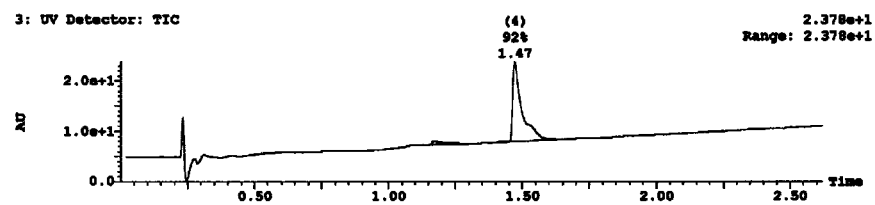

FIG. 54 shows the RP-HPLC of crude 12h after photorelease in H$_2$O/MeOH (1:4), where 12h: Rt=1.47.

DETAILED DESCRIPTION OF THE INVENTION

The photolabile hydrazine linker of the present invention is based on the o-nitro-veratryl group, which is capable of releasing hydrazide derivatives upon UV irradiation. The linker allows for a new solid-phase peptide synthesis (SPPS) strategy which is fully orthogonal to the most commonly used protecting groups and chemical methods in SPPS and shows excellent compatibility with peptide composition, notably all 20 naturally occurring α-amino acid residues (even in their side-chain protected form) are accepted in the C-terminal of the peptide hydrazides. Furthermore, the linker unit can be applied to synthesize combinatorial libraries of biological interesting heterocyclic compounds, e.g. pyranopyrazoles.

Abbreviations

Fmoc=fluorenylmethyloxycarbonyl—removed by base, such as piperidine.
Boc=t-butyloxycarbonyl—removed by acid, such as HCl and CF$_3$COOH.
Trt=trityl—removed by acid, such as HCl and CF$_3$COOH
Alloc=allyloxycarbonyl—removed by tetrakis(triphenylphosphine)palladium(0) in a mixture of methylene chloride, acetic acid, and N-Methylmorpholine
tBu=tert-butyl—removed by acid, such as HCl and CF$_3$COOH.
Cbz=carbobenzyloxy-removed by hydrogenolysis.
Bn=benzyl—removed by hydrogenolysis.
SiR$_3$, where R can be combinations of different groups. Common silyl protective groups are trimethylsilyl (TMS), tert-butyldiphenylsilyl (TBDPS), tert-butyldimethylsilyl (TBS/TBDMS) and triisopropylsilyl (TIPS), [2-(trimethylsilyl)ethoxy]methyl (SEM)—removed with acids or fluorides such as HF and tetra-n-butylammonium fluoride. Larger R-substituents increase resistance to hydrolysis.
Rink-linker=2-(4-(amino(2,4-dimethoxyphenyl)methyl) phenoxy)acetic acid
Rink amide linker: 4-[(2,4-dimethoxyphenyl)(Fmoc-amino) methyl]phenoxyacetic acid
NEM: N-ethyl morpholine.
PEGA: polyethylene glycol dimethyl acrylamide.
TBTU: O-(benzotriazol-1-yl)-N,N,N',N'-tetramethyluronium tetrafluorobrate
HATU: O-(7-azabenzotriazol-1-yl)-N,N,N',N'-tetramethyluronium hexafluorophosphate
TLC: Thin layer chromatography
HFIP: hexaflouroisopropanol TFA: trifluoroacetic acid
HPLC: High-performance liquid chromatography
HDAC: histone deacetylase
pyBOP: benzotriazol-1-yl-oxytripyrrolidinophosphonium hexafluorophosphate
DIPEA: N,N, Diisopropylethylamine
DMF: Dimethylformamide
NMP: N-methyl-2-pyrrolidone
SPPS: solid-phase peptide synthesis
PBS: phosphate buffered saline
PG-carbazate: hydrazine protecting group—hydrazinocarboxylate. For example tert-butyl carbazate ($H_2N$—NHBoc).

Definitions

Support/Solid Support/Solid Phase.

Nature of the solid support: Solid supports that can be functionalized with the linker may be of any shape or size, such as roughly spherical (beads) or a planer surface. The solid supports need not necessarily be homogenous in size, shape or composition; although the solid supports usually and preferably will be uniform.

The physical properties of the solid support, and the applications to which it can be utilized, vary with the material from which the support is constructed, the amount of cross-linking, as well as the linker and handle being used. It is believe that supports should have the minimum amount of cross-linking to confer stability. This should result in a well-solvated system where solid-phase synthesis and can be carried out. Nonetheless, the characteristics of an efficient solid support include:

It must be physically stable and permit the rapid filtration of liquids, such as excess reagents.
It must be inert to all reagents and solvents used during synthesis.
It must swell extensively in the solvents used to allow for penetration of the reagents.
It must allow for the attachment of the photolabile linker of the present invention
There are three primary types of solid supports:
Gel-type supports: These are highly solvated polymers with an equal distribution of functional groups. This type of support is the most common, and includes:
  Polystyrene: Styrene cross-linked with 1-2% divinylbenzene
  Polyacrylamide: A hydrophilic alternative to polystyrene
  Polyethylene glycol (PEG): PEG-Polystyrene (PEG-PS) is more stable than polystyrene and spaces the site of synthesis from the polymer backbone
  PEG-based supports: Composed of a PEG-polypropylene glycol network or PEG with polyamide or polystyrene
Surface-type supports: Many materials have been developed for surface functionalization, including controlled pore glass, cellulose fibers, and highly cross-linked polystyrene.
Composites: Gel-type polymers supported by rigid matrices.

The chemically reactive groups with which such solid supports may be derivatized are those commonly used for solid phase synthesis, i.e., amino and hydroxyl.

For on-bead synthesis, the solid support is preferably composed by polymeric beads, limited primarily by capacity for swelling, light permeability and the capacity for derivatization to attach any of a number of chemically reactive groups as well as compatibility with the synthetic chemistry used for linker attachment and/or synthesis. Suitable solid support materials typically will be the type of material commonly used in peptide and polymer synthesis. To improve swelling properties quite porous beads, resins, or other supports work well and are often preferable. Particularly preferred materials include polystyrene, polypropylene, polyethylene glycol and polyacrylamide resins, e.g. TentaGel® or Chemmatrix®.

Activating Group:

refers to a group which, when attached to a particular functional group, renders that site more reactive toward covalent bond formation with a second functional group. The group of activating groups which are useful for a carboxylic acid include an amino group simple ester groups, anhydrides, and acid chlorides. The ester groups include alkyl, aryl and alkenyl esters and in particular esters of 4-nitrophenol, N-hydroxysuccinimide, N-hydroxybenzotriazole, and pentafluorophenol. Other activating groups are known to those skilled in the art.

Immobilization:

The choice of functionality used for binding the linker to the solid support will depend on the type of solid support. Conditions for coupling monomers to solid supports through a wide variety of functional groups are known. For example, the carboxyl group of the linker can be activated by converting it to the corresponding —COP group wherein P is an activating group as defined above. This can then be coupled to an amino or hydroxyl group of the solid support.

Protecting Group:

refers to a chemical group protecting the hydrazine group during chemical processing and exhibits the following characteristics: (1) reacts selectively with the desired functionality (—$NHNH_2$) in good yield to give a derivative that is stable to the projected reactions for which protection is desired; (2) can be selectively removed from the derivatized solid support to yield the desired functionality; and (3) is removable in good yields by reagents compatible with the other functional group(s) generated in such projected reactions. Examples of protecting groups can be found in Greene et al. (1991) *Protective Groups in Organic Synthesis*, $2^{nd}$ Ed. (John Wiley & Sons, Inc., New York). Preferred examples are Fmoc, Boc, Trt, Alloc, tBu, Cbz, Bn, $SiR_3$.

N-Terminal Protecting Group:

Amino acids are added in excess to ensure complete coupling during each synthesis step in SPPS, and without N-terminal protection, polymerization of unprotected amino acids could occur, resulting in low peptide yield or synthesis failure. N-terminal protection requires an additional step of removing the protecting group, termed deprotection, prior to the coupling step, creating a repeating design flow as follows:

Protecting group is removed from the trailing amino acids in a deprotection reaction.
Deprotection reagents are washed away to provide a clean coupling environment.
Protected amino acids dissolved in a solvent such as dimethylformamide (DMF) combined with coupling reagents are pumped through the synthesis column.
Coupling reagents are washed away to provide clean deprotection environment Two protecting groups (t-Boc, Fmoc) are commonly used in solid-phase peptide synthesis. Their lability is caused by the carbamate group which readily releases $CO_2$ for an irreversible decoupling step.

Photolytic Cleavage:

Photolytic cleavage is carried out on the hydrazine-functionalized photolabile solid support suspended in appropriate solvents by irradiation for an amount of time to allow the desired cleavage to take place. By changing the time of illumination, from 0 to 100% of the photolabile bonds are cleaved. When the present invention is used as a production platform, it may be desirable to release as much as possible in one step by choosing a sufficiently long time-length of illumination. A quality check of the synthesized compound may be incorporated by release of a small portion before release of the whole lot.

Alternatively, one or more additional linkers may be included in the hydrazine-functionalized photolabile solid support for additional chemical or photolytic cleavage. Such additional linkers comprise base-labile, acid-labile, metal-labile, safety-catch and photolabile linkers, known to persons skilled in the art. Other linkers may also be included in order to optimize and verify the attachment chemistry. Such linkers, such as for example the Rink linker, are known is the art.

The energy needed in the photolysis step to cleave the linker according to the present invention is provided by a 360 nm light source, for example a 400W LED UV-lamp.

For the release of synthesized compounds, e.g. from a library of functionalized small molecules, photolytic cleavage is carried out on a hydrazine-functionalized photolabile solid support. In one example, set up to illustrate the present invention, the hydrazine-functionalized photolabile solid support 9 is suspended in appropriate solvents and cleaved by irradiating for a certain time at room temperature with 360 nm light using a 400W LED UV-lamp.

Spacer:

any flexible part of a molecule providing a connection between the solid support and the photolabile linker. Prior to attachment, it has one reactive functional group appropriate for attachment to the support and one or more optionally protected functional group appropriate for later further functionalization, e.g. amine-protected amino acids with activated carboxylic acid groups.

Peptide/Oligopeptide:

polymer comprising two to 20 naturally occurring amino acids and/or unnatural amino acids. It includes dipeptides, tripeptides, tetrapeptides, pentapeptides, etc.

Polypeptide:

a chain of more than 20 naturally occurring amino acids and/or unnatural amino acids.

Naturally Occurring Amino Acids:

20 canonical α-amino acids (L-form) that aminoacyl-tRNA synthetases use to build proteins in cells: isoleucine, alanine, leucine, asparagine, lysine, aspartate, methionine, cysteine, phenylalanine, glutamate, threonine, glutamine, tryptophan, glycine, valine, proline, serine, tyrosine, arginine and histidine. The D-form of these amino acids may also be found in nature or synthesized.

Unnatural Amino Acids and Amino Acid Derivatives:

Unnatural amino acids are non-proteinogenic amino acids that either occur naturally or are chemically synthesized. Whether utilized as building blocks, conformational constraints, molecular scaffolds or pharmacologically active products, unnatural amino acids represent a nearly infinite array of diverse structural elements for the development of new leads in peptidic and non-peptidic compounds. Due to their seemingly unlimited structural diversity and functional versatility, they are widely used as chiral building blocks and molecular scaffolds in constructing combinatorial libraries.

Drug discovery can benefit from novel, short-chain peptide ligand mimetics (peptidomimetics) with both enhanced biological activity and proteolytic resistance. Used as molecular probes, they can help to better understand the function of biological systems.

Optimized and fine-tuned analogues of peptidic substrates, inhibitors or effectors are also excellent analytical tools and molecular probes for investigating signal transduction pathways or gene regulation.

Examples of commercially available unnatural amino acids (from Sigma-Aldrich) includes: R-amino acids (133 and 12), Homo-amino acids, Proline and Pyruvic acid derivatives, 3-substituted Alanine derivatives, Glycine derivatives, Ring-substituted Phenylalanine and Tyrosine Derivatives, Linear core amino acids, Diamino acids, D-amino acids and N-methyl amino acids.

The Photolabile Hydrazine Linker

In a first aspect of the present invention, it relates to a photolabile hydrazine linker which is suitable for synthesis of peptide hydrazides and dihydropyrano[2,3-c]pyrazoles on a solid support.

The photolabile hydrazine linker has the formula I:

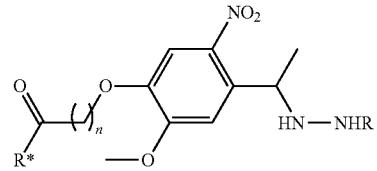

wherein R* is OR', where R' is H, alkyl, substituted alkyl or a bond to a solid support; R is H or a protecting group and n is an integer from 1 to 10.

R* is OH or OR', wherein R' is $C_{1-12}$ alkyl or substituted $C_{1-10}$ alkyl, preferable $C_{1-6}$ alkyl or substituted $C_{1-6}$ alkyl, most preferable $C_{1-4}$ alkyl or substituted $C_{1-4}$ alkyl, such as methyl or ethyl or branched or unbranched propyl or butyl.

The alkyl may be substituted with one or more groups selected from alkyl, aryl, substituted aryl, heteroaryl, substituted heteroaryl. Substituents may be $C_1$-$C_8$ alkyl, $C_1$-$C_8$ alkoxy, halogen, nitrile or nitro R is H or a protecting group, where the protecting group is selected from the group comprising Cbz (Z), multiple substituted methoxy-, nitro-, or chloro-Cbz (including Z(4-MeO), Z(2-NO2), Z(4-NO2), Z(2-Cl), Z(3-Cl), Z(2,4-Cl), and Z(3,5-OMe)), Ddz, Nvoc, Pz, Tmz, Bic, Bpoc, Azoc, iNoc Bocm Cyoc, Tcboc, Adoc, Adpoc, Iboc, Fmoc, Tsoc, Msc, Nsc, Bspoc, Bsmoc, Mspoc, Aloc, Teoc, Tipseoc, Pipoc, Poc, PTnm, Epoc, Mtr, Pmc, Pbf, Trt, 2-Cl-Trt, Dmt, Tmob, Tfa, Tos, o-Nbs, p-Nbs, dNBS, Bts, Nps, Dde, Nde, Trt, Bzl and Acm.

n is an integer from 1 to 10, preferably from 2 to 5, such as from 3 to 5 or n is 3.

The present invention further concerns a method for the synthesis of the photolabile hydrazine linker, wherein R* is OH and R is a protecting group, comprising the steps of a) reacting a compound of formula 2:

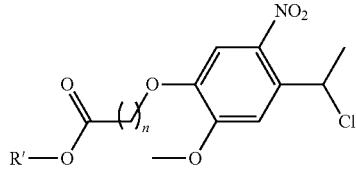

wherein R' is alkyl or substituted alkyl and n is an integer from 1 to 10 with PG-carbazate, where PG is a protecting group to obtain a compound of formula 3:

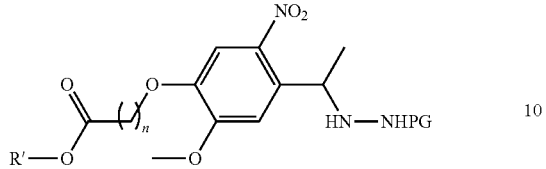

and b), hydrolyzing the compound of formula 3 to obtain a compound of formula 4:

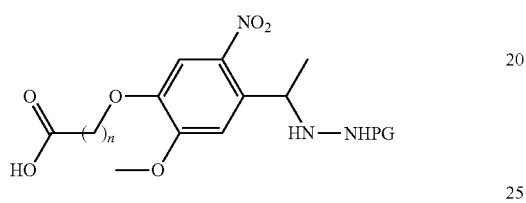

Synthesis of the photolabile hydrazine linker 4 (illustrated with Boc as the hydrazine protecting group and in Schema 1A and R'=ethyl) may commence with the alkylation of acetovanilone 1a with ethyl-4-bromobutyrate followed by nitration, reduction and chlorination (1b-1d) to yield key intermediate benzylic chloride 2 (Qvortrup, K.; Nielsen, T. E. *Chem. Commun.* 2011, 47, 3278-3280) over four steps (Scheme 1A and 1B).

Substitution of chloride with tert-butyl carbazate gave 3 and finally, hydrolysis of the ester moiety afforded the 4-(4-(1-(2-(tert-butoxycarbonyl)hydrazinyl)ethyl)-2-methoxy-5-nitrophenoxy)butanoic acid linker (4) in two steps.

Scheme 1A Synthesis of a Boc-protected hydrazine photolabile linker 4

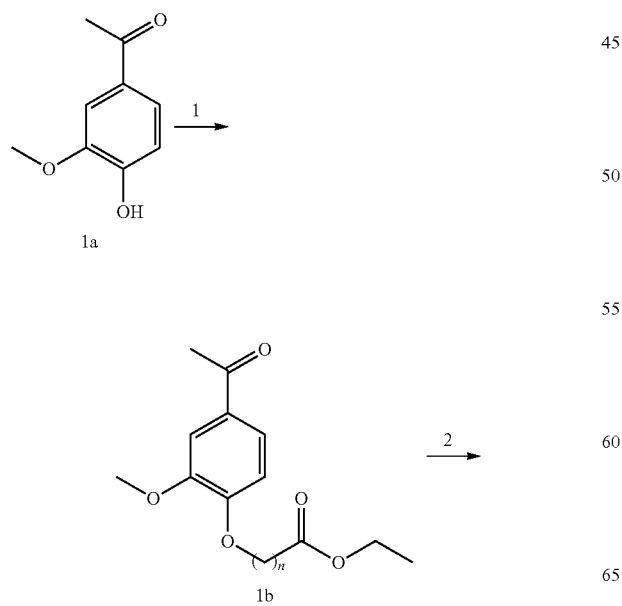

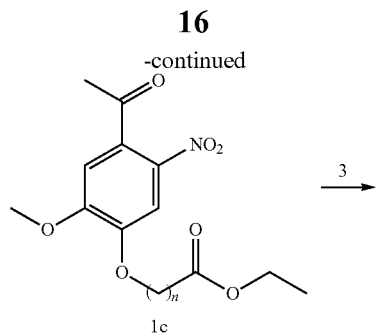

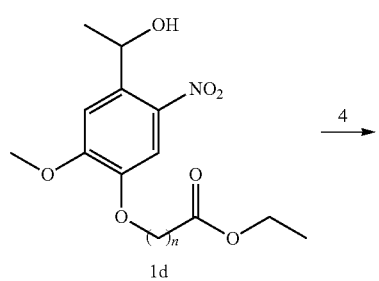

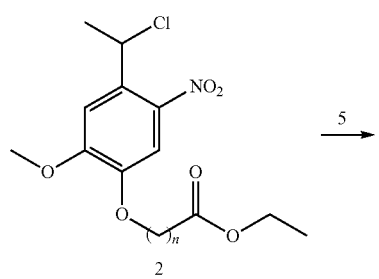

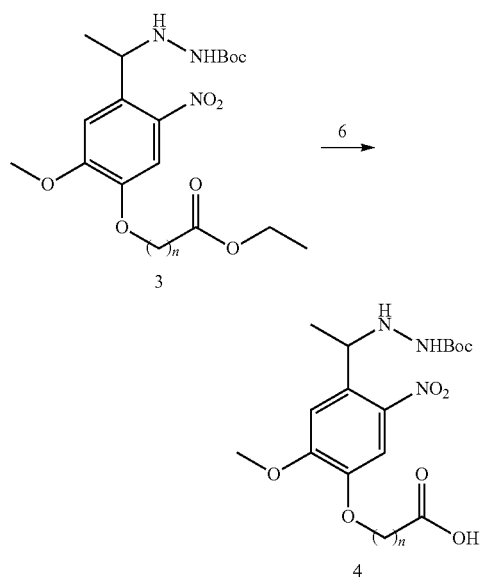

If desired to have a different hydrazine protecting group (PG) in the linker, such a group may be introduced in step 5 instead of Boc to give 3' and 4':

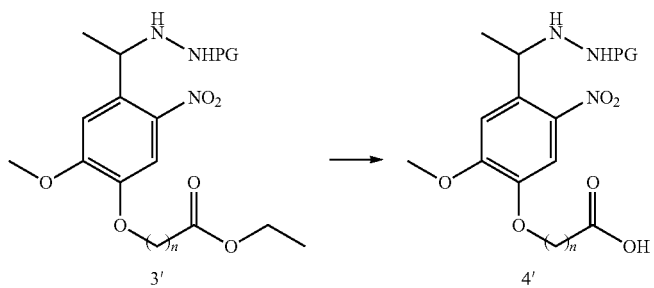

Scheme 1B. Synthesis of a Boc-protected hydrazine photolabile linker 4 where $n = 3$ and R' = ethyl.

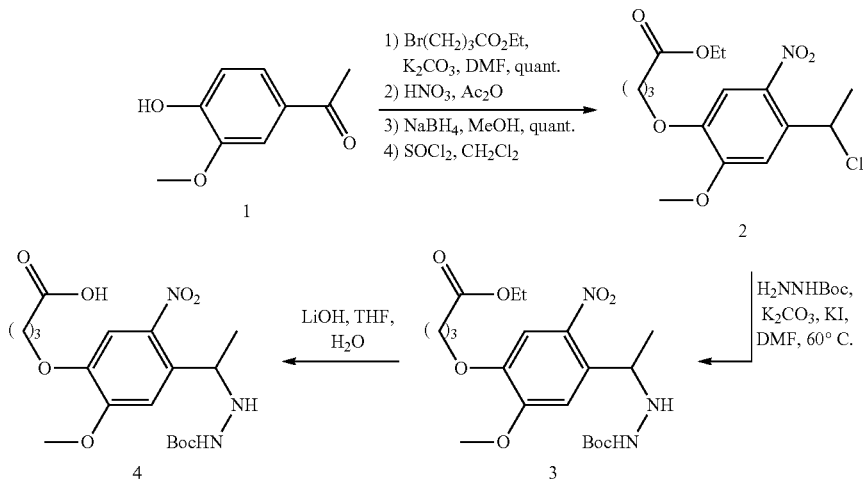

Immobilization of the Protected photolabile Hydrazine Linker

For use of protected hydrazine-functionalized photolabile linkers according to the invention in solid phase synthesis of hydrazine functionalized polymers or heterocyclic compounds, the protected hydrazine-functionalized photolabile linker is immobilized on a solid support by reacting a suitably functionalized solid support with said protected hydrazine-functionalized photolabile linker wherein R* is OH and R is a protecting group to obtain an immobilized protected photolabile hydrazine linker of the following formula:

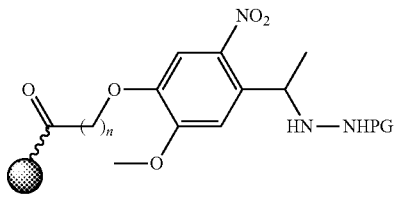

wherein

is a functionalized solid support and PG is a protecting group.

The solid support is functionalized with a group suitable for covalent binding to the protected linker. The functional group may be selected from amino, hydroxy, carboxy, acrylo, maleimido, halo (chloro, bromo, iodo), azido, alkynyl, alkenyl, and nitro.

In the case of using an amino group as the functional group the immobilized protected hydrazine-functionalized photolabile linker has the following formula:

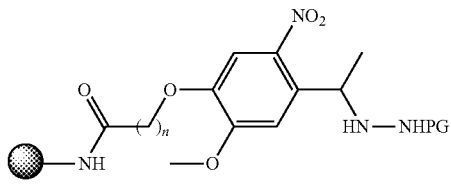

The protecting group used for protecting the hydrazine group during the chemical synthesis is selected from the group comprising Cbz (Z), multiple substituted methoxy-, nitro-, or chloro Cbz (including Z(4-MeO), Z(2-NO2), Z(4-NO2), Z(2-Cl), Z(3-Cl), Z(2,4-Cl), Z(3,5-OMe), Ddz, Nvoc, Pz, Tmz, Bic, Bpoc, Azoc, iNoc Bocm Cyoc, Tcboc, Adoc, Adpoc, Iboc, Fmoc, Tsoc, Msc, Nsc, Bspoc, Bsmoc, Mspoc, Aloc, Teoc, Tipseoc, Pipoc, Poc, PTnm, Epoc, Mtr, Pmc, Pbf, Trt, 2-Cl-Trt, Dmt, Tmob, Tfa, Tos, o-Nbs, p-Nbs, dNBS, Bts, Nps, Dde, Nde, Trt, Bzl and Acm. Other protecting groups would be known by the skilled person.

The functionalized solid support may comprise a further (and orthogonal) linker between the solid support and the functional group provided for binding the protected hydrazine-functionalized photolabile linker according to the present invention. Such additional linkers may be used as spacers and or in order to introduce further cleaving sites as defined above.

The immobilized protected hydrazine-functionalized photolabile linker can be used in synthesis of hydrazine derivatives such as hydrazide peptides and hydrazine functionalized heterocycles. The immobilized linker is prepared for such synthesis by removal of the protecting group from the protected hydrazine-functionalized photolabile linker on the solid support as illustrated in Schema 2.

However, synthetic difficulties were encountered in the removal of the protecting group by conventional methods. Exposing linker construct 5 to standard TFA/CH$_2$Cl$_2$ (1:1) Boc- and Trt-deprotection conditions resulted in formation of the corresponding trifluoroacetyl-functionalized hydrazine photolabile support. However, it was found that a mild TMSOT/2,6-lutidine mediated Boc-deprotection resulted in clean conversion to the desired resin-bound photolabile-hydrazine-derivative 7. Trt-deprotection may be accomplished with dilute HCl in dioxane.

After removal of the protecting group from the linker, the solid support comprising the immobilized hydrazine-functionalized photolabile linker has the following formula:

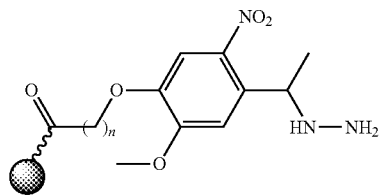

wherein

is a functionalized solid support.

In the case of an amino-functionalized solid support, the solid support comprising the immobilized hydrazine-functionalized photolabile linker has the following formula:

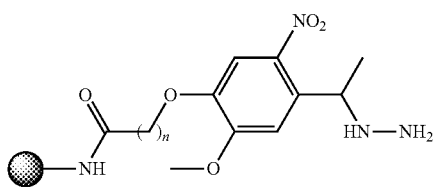

Synthesis of Peptide Hydrazides

The use of the protected photolabile hydrazine linker (4, 4') was explored as a peptide hydrazide-releasing linker as described in general in the following and more specific in the example section. The invention is illustrated with R* being OH or O-ethyl, the protecting group, PG, being Boc and n being 3 Other meanings of R*, PG and n may be applied in a similar way.

An O-(benzotriazol-1-yl)-N,N,N',N'-tetramethyluronium tetrafluoroborate (TBTU)-mediated coupling of 4 to the commercially available amino support (PEGAs$_{00}$) proceeded with full conversion, as judged by conventional Kaiser test, to afford the protected hydrazine-functionalized photolabile support 5.

With an optimized Boc-deprotection protocol at hand, the application of the present linker was examined for the controlled synthesis and photolytic release of hydrazide peptides (Scheme 2). Peptides were synthesized via a Fmoc-strategy using TBTU/NEM-mediated coupling reactions, and the ultimate photolytic cleavage was carried out by irradiating for 60 min at rt with 360 nm light using a 400W LED UV-lamp. To avoid any side reactions associated with the released hydrazide-functionality, including the resin-bound 2-nitrosoacetophenone residues resulting from the photolysis step, the protolytic release was performed in acetone/CH$_3$CN (3:2), releasing the hydrazide group conveniently protected as its acetone hydrazine 8. However, no separate deprotection step is required to free the hydrazide 9, as the acetone rapidly exchanges under the aqueous conditions commonly used in ligation and bioconjugation reactions. Alternatively, co-evaporation of the acetone hydrazine 8 with water cleanly releases the free hydrazide 9 without the need for further post-cleavage purification.

Scheme 2. Synthesis and photolytic release of peptide hydrazides

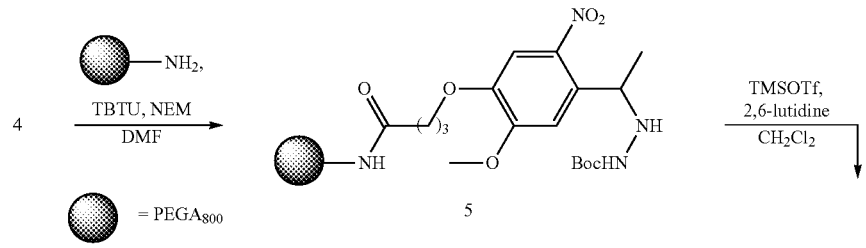

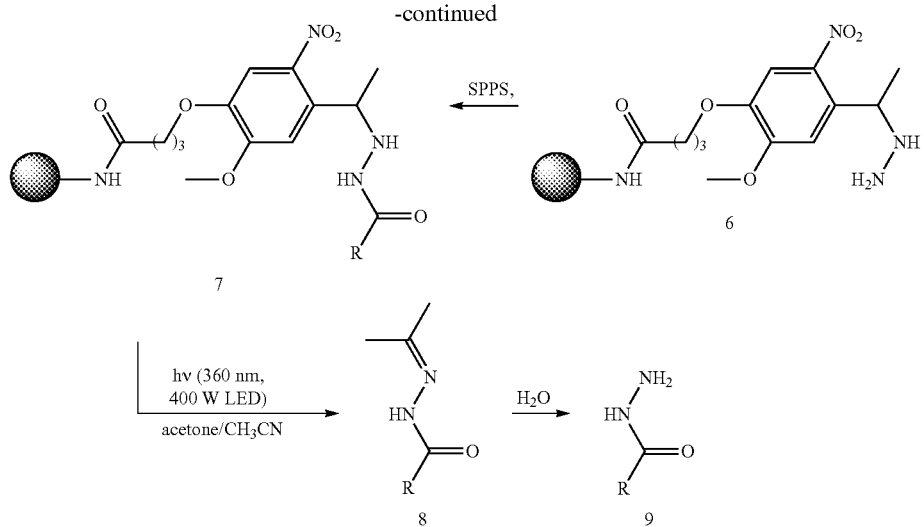

All the 20 naturally occurring amino acid residues (even the side-chain protected analogs) were accepted in the C-terminal position of the peptide-hydrazide (table 1). However, peptide-hydrazides containing C-terminal Glu(tBu) and Asp(tBu) residues should be released just prior to use and/or stored as an acetone-solution, as storage of the free peptide hydrazides over longer time may result in degradation into the corresponding 1,2-diazepane-3,7-diones and tetrahydropyridazine-3,6-diones, respectively.

TABLE 1

Peptide hydrazides (9a-9ad) synthesized according to Scheme 2. Peptide 9n is disclosed as SEQ ID NO: 1 and peptide 9p is disclosed as SEQ ID NO: 2.

| Entry | C-terminal AA | Product | Purity[a] |
|---|---|---|---|
| 9a | Gly | Naph-Phe-Gly-NHNH$_2$ | >95% |
| 9b | Ala | Naph-Ala-NHNH$_2$ | 82% |
| 9c | Val | Boc-Phe-Val-NHNH$_2$ | >95% |
| 9d | Val | Boc-Pro-Phe-Val-NHNH$_2$ | 91% |
| 9e | Leu | Naph-Phe-Leu-NHNH$_2$ | >95% |
| 9f | | Boc-Pro-Phe-Leu-NHNH$_2$ | 82% |
| 9g | | Boc-Ser(Bzl)-Pro-Leu-NHNH$_2$ | 87% |
| 9h | Ile | Boc-Phe-Ala-Ile-NHNH$_2$ | 89% |
| 9i | Met | Boc-Leu-Phe-Met-NHNH$_2$ | 87% |
| 9j | Phe | Naph-Phe-NHNH$_2$ | >95% |
| 9k | | Naph-Leu-Phe-NHNH$_2$ | >95% |
| 9l | Pro | Boc-Phe-Pro-NHNH$_2$ | 85% |
| 9m | | Naph-Phe-Pro-NHNH$_2$ | >95% |
| 9n | | H-Leu-Tyr(tBu)-Arg(Pbf)-Ala-Tyr(tBu)-NHNH$_2$ | >95% |
| 9o | Tyr | Boc-Phe-Leu-Tyr(tBu)-NHNH$_2$ | 88% |
| 9p | | H-Leu-Tyr-Arg-Ala-Tyr-NHNH$_2$ | >95% |
| 9q | Trp | Boc-Phe-Ala-Trp-NHNH$_2$ | >95% |
| 9r | Ser | Boc-Phe-Ser(Bzl)-NHNH$_2$ | >95% |
| 9s | | Naph-Phe-Ser(Bzl)-NHNH$_2$ | >95% |
| 9t | Thr | Boc-Phe-Leu-Thr(tBu)-NHNH$_2$ | 87% |
| 9u | Asn | Boc-Ala-Tyr(tBu)-Asn(Trt)-NHNH$_2$ | 92% |
| 9v | Gln | Boc-Leu-Phe-Gln(Trt)-NHNH$_2$ | 90% |
| 9w | Cys | Boc-Phe-Leu-Cys(StBu)-NHNH$_2$ | >95% |
| 9x | Arg | Boc-Ala-Tyr(tBu)-Arg(Pbf)-NHNH$_2$ | >95% |
| 9y | His | Boc-Val-Phe-His(Boc)-NHNH$_2$ | 90% |
| 9z | | Naph-His-NHNH$_2$ | >95% |
| 9aa | Lys | Naph-Lys(Boc)-NHNH$_2$ | 90% |
| 9ab | | Boc-Ala-Phe-Lys(Boc)-NHNH$_2$ | >95% |
| 9ac | Asp | Boc-Phe-Asp(tBu)-NHNH$_2$ | >95% |
| 9ad | Glu | Boc-Pro-Phe-Glu(tBu)-NHNH$_2$ | 83% |

Ligation of Peptide Hydrazides

The ligation of peptide hydrazides has been shown to be particulary useful for protein chemical synthesis (Fang, G.-M.; Li, Y.-M.; Shen, F.; Huang, Y.-C.; Li, J.-B., Lin, Y.; Cui, H.-K.; Liu, L. Angew. Chem., Int. Ed. 2011, 50, 7645-7649). The application of linker 4 can be utilized in an efficient one-pot strategy, combining solid-phase synthesis, a mild photolytic release and the direct ligation of peptide hydrazides to provide the desired ligation product in high yield. Such a strategy will significantly improve chemical protein synthesis and render it even more complementary to native chemical ligation.

As an example of the applicability of the strategy, the ligation between model peptide hydrazide H-Leu-Tyr-Arg-Ala-Tyr-NHNH$_2$ (SEQ ID NO: 2) (13) and H-Cys-OH was performed. Peptide hydrazide 13 was synthesized from 6 and cleanly released as the acetone hydrazone by light. After removal of the excess acetone (by a stream of nitrogen), an aqueous phosphate (0.2 M) buffer containing 6.0 M guanidinum chloride followed by H-Cys-OH was added (final peptide concentration of 1.5 and 2.0 mM, respectively). At a low pH (3.0) and −10° C., an aqueous NaNO$_2$ solution was added to the ligation mixture. After 20 min, 4-mercaptophenylacetic acid was added, the pH value was adjusted to 7.0 and the reaction left at room temperature for 12 h. Analysis of the reaction by HPLC showed a clean ligation reaction in 85% yield.

Application of the linker for the synthesis of a larger peptide is shown in Scheme 4. In this example, the 10-mer peptide H-Leu-Tyr-Arg-Ala-Tyr-Cys-Lys-Tyr-Met-His-OH (SEQ ID NO: 3) (15) was successfully synthesized by ligating peptide hydrazide 13 with peptide fragment 14 (SEQ ID NO: 4) (Scheme 4). using the one-pot protocol as disclosed above. The ligation proceeded as cleanly as reported by Liu and co-workers to provide the desired product in a high yield (93%).

Scheme 4. Application of linker construct 6 for the synthesis of a 10-mer peptide

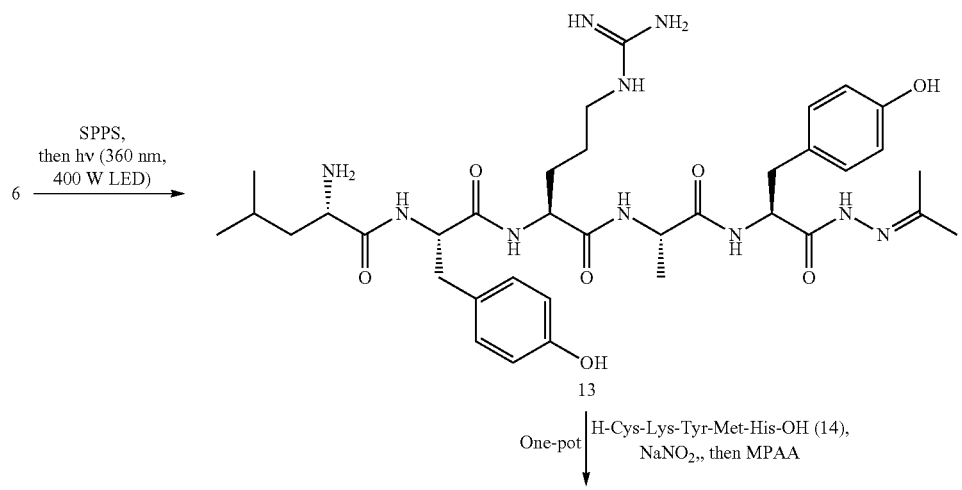

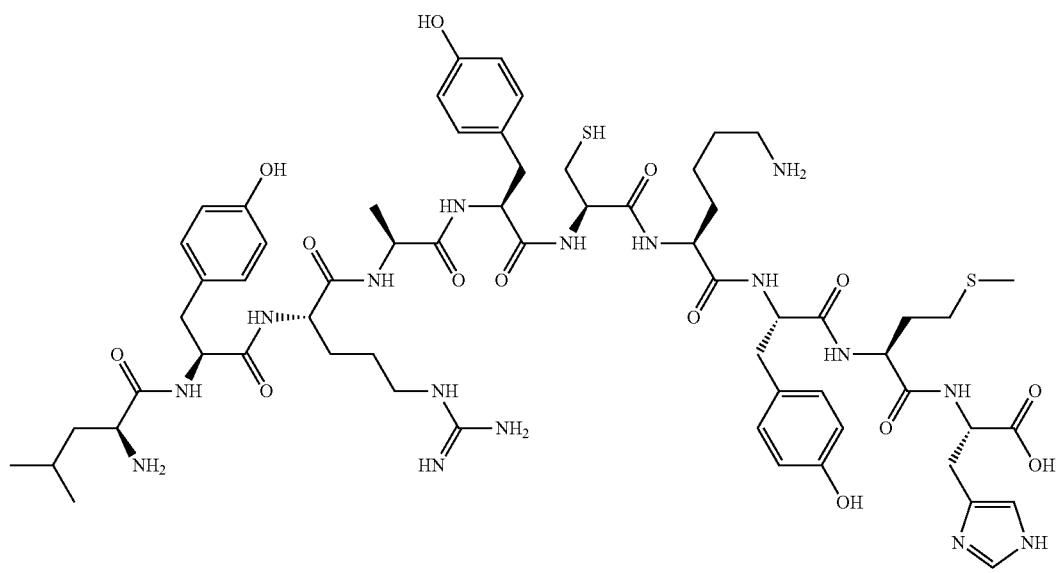

Synthesis of Dihydropyrano[2,3-c]Pyrazoles

To demonstrate the potential of the linker for the generation of more elaborate heterocyclic structures in a combinatorial library format, the use of linker 4 for the synthesis of structurally diverse dihydropyrano[2,3-c]pyrazoles was investigated.

Dihydropyrano[2,3-c]pyrazoles constitute an important class of compounds with a wide range of biological properties, such as anticancer, antimicrobial and antiinflammatory activities. The application of the hydrazine-functionalized photolabile support 6 can be used for the solid-phase synthesis of dihydropyrano[2,3-c]pyrazoles through a two-step procedure as outlined in Scheme 3. Given the large number of commercially available aldehydes and the easy access to 0-keto esters, this protocol represents a synthetically attractive route to dihydropyrano[2,3-c]pyrazole combinatorial libraries with high structural diversity conveniently introduced by substituents at the 3- and 4-position ($R^1$ and $R^3$). $R_1$ is selected from alkyl, substituted alkyl, aryl, substituted aryl, heteroaryl, substituted heteroaryl and $R_3$ is selected from aryl, substituted aryl, heteroaryl, substituted heteroaryl.

Scheme 3. Synthesis and photolytic release of dihydropyrano [2,3-c]pyrazoles.

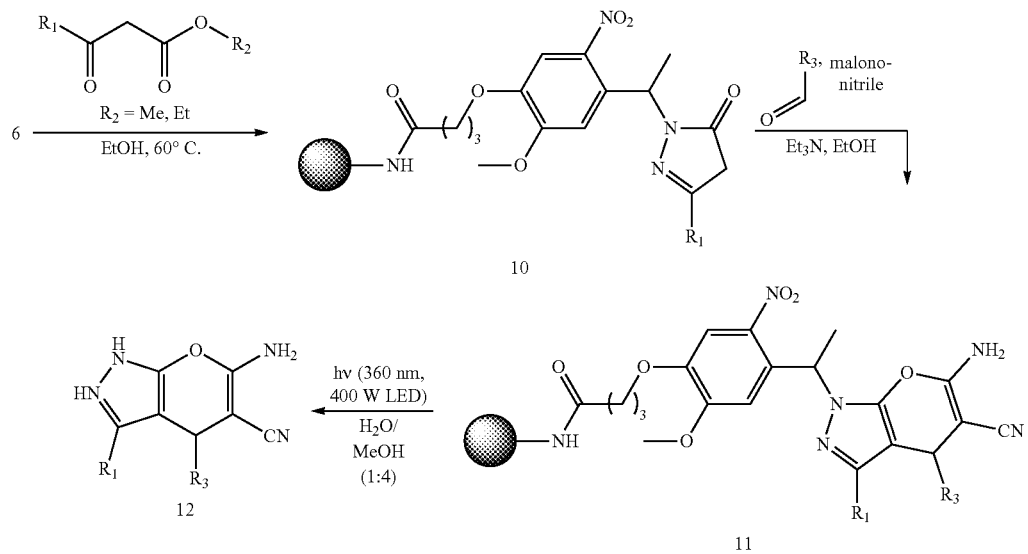

The use of linker 4 (4') for the generation of structural diverse dihydropyrano[2,3-c]pyrazoles was demonstrated by reacting the hydrazine-functionalized photolabile support 6 with the appropriate 3-keto ester under basic conditions to produce the 1H-pyrazol-5(4H)-one derivative 10. Afterwards, 10 was reacted in a three-component base-catalyzed reaction with the corresponding aldehyde and malononitrile in a tandem Michael addition-Thorpe-Ziegler reaction followed by tautomerization to generate the desired dihydropyrano[2,3-c]pyrazole derivative 11. The steps of synthesis and photolytic release of the dihydropyrano[2,3-c]pyrazoles (12a-12h) were very clean (Table 2).

TABLE 2

Dihydropyrano[2,3-c]pyrazole derivatives 12a-12h produced via Scheme 3.

| Entry | Substrate | purity[a] |
|---|---|---|
| 12a | | >95% |
| 12b | | >95% |
| 12c | | >95% |
| 12d | | >95% |
| 12e | | >95% |

TABLE 2-continued

Dihydropyrano[2,3-c]pyrazole derivatives 12a-12h produced via Scheme 3.

| Entry | Substrate | purity[a] |
|---|---|---|
| 12f | | >95% |
| 12g | | >95% |
| 12h | | 90% |

EXAMPLES

General Methods

All reagents used were commercially available. All solvents were of HPLC grade. Solid-phase synthesis was carried out using plastic-syringe techniques. Flat-bottomed PE-syringes were fitted with PPE filters, Teflon® tubing and valves, which allow suction to be applied to the syringes. Acid-mediated release of products was carried out in glass vials. Products were analyzed using a Waters Alliance 2695 HPLC system using Symmetry® C-18 column 3.5 μm, 4.6×75 mm, column temp; 25° C., (1 ml/min.) with detection at 215 nm and 254 nm using a diode array detector. Eluent A (0.1% TFA in $H_2O$) and eluent B (0.1% TFA in acetonitrile) was used with a linear gradient (100% A to 100% B) with a run time of 13 min. Analytical LC-MS analysis was performed on a Waters AQUITY UPLC system equipped with PDA and SQD MS detector; column: AQUITY UPLC BEH C18 1.7 μm, 2.1×50 mm; column temp: 65° C.; solvent A: 0.1% formic acid (aq); solvent B: 0.1% formic acid (acetonitrile); gradient: 5% B to 100% B in 2.4 min, hold for 0.1 min, total run-time ca. 2.6 min. $^1H$ and $^{13}C$ NMR 300 MHz spectra were recorded on a Varian Mercury 300 BB spectrometer at room temperature. All NMR spectra were recorded using $CDCl_3$ or DMSO-$d_6$ as solvents.

Example 1

Linker Synthesis

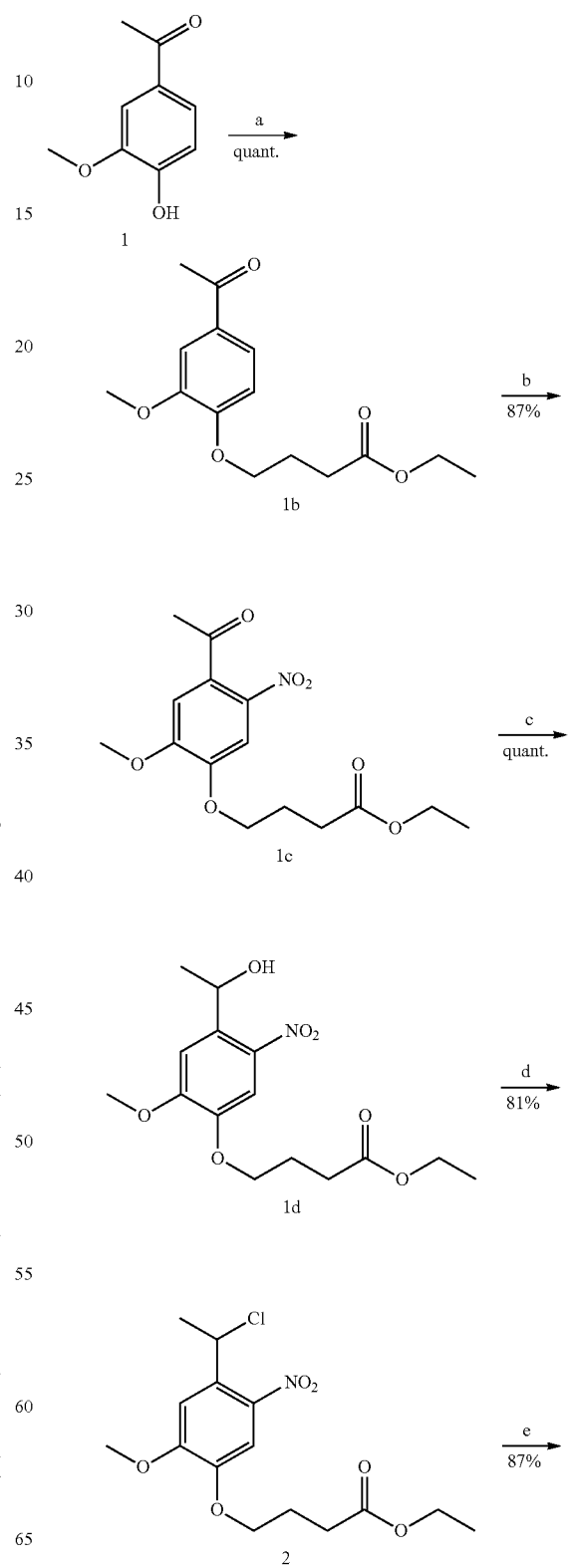

Scheme 1.

-continued

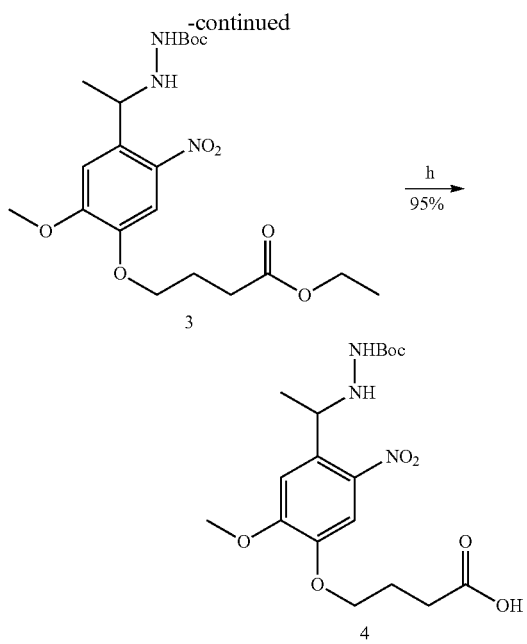

Synthesis of Boc-protected hydrazine-functionalized carboxylic acid linker 4:
a ethyl 4-bromobutyrate, K$_2$CO$_3$, DMF, 60° C.
b HNO$_3$, Ac$_2$O
c NaBH$_4$, MeOH
d SOCl$_2$, CH$_2$Cl$_2$
e tert-Butyl carbazate, K$_2$CO$_3$, KI, DMF
f LiOH, H$_2$O/THF.

Ethyl 4-(4-Acetyl-2-methoxyphenoxy)butanoate (1b).[1]

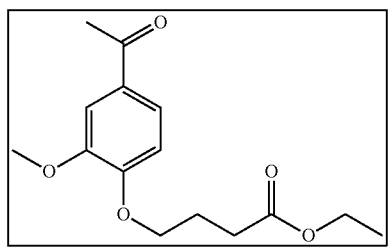 [SMILES: CCOC(=O)CCCOc1ccc(C(C)=O)cc1OC]

To a solution of acetovanillone 1a (35.5 g, 0.21 mol) in DMF (120 mL) was added K$_2$CO$_3$ (44.3 g, 0.32 mol) and ethyl 4-bromobutyrate (31.0 mL, 0.21 mol). The mixture was stirred for 16 hours at rt, then heated for 3 hours at 50° C. After filtration the solution was partitioned between EtOAc and H$_2$O. The organic phase was washed several times with H$_2$O to remove the DMF. The organic phase was dried (MgSO$_4$), filtered and the solvent was removed by rotary evaporation to afford 58.9 g of 1b (quant.) as a white solid.

$^1$H NMR (300 MHz, CDCl$_3$): δ=1.23 (t, J=7.3 Hz, 3H), 2.17 (pentet, J=7.3 Hz, 2H), 2.52 (t, J=7.3 Hz, 2H), 2.53 (s, 3H), 3.88 (s, 3H), 3.87-4.17 (m, 4H), 6.87 (d, 3=8.4 Hz, 1H), 7.47-7.53 (m, 2H); $^{13}$C NMR (75.5 MHz, CDCl$_3$): δ=14.4, 24.5, 26.5, 30.8, 56.2, 60.7, 68.0, 110.6, 111.4, 123.4, 130.7, 149.5, 152.8, 173.3, 196.7; UPLC/MS (ESI) m/z 281.3 [M+H]$^+$.

Ethyl 4-(4-acetyl-2-methoxy-5-nitrophenoxy)butanoate (1c).[1]

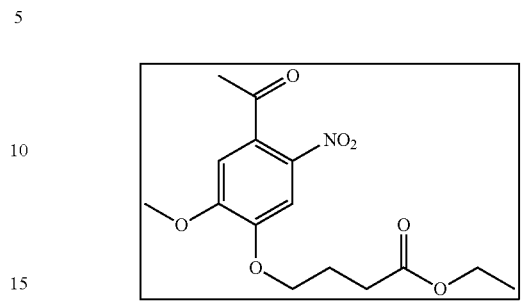

A solution of ketoester 1b (10.0 g, 35.7 mmol) in 30 mL acetic anhydride was slowly added to a solution of 70% HNO$_3$ (200 mL) and acetic anhydride (40 mL) at 0° C. After stirring for 3 h the reaction mixture was poured into ice-cooled water. The precipitate was immediately collected by filtration (we found that leaving the mixture for longer time reduced the yield due to hydrolysis of the ester). The precipitate was washed extensively with water before being dried under vacuum to afford 10.8 g of 1c (82%) as a pale yellow solid.

$^1$H NMR (300 MHz, CDCl$_3$): δ=1.23 (t, J=7.3 Hz, 3H), 2.10 (pentet, J=7.3 Hz, 2H), 2.50 (t, J=7.1 Hz, 2H), 2.51 (s, 3H), 3.83 (s, 3H), 4.03 (t, J=7.3 Hz, 2H), 4.10 (q, 3=7.1 Hz, 2H), 6.95 (s, 1H), 7.57 (s, 1H); $^{13}$C NMR (75.5 MHz, CDCl$_3$): δ=14.3, 24.3, 28.2, 30.4, 55.7, 59.6, 68.4, 108.6, 110.7, 132.8, 138.2, 148.8, 154.3, 173.2, 198.7; UPLC/MS (ESI) m/z 326.3 [M+H]$^+$.

Ethyl 4-(4-(1-hydroxyethyl)-2-methoxy-5-nitrophenoxy)butanoate (1d).[1]

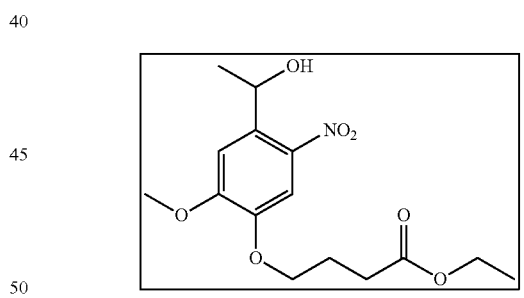

To a solution of 1c (4.00 g, 12.3 mmol) in 300 mL MeOH at 0° C. was slowly added NaBH$_4$ (1.2 g; 31.7 mmol) in portions. After complete addition, the mixture was allowed to reach rt. The reaction was complete after 3 h (as judged by TLC). The reaction was quenched by addition of 200 mL of sat. NH$_4$Cl (aq). The reaction was extracted with EtOAc (400 mL), washed with water (2×300 mL) and brine (300 mL). The organic phase was dried (MgSO$_4$), filtered and the solvent was removed by rotary evaporation to give 4.0 g of 1d (quant.) as a pale yellow solid.

$^1$H-NMR (300 MHz, CDCl$_3$): δ=1.20 (t, J=7.2 Hz, 3H), 1.48 (d, J=7.0 Hz, 3H), 2.10 (pentet, J=7.0 Hz, 2H), 2.47 (t, J=7.1 Hz, 2H), 3.90 (s, 3H), 4.03 (t, J=7.0 Hz, 2H), 4.08 (q, J=7.1 Hz, 2H), 5.48 (q, J=7.0 Hz, 1H), 7.23 (s, 1H), 7.50 (s, 1H); $^{13}$C NMR (75.5 MHz, CDCl$_3$): δ=14.9, 23.9, 27.8, 30.0, 56.0, 61.6, 68.1, 108.5, 109.8, 137.8, 138.5, 147.7, 153.8, 174.6; UPLC/MS (ESI) m/z 328.4 [M+H]$^+$, 310.3 [M−OH]$^+$.

Ethyl 4-(4-(1-chloroethyl)-2-methoxy-5-nitrophenoxy)butanoate (2)

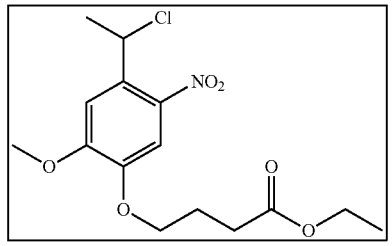 [SMILES: CCOC(=O)CCCOc1cc([N+](=O)[O-])c(C(C)Cl)cc1OC]

To a solution of 1d (4.0 g, 12.3 mmol) in 60 mL CH$_2$Cl$_2$ at 0° C. was added thionyl chloride (20 mL). The reaction was allowed to reach rt. The reaction was complete after 2 h (as judged by TLC). The reaction was evaporated to dryness and co-evaporated several times with toluene (3×20 mL). The residue was passed through a short plug of silica using EtOAc/heptane (1:1) as the eluent. Evaporation of the solvent gave 3.6 g of 1 (79%) as a pale yellow solid.

$^1$H-NMR (300 MHz, CDCl$_3$): δ=1.20 (t, J=7.2 Hz, 3H), 1.80 (d, J=7.1 Hz, 3H), 2.10 (pentet, J=7.0 Hz, 2H), 2.47 (t, J=7.1 Hz, 2H), 3.92 (s, 3H), 4.03-4.13 (m, 4H), 5.86 (q, J=7.1 Hz, 1H), 7.23 (s, 1H), 7.43 (s, 1H); $^{13}$C NMR (75.5 MHz, CDCl$_3$): δ=14.5, 24.4, 27.6, 30.8, 54.0, 56.6, 60.8, 68.5, 108.7, 110.6, 133.0, 140.0, 147.8, 154.0, 173.1; UPLC/MS (ESI) m/z 346.4 [M+H]$^+$, 310.3 [M−Cl]+.

tert-butyl 2-(1-(4-(4-ethoxy-4-oxobutoxy)-5-methoxy-2-nitrophenyl)ethyl)hydrazinecarboxylate (3)

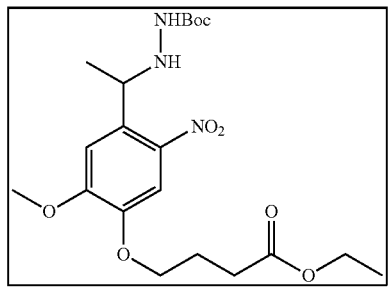 [SMILES: CCOC(=O)CCCOc1cc([N+](=O)[O-])c(C(C)NNC(=O)OC(C)(C)C)cc1OC]

Ethyl 4-(4-(1-chloroethyl)-2-methoxy-5-nitrophenoxy)butanoate (2) (1.49 g, 4.34 mmol) and Boc-carbazate (1.4 g, 5.4 mmol) were dissolved in DMF (16 ml) and K$_2$CO$_3$ (0.6 g, 4.34 mmol) followed by KI (0.033 g, 0.2 mmol were added. The reaction mixture was heated to 60° C. for 12 hours. The reaction was cooled to rt and water was added (100 ml). The mixture was extracted with EtOAc (200 ml) and the organic phase was washed with water (3×150 mL) and brine (150 ml), dried over anhydrous Na$_2$SO$_4$ and concentrated in vacuo. The residue was purified by column chromatography (SiO2, 20-50% EtOAc in heptane) to yield 1.7 g of 3 (87%) as a yellow solid.

$^1$H-NMR (300 MHz, DMSO-d$_7$): δ=1.2 (t, J=7.1 Hz, 3H), 1.25 (d, 3=7.1 Hz, 3H), 1.33 (s, 9H), 1.95 (pentet, J=7.0 Hz, 2H), 2.44 (t, J=7.1 Hz, 2H), 3.93 (s, 3H), 4.02-4.10 (m, 4H), 4.62 (q, 3=7.0 Hz, 1H), 7.48 (s, 1H), 7.50 (s, 1H), 8.16 (s, 1H) (NHNHBoc proton not observed); $^{13}$C NMR (75.5 MHz, CDCl$_3$): δ=13.7, 20.5, 23.6, 27.7, 29.6, 53.1, 55.4, 59.5, 67.3, 77.9, 108.0, 109.9, 140.8, 145.6, 152.7, 155.6, 172.0; UPLC/MS (ESI) m/z 442.2 [MH]+.

HRMS (ESI) calculated for C$_{23}$H$_{25}$N$_2$O$_9$ [M+H]$^-$: m/z=442.2189, found m/z=442.2203.

4-(4-(1-(2-(tert-butoxycarbonyl)hydrazinyl)ethyl)-2-methoxy-5-nitrophenoxy)butanoic acid (4)

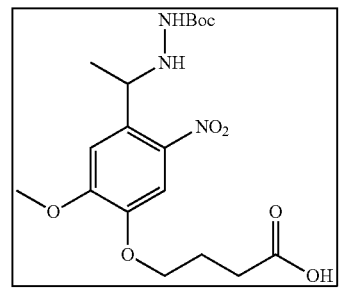 [SMILES: COc1cc(C(C)NNC(=O)OC(C)(C)C)c([N+](=O)[O-])cc1OCCCC(=O)O]

tert-Butyl 2-(1-(4-(4-ethoxy-4-oxobutoxy)-5-methoxy-2-nitrophenyl)ethyl)hydrazinecarboxylate (2) (1.5 g, 3.4 mmol) was dissolved in a mixture of THF (30 ml) and H$_2$O (7.5 mL). LiOH (0.408 g, 17.0 mmol) was added and the reaction mixture was stirred overnight. The reaction was acidified (pH=6) with HCl (1 M, aq.) and the reaction extracted with EtOAc (2×100 ml) and the organic phase was washed with water (3×150 mL) and brine (150 ml), dried over anhydrous Na$_2$SO$_4$ and concentrated in vacuo to give 1.3 g of 4 (95%) as a yellow solid.

$^1$H-NMR (300 MHz, DMSO-d$_7$): δ=1.21 (d, J=7.1 Hz, 3H), 1.33 (s, 9H), 1.95 (pentet, J=7.0 Hz, 2H), 2.39 (t, J=7.1 Hz, 2H), 3.93 (s, 3H), 4.20 (t, 2H), 4.60 (q, J=7.0 Hz, 1H), 7.48 (s, 1H), 7.50 (s, 1H), 8.16 (s, 1H), 11.90 (bs, 1H) (NHNHBoc proton not observed); UPLC/MS (ESI) m/z 414.2 [MH]+.

HRMS (ESI) calculated for C$_{23}$H$_{25}$N$_2$O$_9$ [M+H]$^-$: m/z=414.1876, found m/z=414.1902.

Example 2

Solid-Phase Synthesis

Attachment of Boc-Protected Hydrazine-Linker (4) to Amino-Functionalized PEGA$_{800}$ Beads Boc-protected hydrazine-functionalized carboxylic acid linker (4) was dissolved in DMF, and NEM (4 equiv.) followed by TBTU (2.88 equiv.) were added. The mixture was shaken for 5 min at room temperature before being added to amino-functionalized PEGA$_{800}$ beads pre-swelled in DMF. The mixture was shaken for 2 h at room temperature, followed by washing with DMF (×6), MeOH (×6) and CH$_2$Cl$_2$ (×6) before being lyophilized.

General Procedure for Removal of Hydrazine Boc Protecting Group

Boc deprotection was carried in a 2 mL plastic syringe fitted with a rubber septum. The Boc-protected hydrazine-functionalized resin was swelled in CH$_2$Cl$_2$ and 2,6-lutidine (1.5 M) followed by TMSOTf (1M) added. The mixture was shaken for 15 min followed by washing of the support twice with CH$_2$Cl$_2$. The deprotection procedure was repeated twice. After the last deprotection cycle, the support was washed with washed with CH$_2$Cl$_2$ (×6), DMF (×6) and used directly in the next coupling reaction or washed further with MeOH (×6) and CH$_2$Cl$_2$ (×6) before being lyophilized.

General Procedure for TBTU-Mediated Coupling of Fmoc-Protected Amino Acids to Hydrazine- or Amino-Functionalized PEGA$_{800}$ Beads (Synthesis of 7 10a-m)

The corresponding Fmoc-protected amino acid (3 equiv.) was dissolved in DMF, and NEM (4 equiv.) followed by TBTU (2.88 equiv.) were added. The mixture was shaken for 5 min at room temperature before being added to hydrazine- or amino-functionalized PEGA$_{800}$ beads pre-swelled in DMF. The mixture was shaken for 2 h at room temperature, followed by washing with DMF (×6).

Removal of the Fmoc protecting group was accomplished with 20% piperidine in DMF for 5 min. After washing twice with DMF, the deprotection procedure was repeated, now with a reaction time of 30 min. The support was washed with DMF (×6), MeOH (×6) and CH$_2$Cl$_2$ (×6) before being lyophilized.

General Procedure for TBTU-Mediated Coupling of Boc-Protected Amino Acids to Hydrazine- or Amino-Functionalized PEGA$_{800}$ Beads (Synthesis of 10a-m)

The corresponding Boc-protected amino acid (3 equiv.) (3 equiv.) was dissolved in DMF, and NEM (4 equiv.) followed by TBTU (2.88 equiv.) were added. The mixture was shaken for 5 min at room temperature before being added to hydrazine- or amino-functionalized PEGA$_{800}$ beads pre-swelled in DMF. The mixture was shaken for 2 h at room temperature. The support was washed with DMF (×6), MeOH (×6) and CH$_2$Cl$_2$ (×6).

Removal of the Boc protecting group was accomplished with 50% TFA in CH$_2$Cl$_2$ for 30 min. The support was washed with CH$_2$Cl$_2$ (×6) and DMF (×6) and used directly in the next coupling step or washed further with MeOH (×6) and CH$_2$Cl$_2$ (×6) before being lyophilized.

Example 3

Procedure for Release of Compounds from Photo-Labile Linker for Analytical Purposes Resin sample (5-50 mg) was immersed in CH$_3$CN/acetone (1:4, 0.5-5 mL) in 1-10 mL Petri dishes with an opened top and irradiated from the top with a LED UV-lamp 400W for 2 h. The beads were filtered and washed with CH$_3$CN. The solvent was removed in vacuo and the crude products used directly for analytically purposes (the acetone hydrazones were usually not or only partly observed in HPLC and LCMS experiments due to the acidity of the eluent). However, NMR experiments confirmed the release of hydrazides fully protected as their corresponding acetone hydrazones.

(S)—N-(1-((2-hydrazinyl-2-oxoethyl)amino)-1-oxo-3-phenylpropan-2-yl)-2-naphthamide (9a)

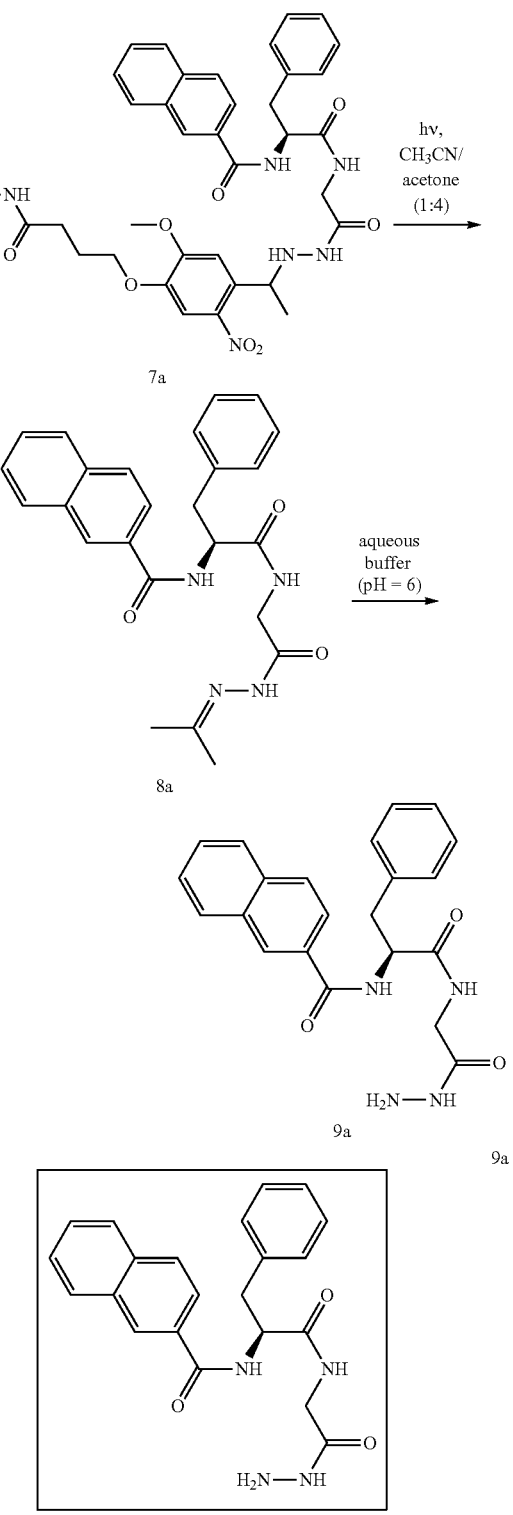

UPLC: Rt=1.41 (1.64 corresponds to acetone hydrazone 8a)

UPLC-MS (ESI) calculated for C$_{23}$H$_{27}$N$_4$O$_3$ [M+H]$^-$: m/z=407.2, found m/z=407.4.

(S)—N-(1-hydrazinyl-1-oxopropan-2-yl)-2-naphthamide (9b)
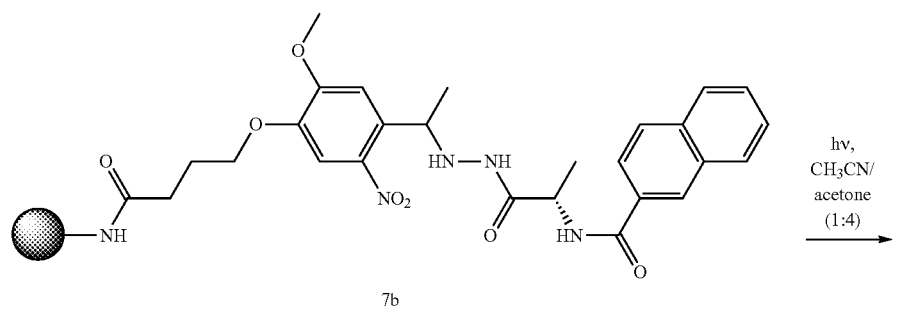
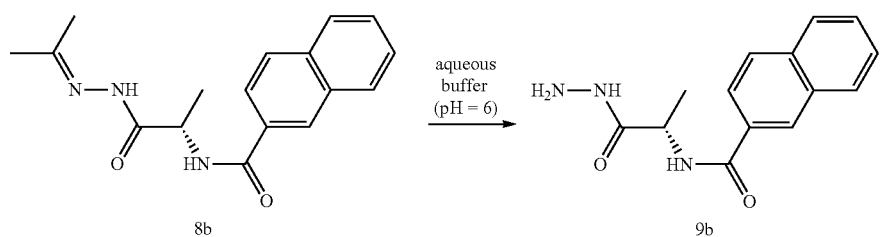
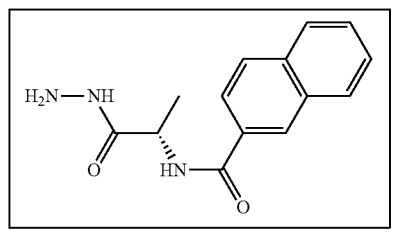
9b
UPLC: Rt=1.41 (1.64 corresponds to acetone hydrazone 8a)
UPLC-MS (ESI) calculated for $C_{14}H_{16}N_3O_2$ [M+H]$^-$: m/z=258.1, found m/z=258.3.

37
tert-butyl ((S)-1-(((S)-1-hydrazinyl-3-methyl-1-oxobutan-2-yl)amino)-1-oxo-3-phenylpropan-2-yl)carbamate (9c)
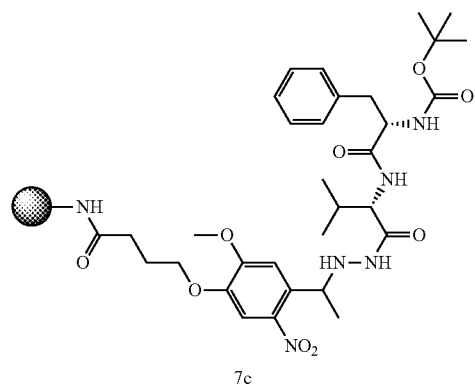
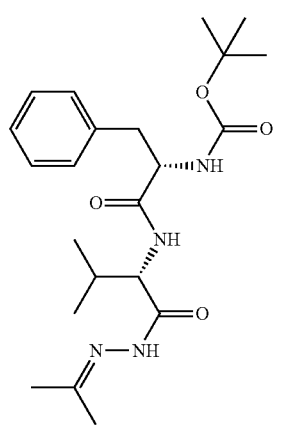
38
-continued
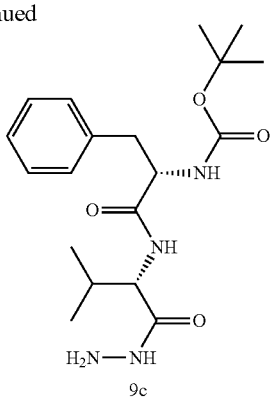
UPLC: Rt=1.41 (1.64 corresponds to acetone hydrazone 8a)
UPLC-MS (ESI) calculated for $C_{23}H_{27}N_4O_3$ [M+H]⁻: m/z=407.2, found m/z=407.4.
(S)-tert-butyl 2-(((S)-1-(((S)-1-hydrazinyl-4-methyl-1-oxopentan-2-yl)amino)-1-oxo-3-phenylpropan-2-yl)carbamoyl)pyrrolidine-1-carboxylate (9d)
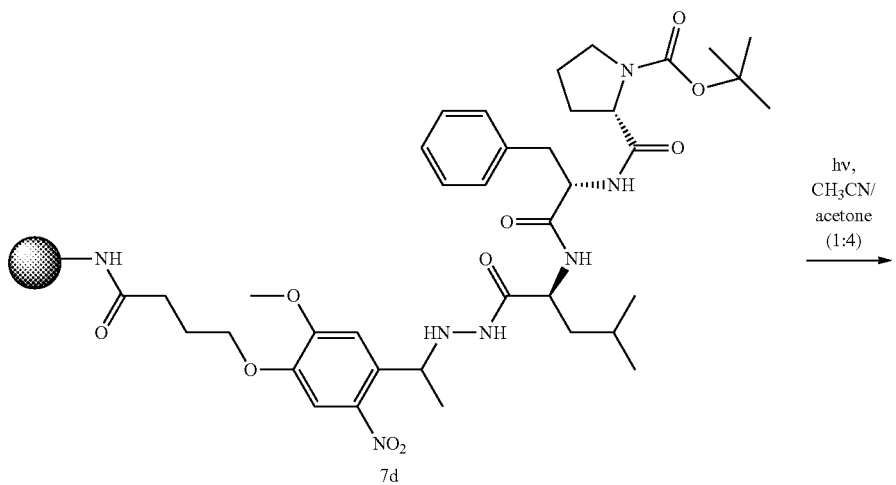

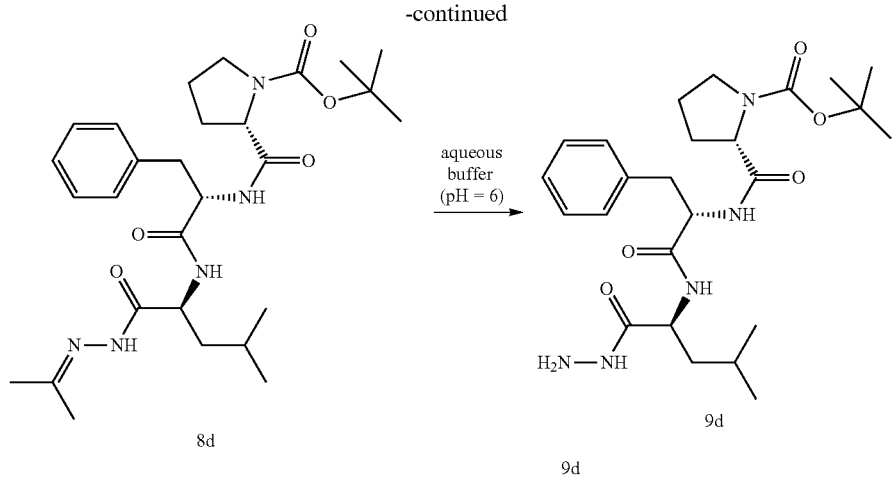
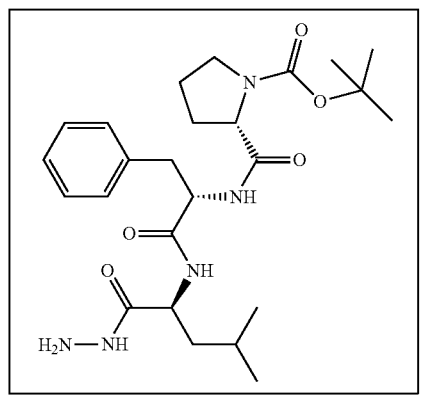
UPLC: Rt=1.58 (1.81 corresponds to acetone hydrazone 8d)
UPLC-MS (ESI) calculated for $C_{25}H_{40}N_5O_5$ [M+H]$^-$: m/z=490.3, found m/z=490.3.
N—((S)-1-(((R)-1-hydrazinyl-4-methyl-1-oxopentan-2-yl)amino)-1-oxo-3-phenylpropan-2-yl)-2-naphthamide (9e)
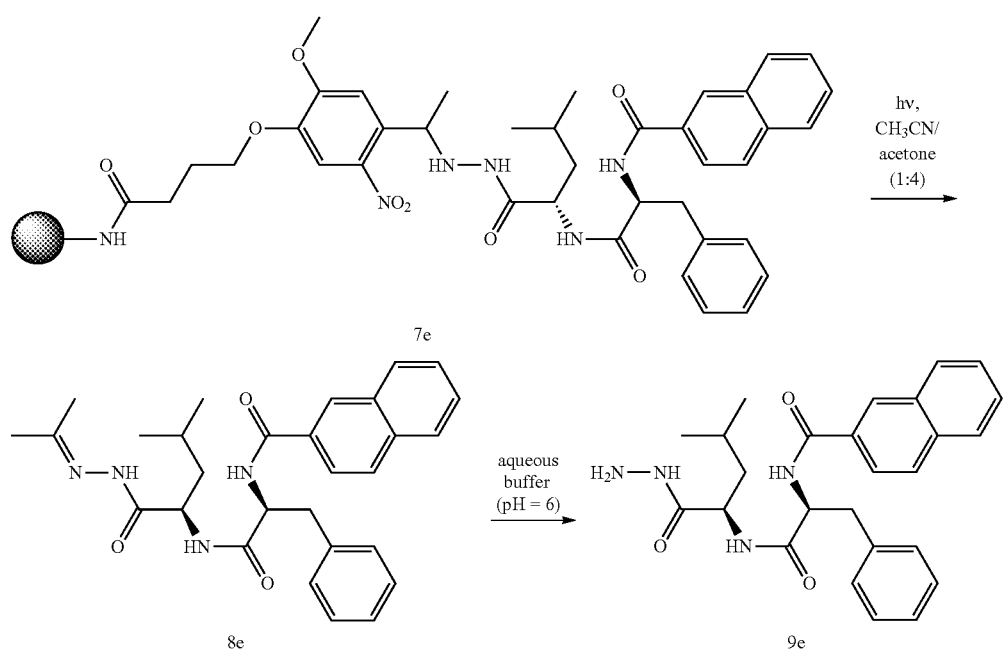

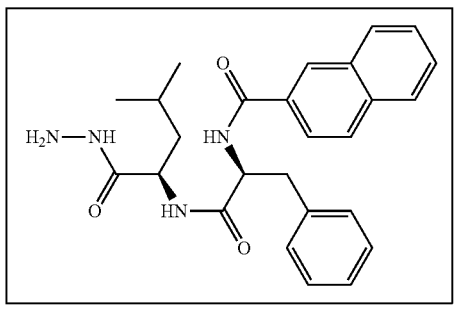
UPLC: Rt=1.73 (2.01 corresponds to acetone hydrazone 8e)
UPLC-MS (ESI) calculated for $C_{26}H_{31}N_4O_3$ [M+H]⁻: m/z=447.2, found m/z=447.2.
tert-butyl ((S)-1-(((R)-1-(((2S,3S)-1-hydrazinyl-3-methyl-1-oxopentan-2-yl)amino)-1-oxopropan-2-yl)amino)-1-oxo-3-phenylpropan-2-yl)carbamate (9h)
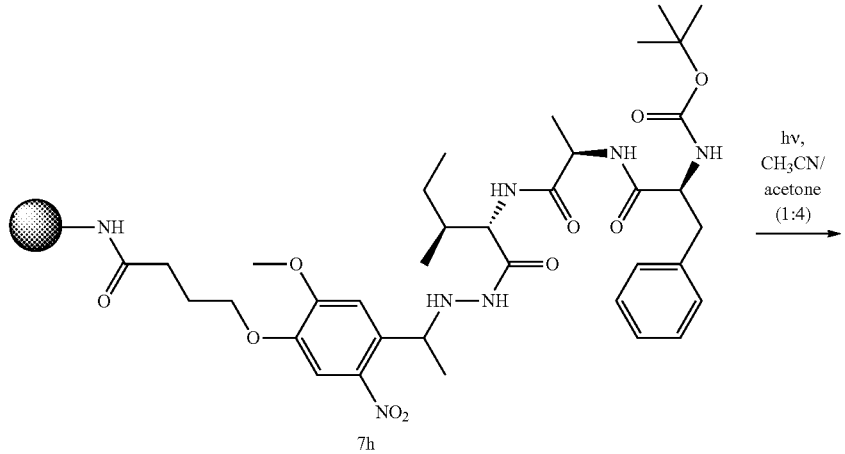
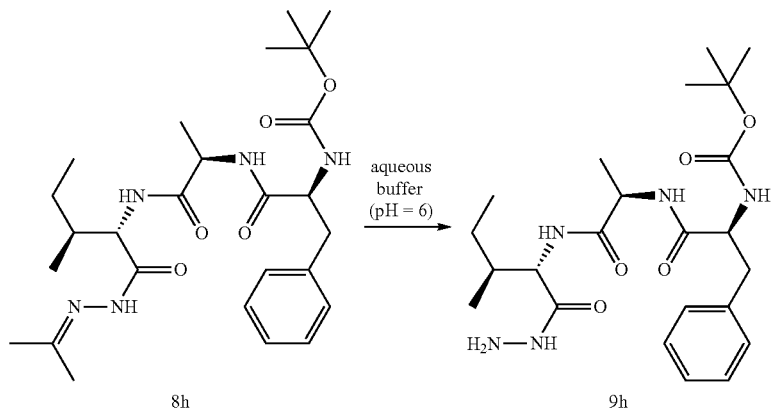

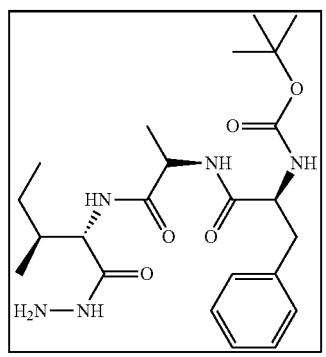
9h
UPLC: Rt=1.50, 1.74 (corresponds to acetone hydrazone 8h)
UPLC-MS (ESI) calculated for $C_{23}H_{36}N_5O_5$ [M+H]$^-$: m/z=464.3, found m/z=464.4.
tert-butyl ((S)-1-(((R)-1-(((S)-1-hydrazinyl-4-(methylthio)-1-oxobutan-2-yl)amino)-1-oxo-3-phenylpropan-2-yl)amino)-4-methyl-1-oxopentan-2-yl)carbamate (9i)
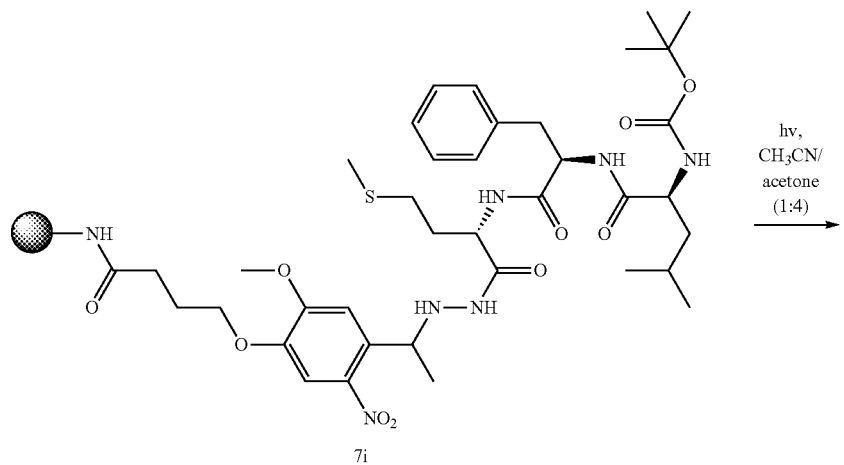
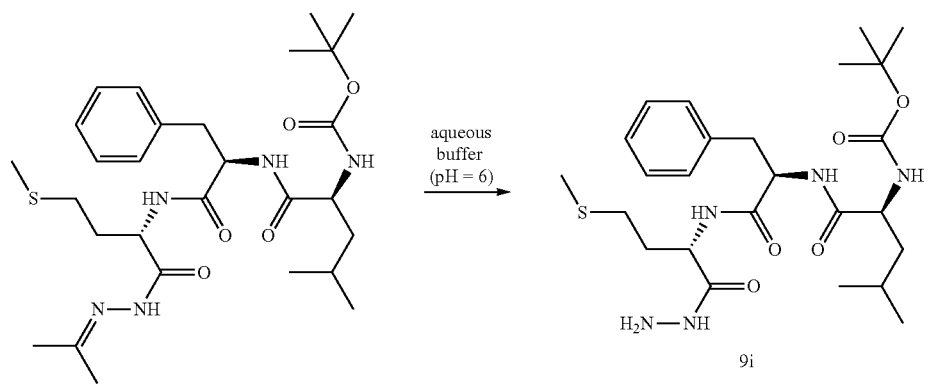

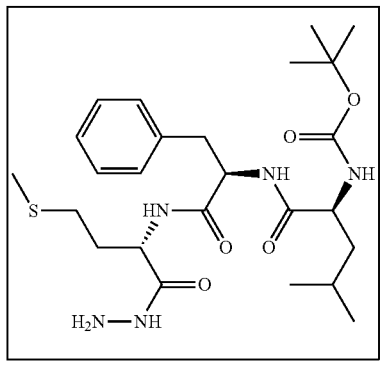
UPLC: Rt=1.58 (1.81 corresponds to acetone hydrazone 8i)
UPLC-MS (ESI) calculated for $C_{25}H_{42}N_5O_5S$ [M+H]$^-$: m/z=524.3, found m/z=524.3.
(S)—N-(1-oxo-3-phenyl-1-(2-(propan-2-ylidene)hydrazinyl)propan-2-yl)-2-naphthamide (9j)
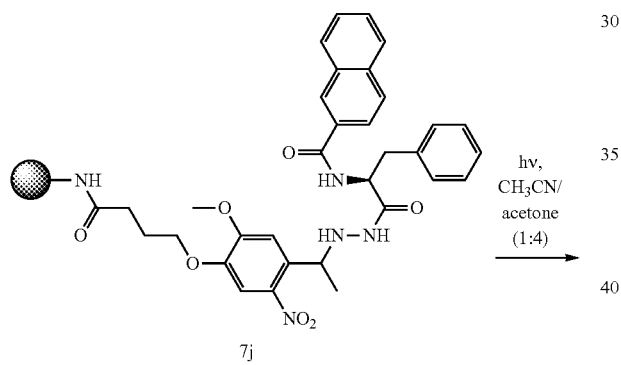
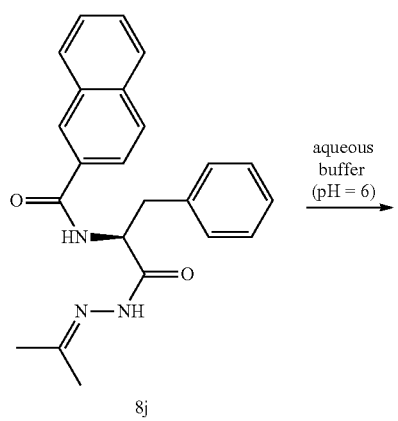
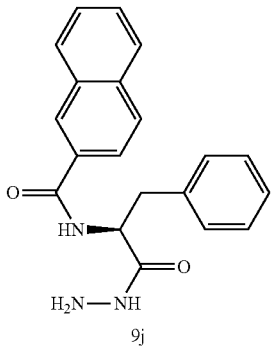
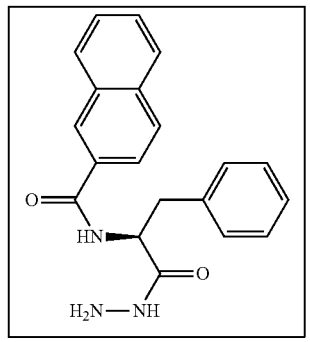
UPLC: Rt=1.47, 1.71 (corresponds to acetone hydrazone 8j)
UPLC-MS (ESI) calculated for $C_{20}H_{20}N_3O_2$ [M+H]$^-$: m/z=334.2, found m/z=334.3.

47
N—((S)-1-(((S)-1-hydrazinyl-1-oxo-3-phenylpropan-2-yl)amino)-4-methyl-1-oxopentan-2-yl)-2-naphthamide (9k)
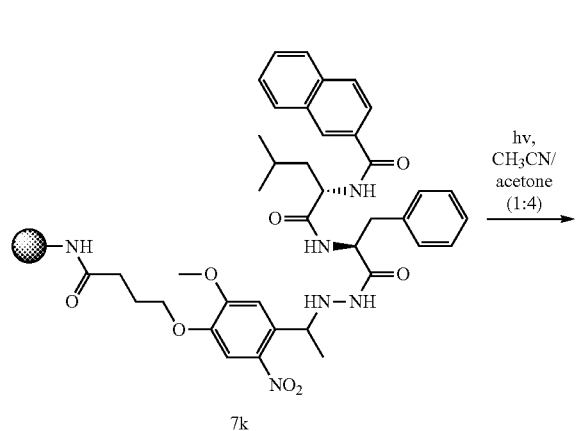
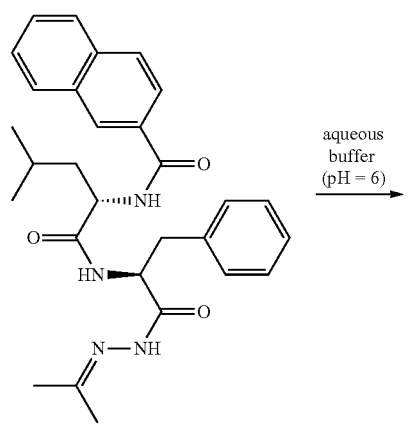
48
-continued
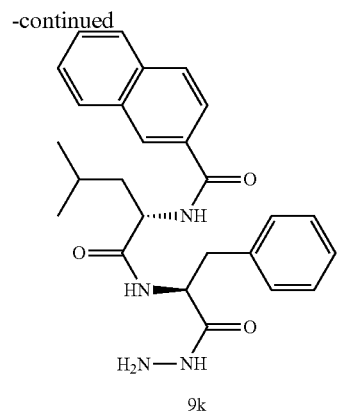
UPLC: Rt=1.74. 198 (corresponds to acetone hydrazone 8k)
UPLC-MS (ESI) calculated for $C_{26}H_{31}N_4O_3$ [M+H]$^-$: m/z=447.2, found m/z=447.3.
tert-butyl ((S)-1-((S)-2-(hydrazinecarbonyl)pyrrolidin-1-yl)-1-oxo-3-phenylpropan-2-yl)carbamate (9l)
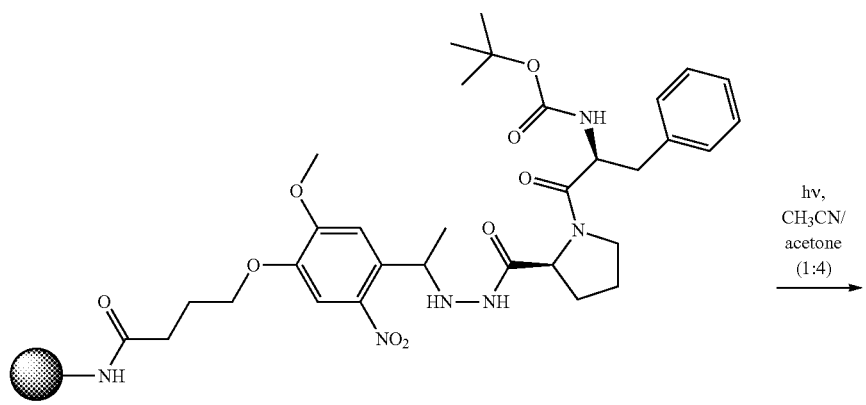

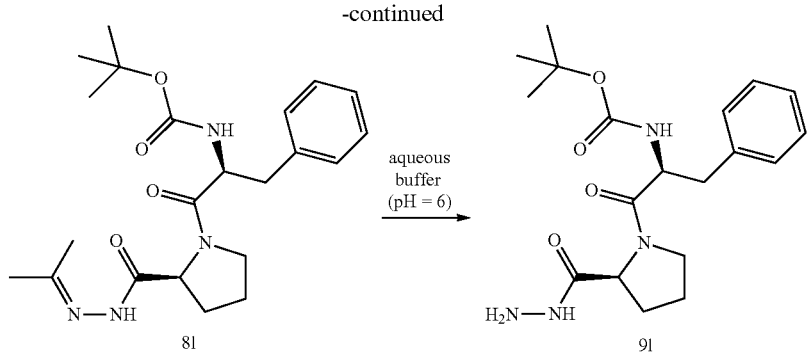
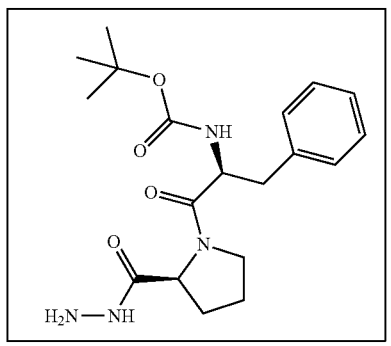
91
UPLC: Rt=1.74. 198 (corresponds to acetone hydrazone 81)
UPLC-MS (ESI) calculated for $C_{26}H_{31}N_4O_3$ [M+H]$^-$: m/z=377.2, found m/z=377.3.
N—((S)-1-((S)-2-(hydrazinecarbonyl)pyrrolidin-1-yl)-1-oxo-3-phenylpropan-2-yl)-2-naphthamide (9m)
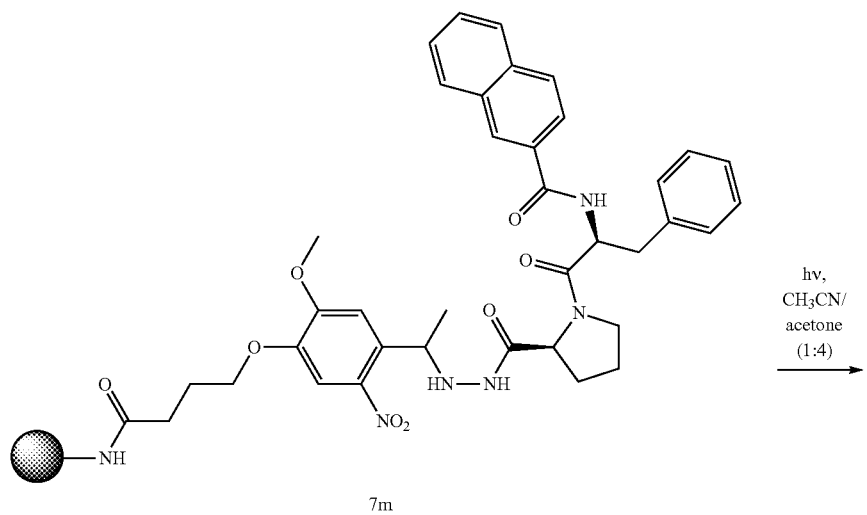

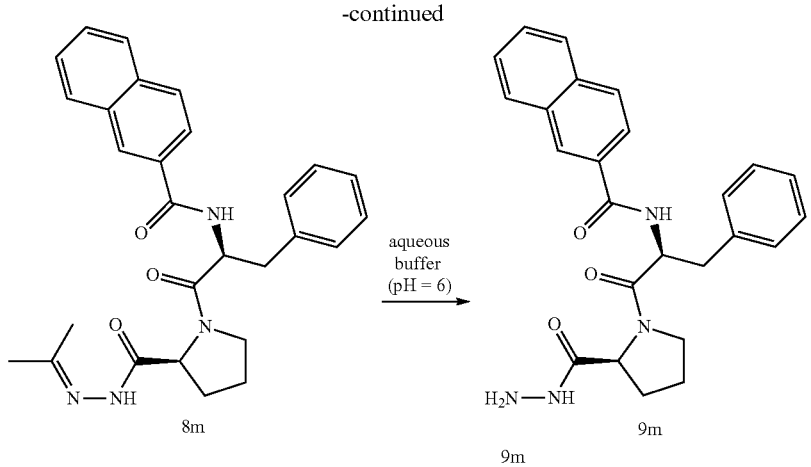
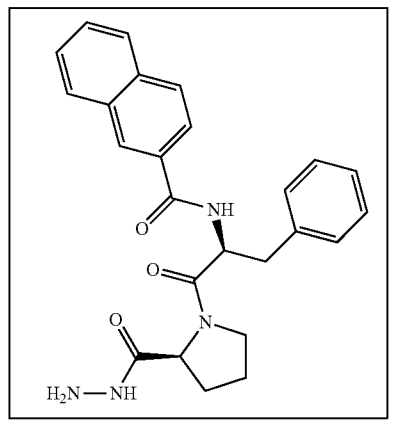
UPLC: Rt=1.50, 1.77 (corresponds to acetone hydrazone 8m)
UPLC-MS (ESI) calculated for $C_{25}H_{27}N_4O_3$ [M+H]⁻: m/z=431.2, found m/z=431.3.
tert-butyl ((S)-1-(((S)-1-(((S)-3-(4-(tert-butoxy)phenyl)-1-hydrazinyl-1-oxopropan-2-yl)amino)-4-methyl-1-oxopentan-2-yl)amino)-1-oxo-3-phenylpropan-2-yl)carbamate, BocPhe-Leu-Tyr(tBu)-NHNH₂ (9o)
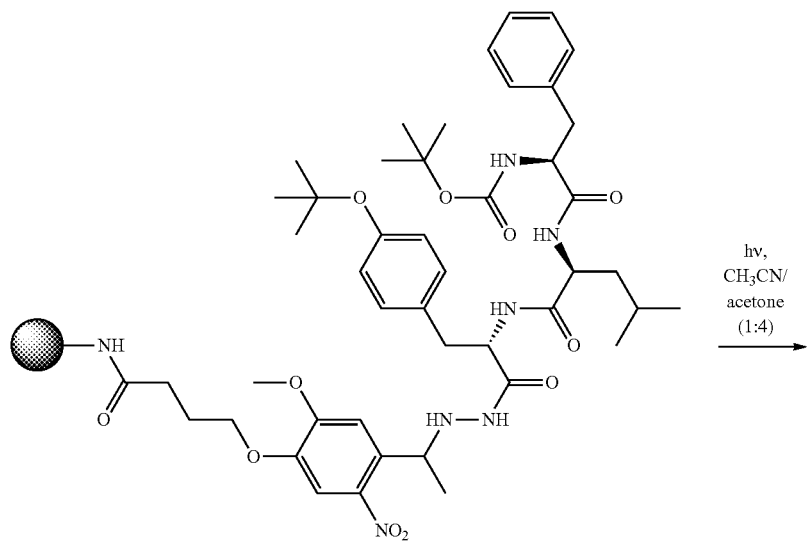

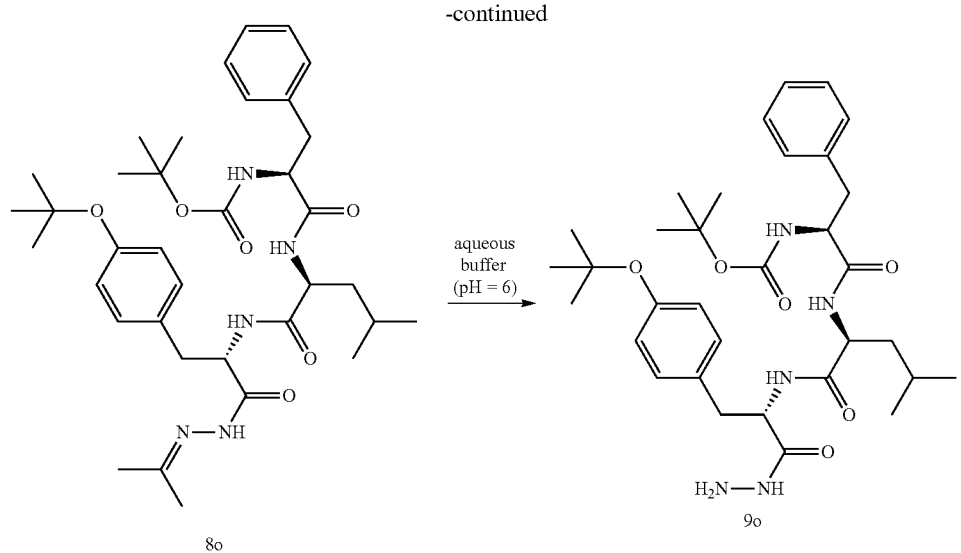
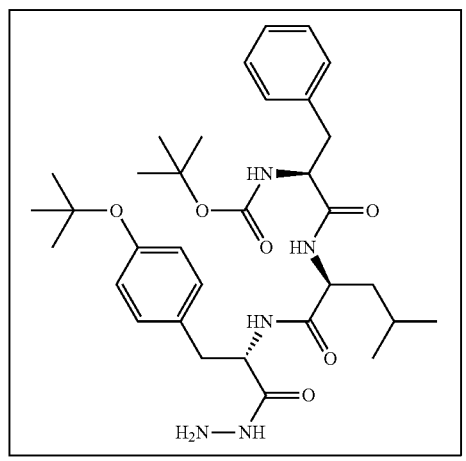
UPLC: Rt=2.07, 2.26 (corresponds to acetone hydrazone 8o)
UPLC-MS (ESI) calculated for $C_{33}H_{50}N_5O_6$ [M+H]$^-$: m/z=612.4, found m/z=612.4.

tert-butyl ((S)-1-(((R)-1-(((S)-1-hydrazinyl-3-(1H-indol-3-yl)-1-oxopropan-2-yl)amino)-1-oxopropan-2-yl)amino)-1-oxo-3-phenylpropan-2-yl)carbamate, Boc-Phe-Ala-Trp-NHNH₂ (9q)
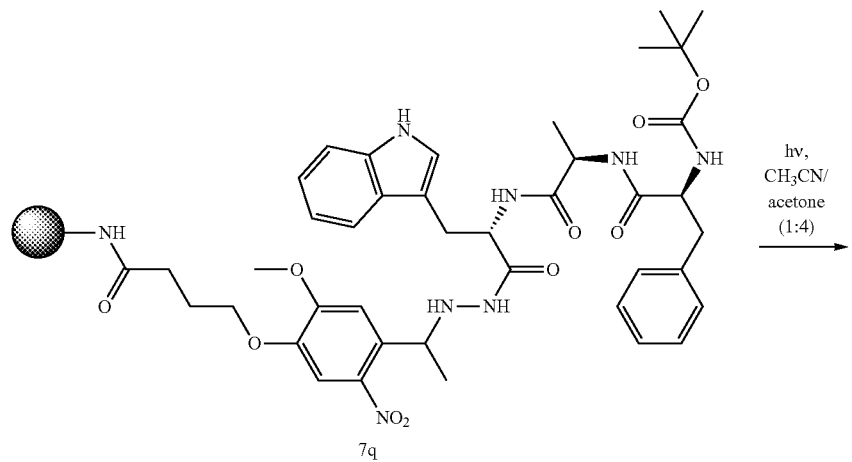
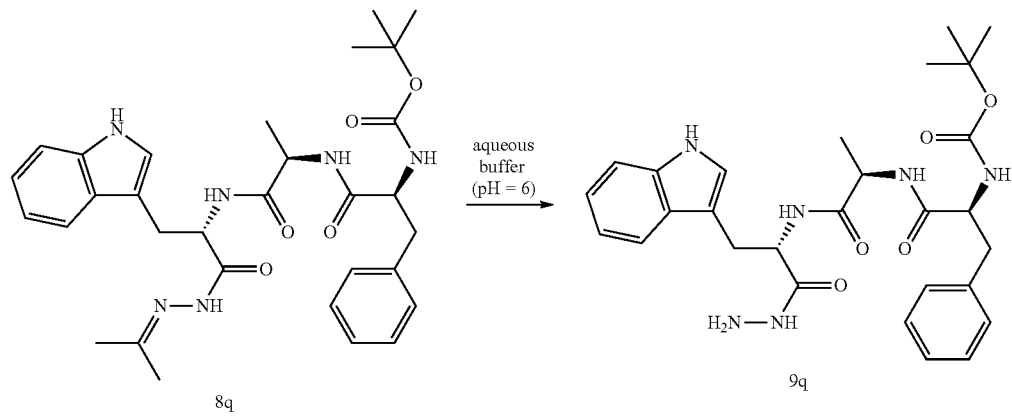
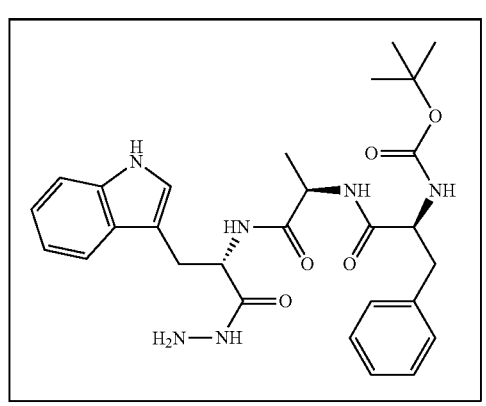
UPLC: Rt=2.07, 2.26 (corresponds to acetone hydrazone 8q)
UPLC-MS (ESI) calculated for $C_{28}H_{37}N_6O_5$ [M+H]⁻: m/z=537.3, found m/z=537.3.

tert-butyl ((S)-1-(((S)-3-(benzyloxy)-1-hydrazinyl-1-oxopropan-2-yl)amino)-1-oxo-3-phenylpropan-2-yl)carbamate, BocPhe-Ser(Bzl)-NHNH₂ (9r)
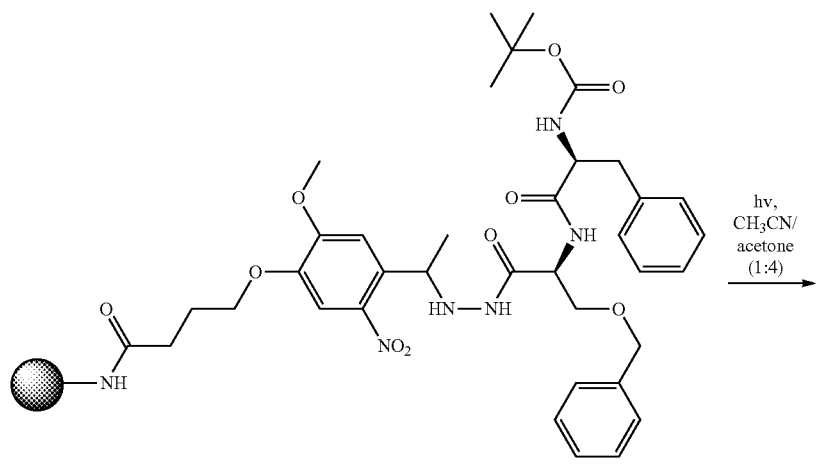
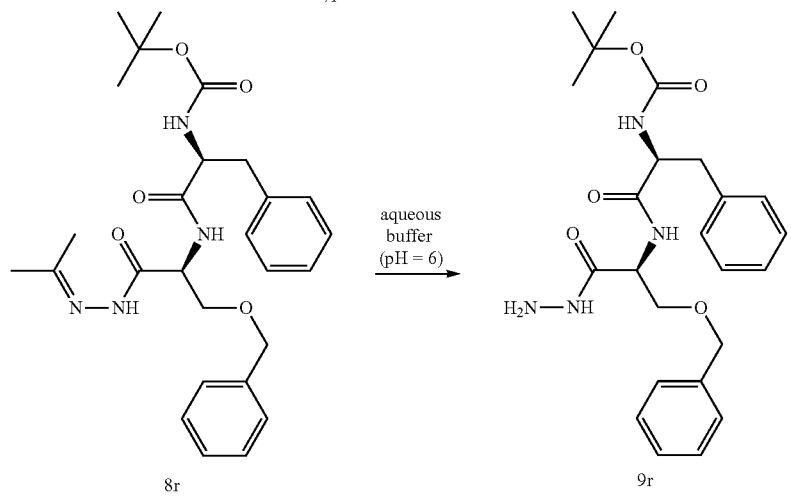
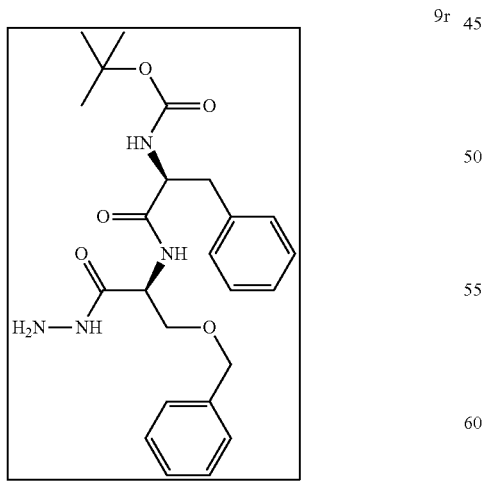
UPLC: Rt=1.72, 2.01 (corresponds to acetone hydrazone 8r)
UPLC-MS (ESI) calculated for $C_{24}H_{33}N_4O_5$ [M+H]⁻: m/z=457.3, found m/z=457.3.

N—((S)-1-(((S)-3-(benzyloxy)-1-hydrazinyl-1-oxo-propan-2-yl)amino)-1-oxo-3-phenylpropan-2-yl)-2-naphthamide, Naph-Phe-Ser(Bzl)-NHNH₂ (9s)
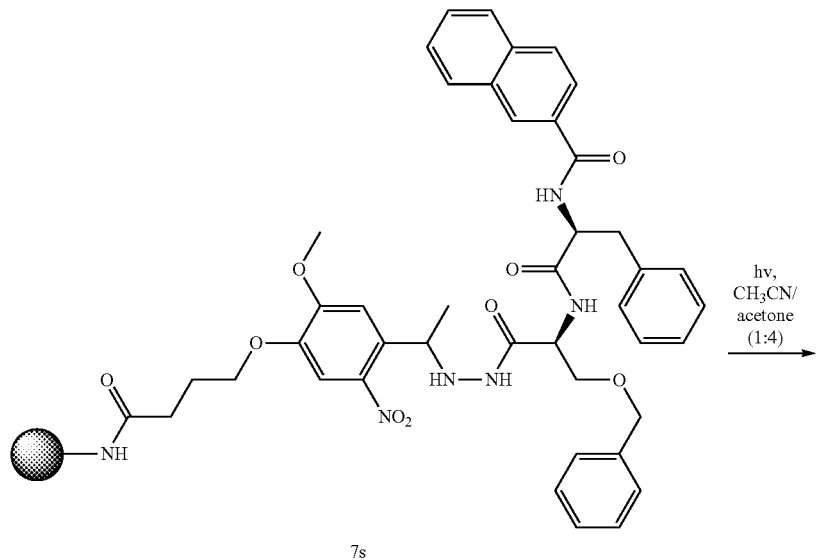
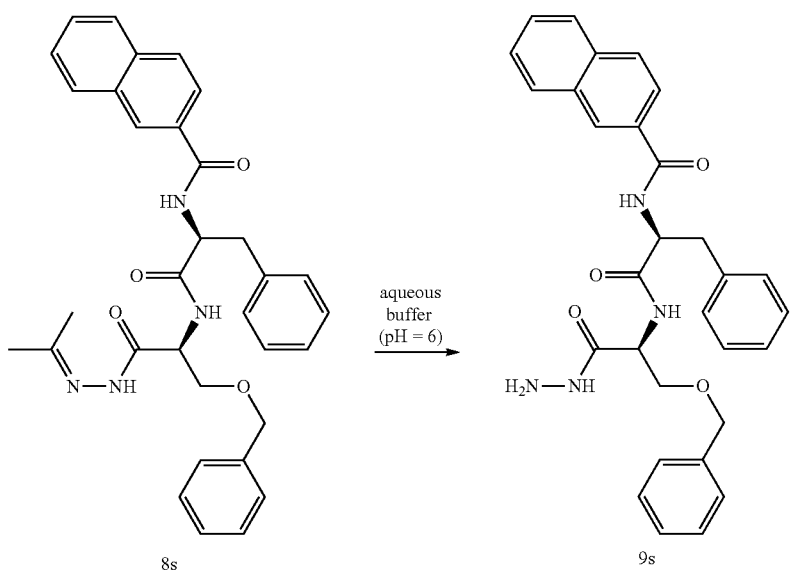

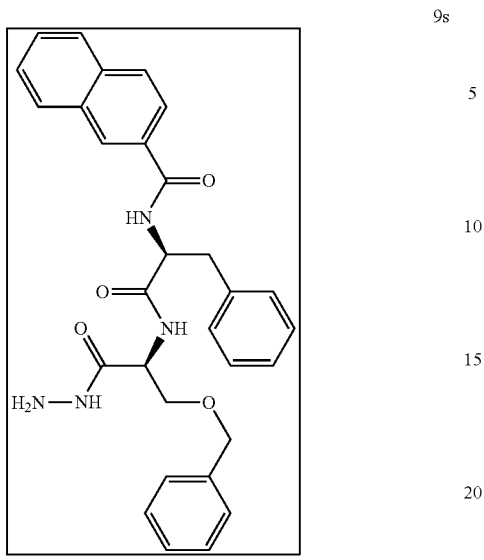
9s
UPLC: Rt=1.82, 2.03 (corresponds to acetone hydrazone 8s)
UPLC-MS (ESI) calculated for $C_{30}H_{31}N_4O_4$ [M+H]$^-$: m/z=511.1, found m/z=511.3.
tert-butyl ((S)-1-(((S)-1-(((2S,3R)-3-(tert-butoxy)-1-hydrazinyl-1-oxobutan-2-yl)amino)-4-methyl-1-oxopentan-2-yl)amino)-1-oxo-3-phenylpropan-2-yl)carbamate, BocPhe-Leu-Thr(tBu)-NHNH$_2$ (9t)
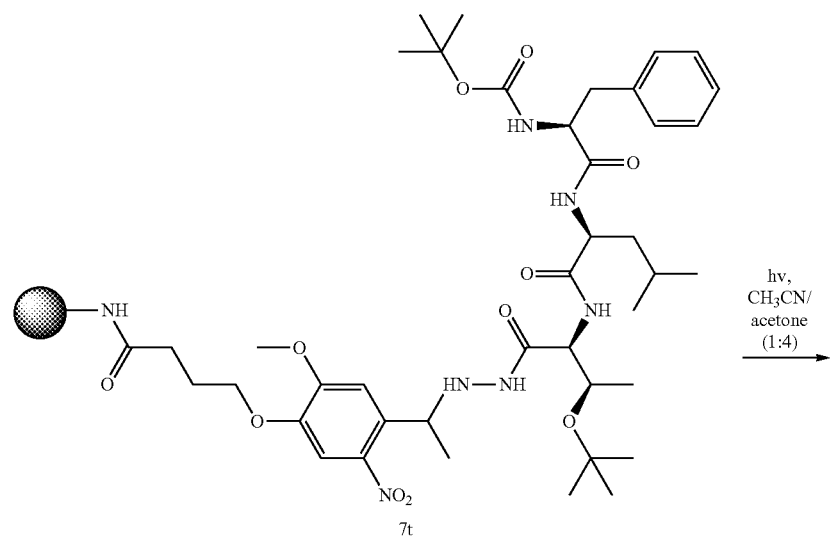
7t

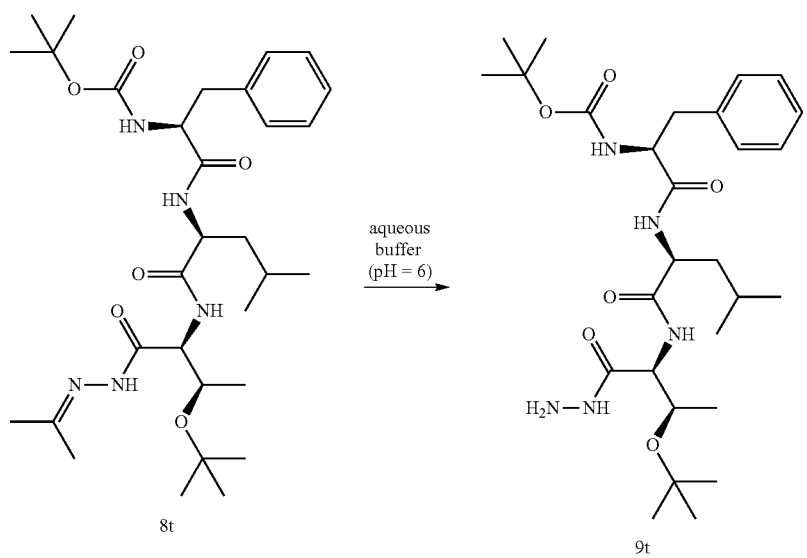
UPLC: Rt=1.92, 2.18 (corresponds to acetone hydrazone 8t)
UPLC-MS (ESI) calculated for $C_{28}H_{48}N_5O_6$ [M+H]$^-$: m/z=550.4, found m/z=550.4.

tert-butyl ((S)-1-(((S)-3-(4-(tert-butoxy)phenyl)-1-(((S)-1-hydrazinyl-1,4-dioxo-4-(tritylamino)butan-2-yl)amino)-1-oxopropan-2-yl)amino)-1-oxopropan-2-yl)carbamate, Boc-Ala-Tyr(tBu)-Asn(Trt)-NHNH₂ (9u)
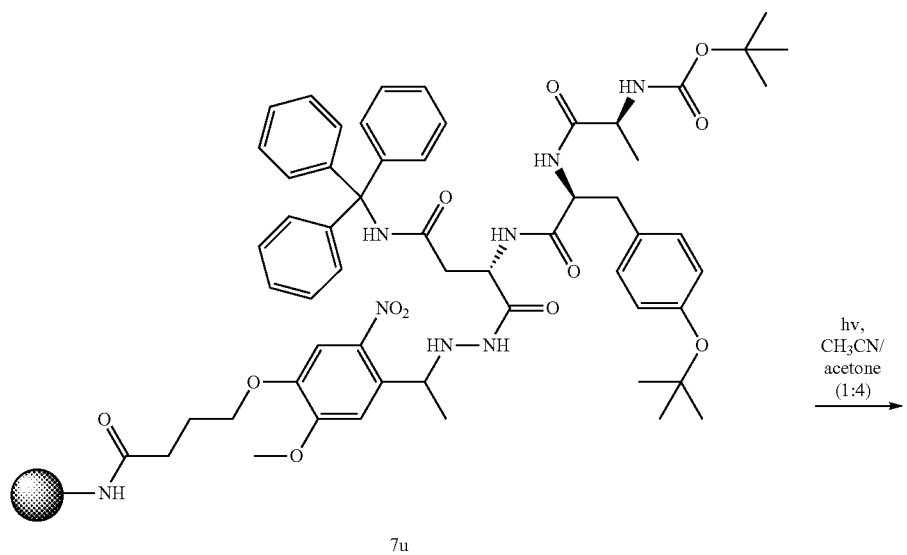
7u
hv, CH₃CN/acetone (1:4) →
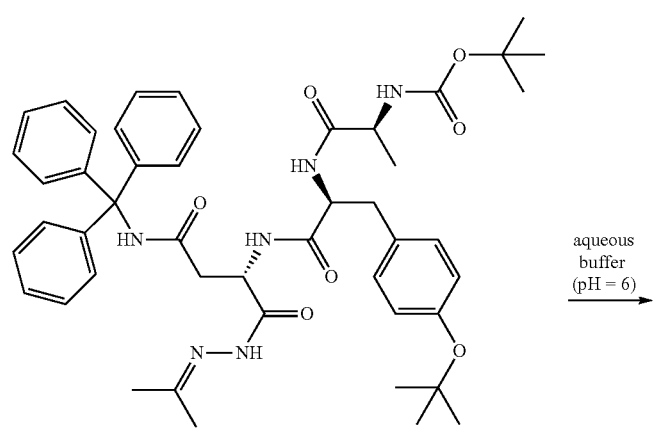
8u
aqueous buffer (pH = 6) →
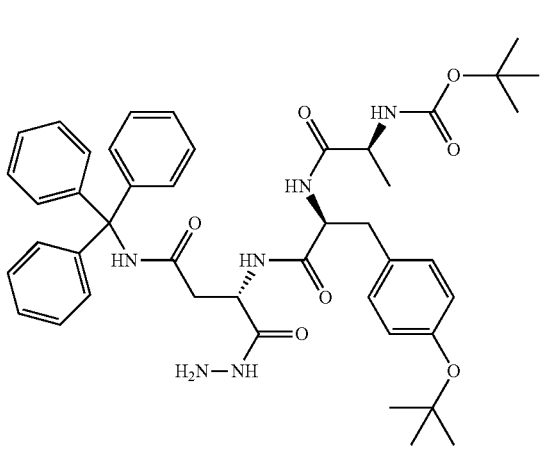
9u

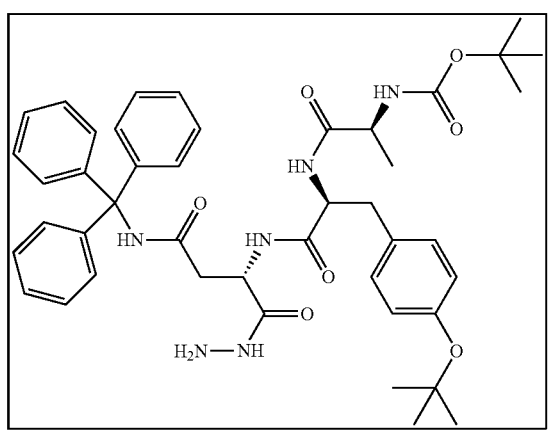
9u
UPLC: Rt=2.32, 2.47 (corresponds to acetone hydrazone 8u)
UPLC-MS (ESI) calculated for $C_{44}H_{55}N_6O_7$ [M+H]$^-$: m/z=779.4, found m/z=779.5 tert-butyl ((R)-1-(((R)-1-(((R)-1-hydrazinyl-1,5-dioxo-5-(tritylamino)pentan-2-yl)amino)-1-oxo-3-phenylpropan-2-yl)amino)-4-methyl-1-oxopentan-2-yl)carbamate, Boc-Leu-Phe-Gln(Trt)-NHNH$_2$ (9v)
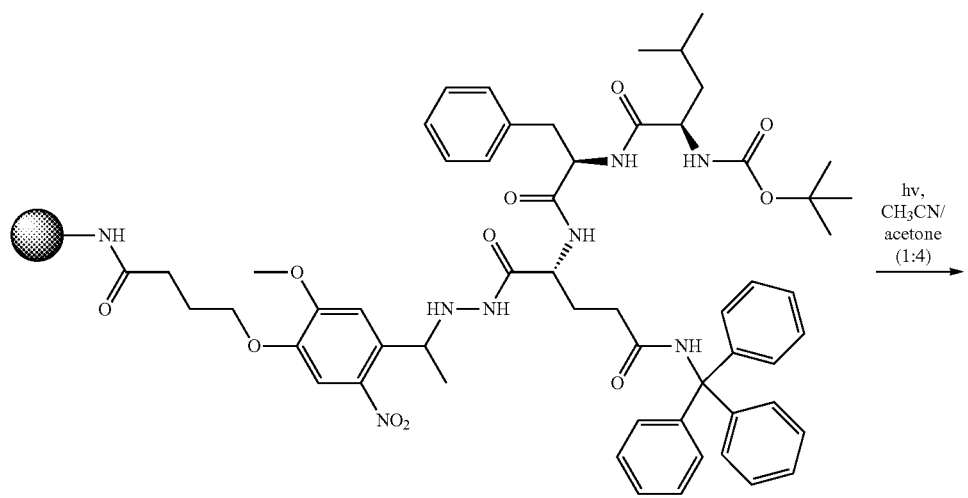
7v -continued
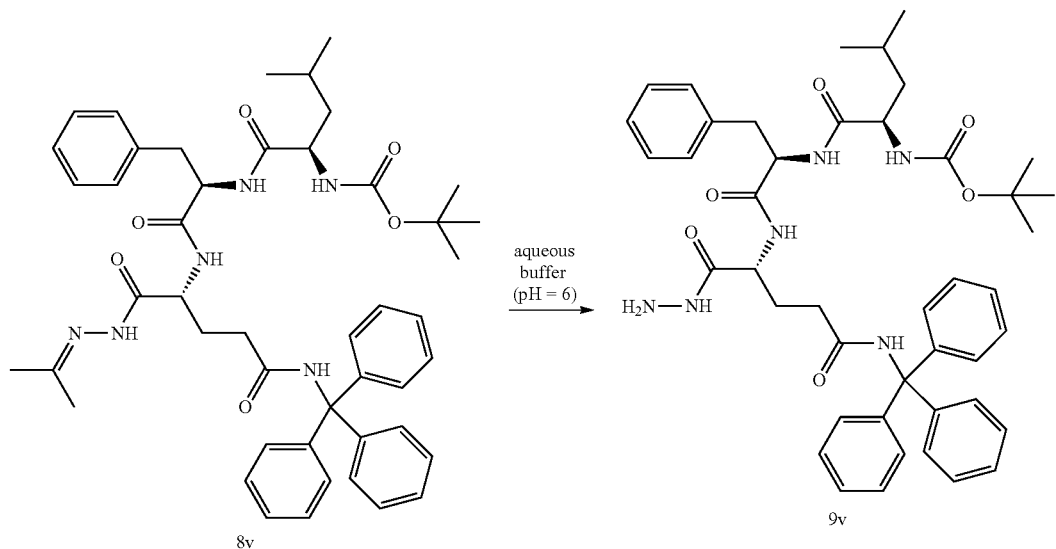
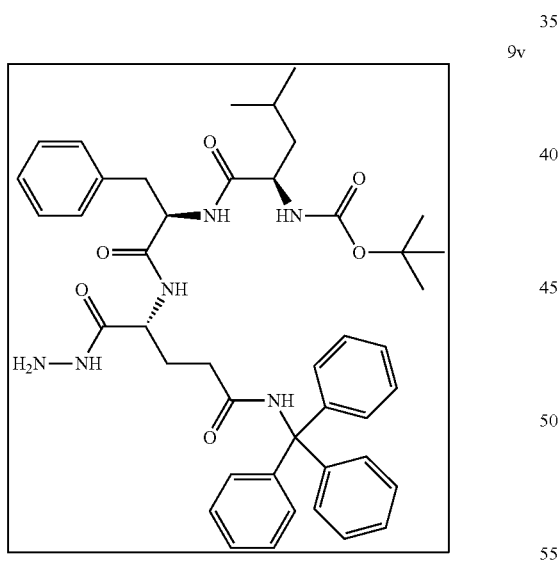
UPLC: Rt=2.31, 2.46 (corresponds to acetone hydrazone 8v)
UPLC-MS (ESI) calculated for $C_{44}H_{55}N_6O_6$ [M+H]$^-$: m/z=763.4, found m/z=763.5.

tert-butyl ((S)-1-(((S)-1-(((R)-3-(tert-butyldisulfa-nyl)-1-hydrazinyl-1-oxopropan-2-yl)amino)-4-methyl-1-oxopentan-2-yl)amino)-1-oxo-3-phenyl-propan-2-yl)carbamate, BocPhe-Leu-Cys(tBu)-NHNH₂ (9w)
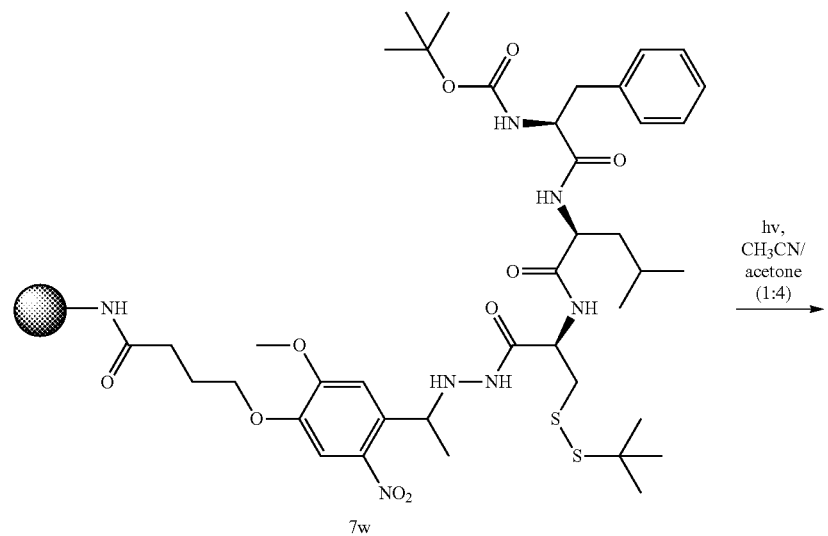
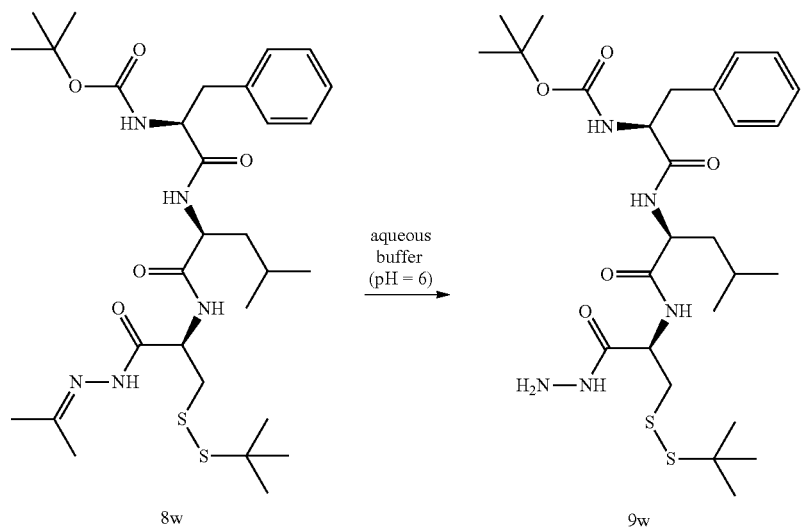

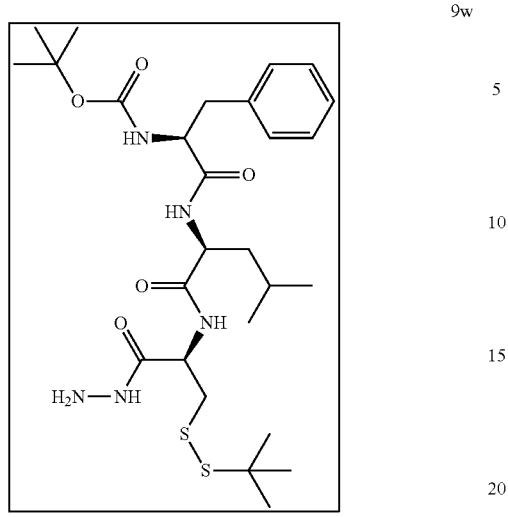
9w
UPLC: Rt=2.07, 2.28 (corresponds to acetone hydrazone 8w)
UPLC-MS (ESI) calculated for $C_{27}H_{46}N_5O_5S_2[M+H]^-$: m/z=584.3, found m/z=584.3.
tert-butyl ((S)-1-(((S)-3-(4-(tert-butoxy)phenyl)-1-(((S)-1-hydrazinyl-1-oxo-5-(3-((2,2,4,6,7-pentamethyl-2,3-dihydrobenzofuran-5-yl)sulfonyl)guanidino)pentan-2-yl)amino)-1-oxopropan-2-yl)amino)-1-oxopropan-2-yl)carbamate, Boc-Ala-Tyr(tBu)-Arg(Pbf)-NHNH$_2$ (9x)
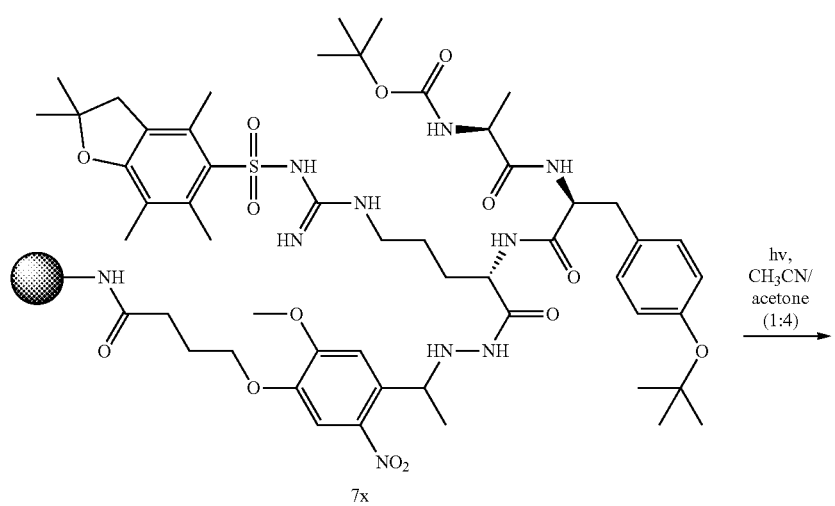
7x
hv, CH$_3$CN/acetone (1:4) →

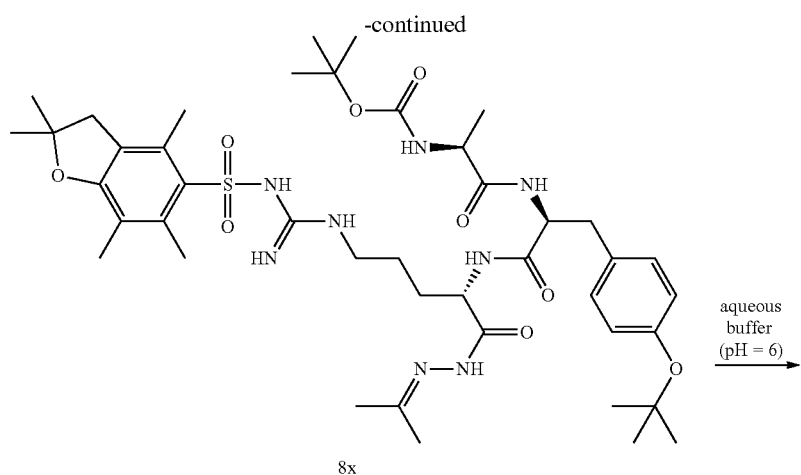
8x
aqueous buffer (pH = 6) →
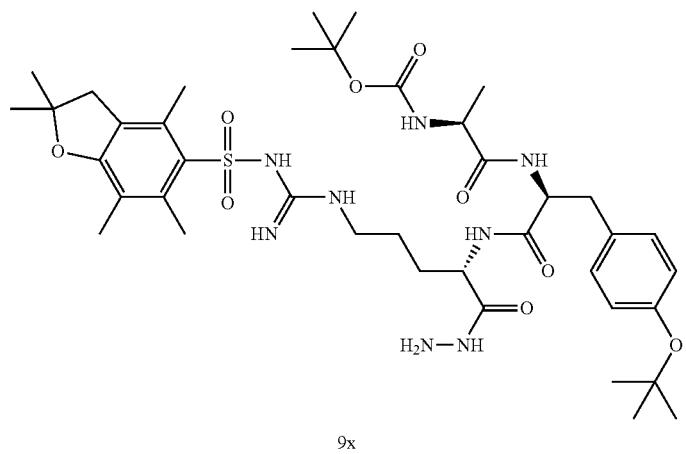
9x
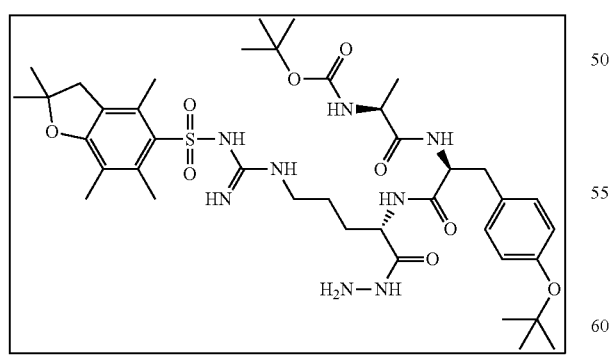
9x
UPLC: Rt=2.01, 2.16 (corresponds to acetone hydrazone 8x)
UPLC-MS (ESI) calculated for $C_{40}H_{63}N_8O_9S$ [M+H]⁻: m/z=831.4, found m/z=831.5.

tert-butyl 4-((6R,9R,12R)-9-benzyl-12-(hydrazinecarbonyl)-6-isopropyl-2,2-dimethyl-4,7,10-trioxo-3-oxa-5,8,11-triazatridecan-13-yl)-1H-imidazole-1-carboxylate; BocVal-Phe-His(Boc)-NHNH₂ (9y)
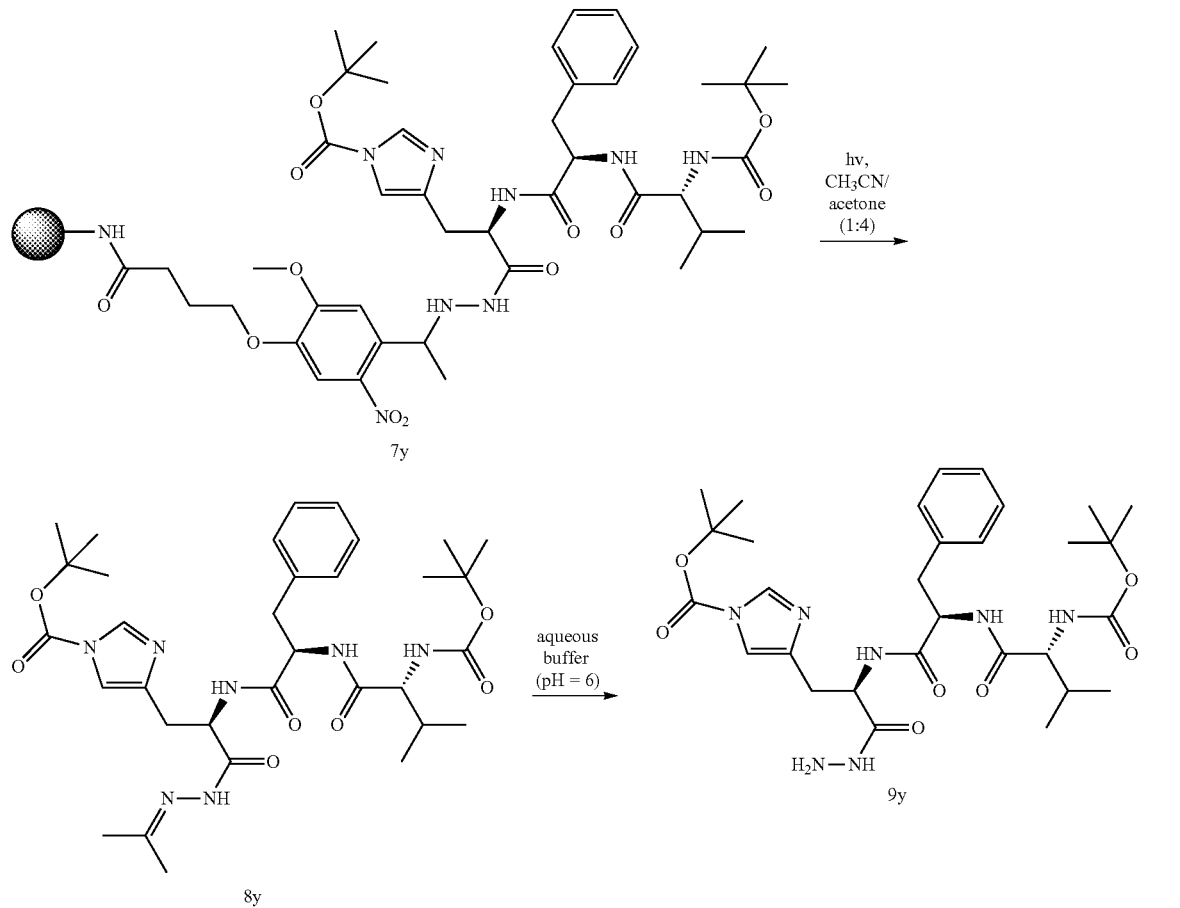
UPLC: Rt=1.76, 1.93 (corresponds to acetone hydrazone 8y)
UPLC-MS (ESI) calculated for $C_{30}H_{46}N_7O_2$ [M+H]⁻: m/z=616.4, found m/z=616.5.
(S)—N-(1-hydrazinyl-3-(1H-imidazol-4-yl)-1-oxopropan-2-yl)-2-naphthamide; Naph-His-NHNH₂ (9z)
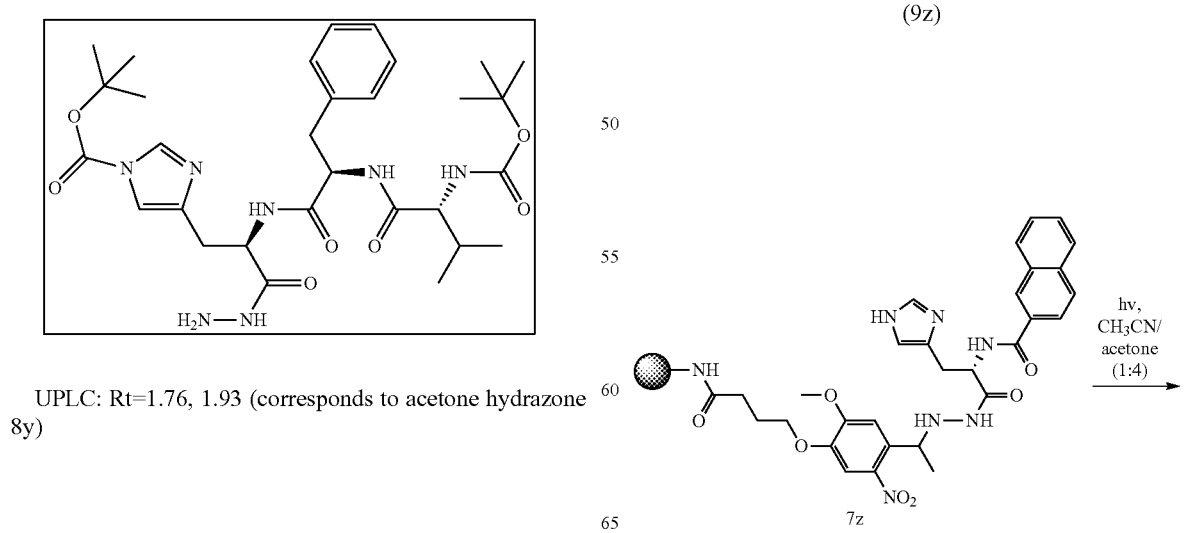

79
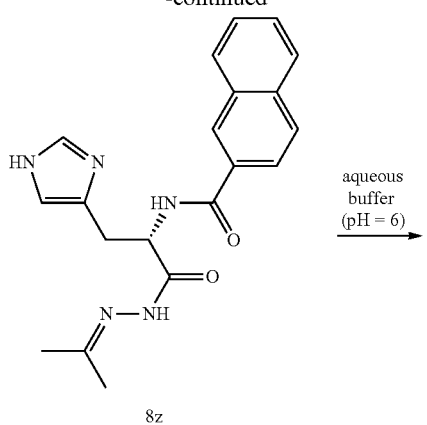
80
(S)-tert-butyl (5-(2-naphthamido)-6-hydrazinyl-6-oxohexyl)carbamate; Napht-Lys(Boc)-NHNH₂ (9aa)
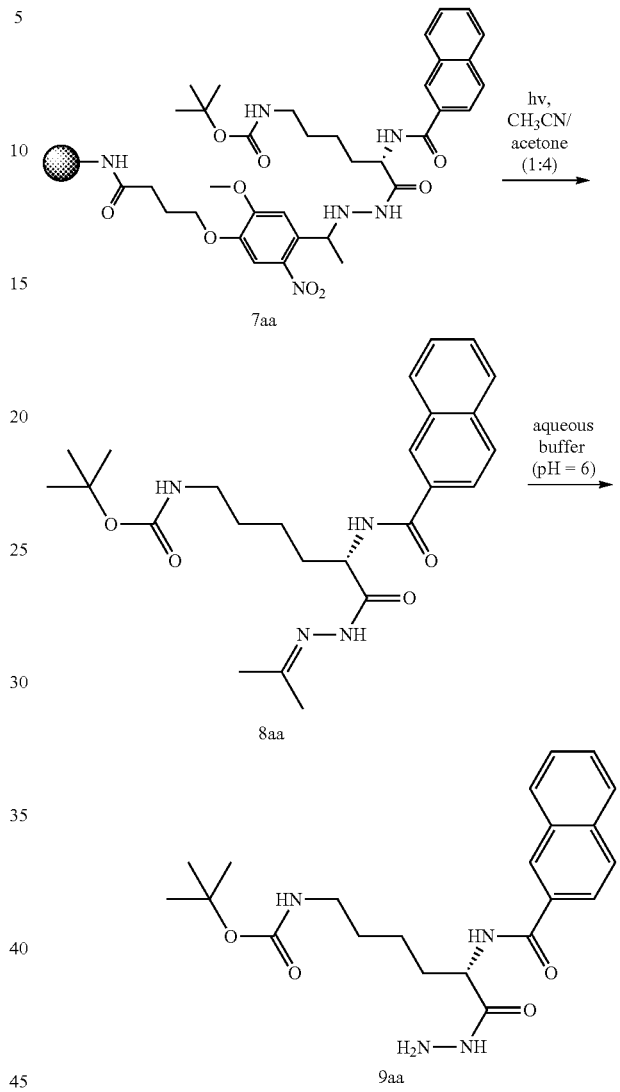
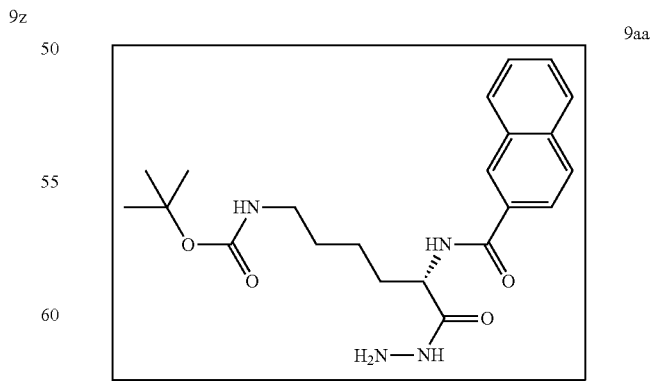
UPLC: Rt=0.75
UPLC-MS (ESI) calculated for $C_{17}H_{18}N_5O_2$ [M+H]⁻: m/z=324.2, found m/z=324.2.
UPLC: Rt=1.55, 1.49 (corresponds to acetone hydrazone 8aa)
UPLC-MS (ESI) calculated for $C_{22}H_{31}N_4O_4$ [M+H]⁻: m/z=415.2, found m/z=415.2.

BocAla-Phe-Lys(Boc)-NHNH₂ (9ab)
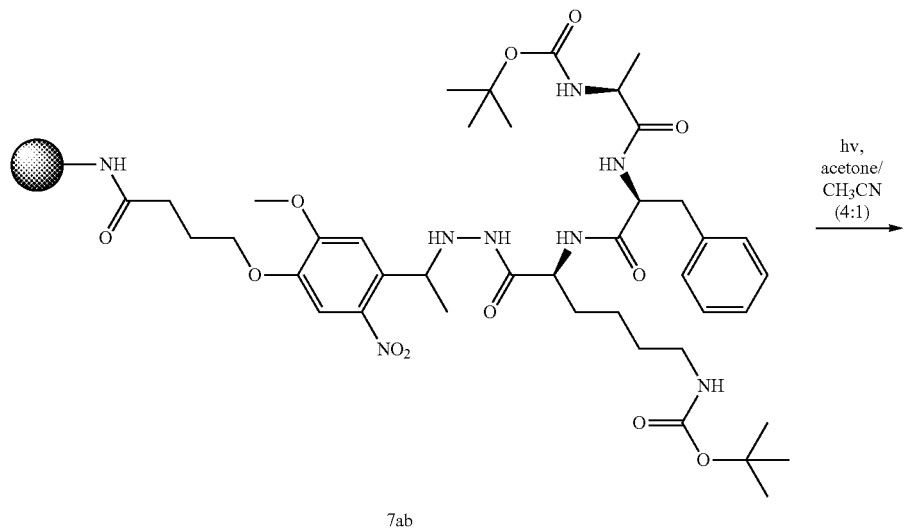
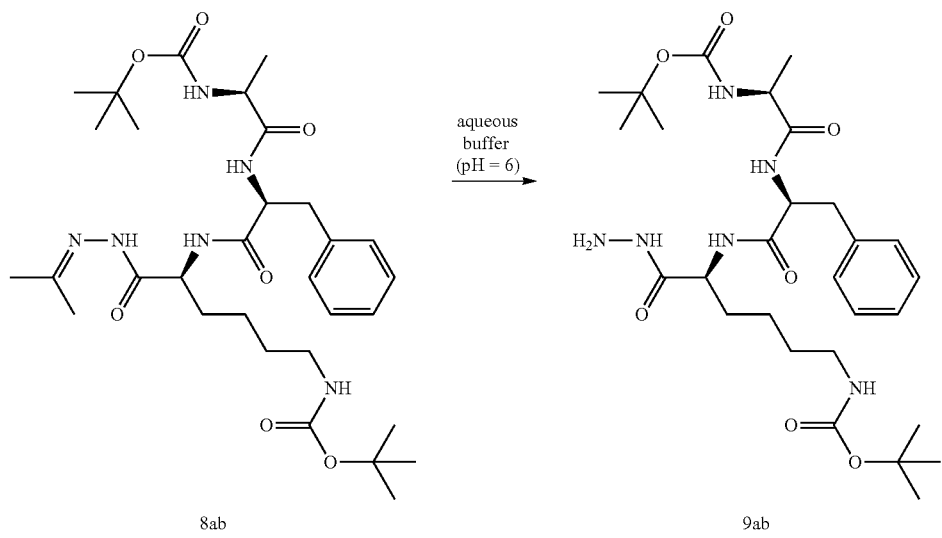

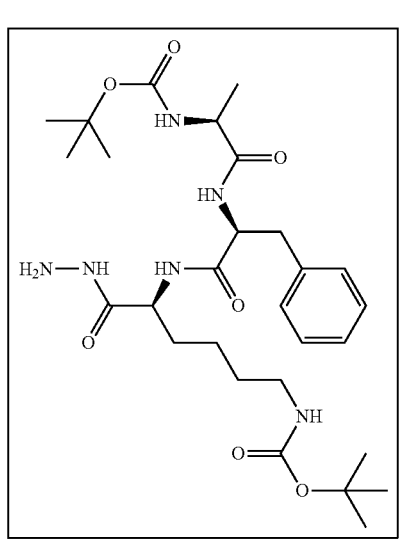
9ab
UPLC: Rt=1.63, 1.83 (corresponds to acetone hydrazone 8ab)
UPLC-MS (ESI) calculated for $C_{28}H_{47}N_6O_7$ [M+H]$^-$: m/z=579.4, found m/z=579.4.
(S)-tert-butyl 3-((R)-2-((tert-butoxycarbonyl)amino)-3-phenylpropanamido)-4-hydrazinyl-4-oxobutanoate; Boc-Phe-Asp(tBu)-NHNH$_2$ (9ac)
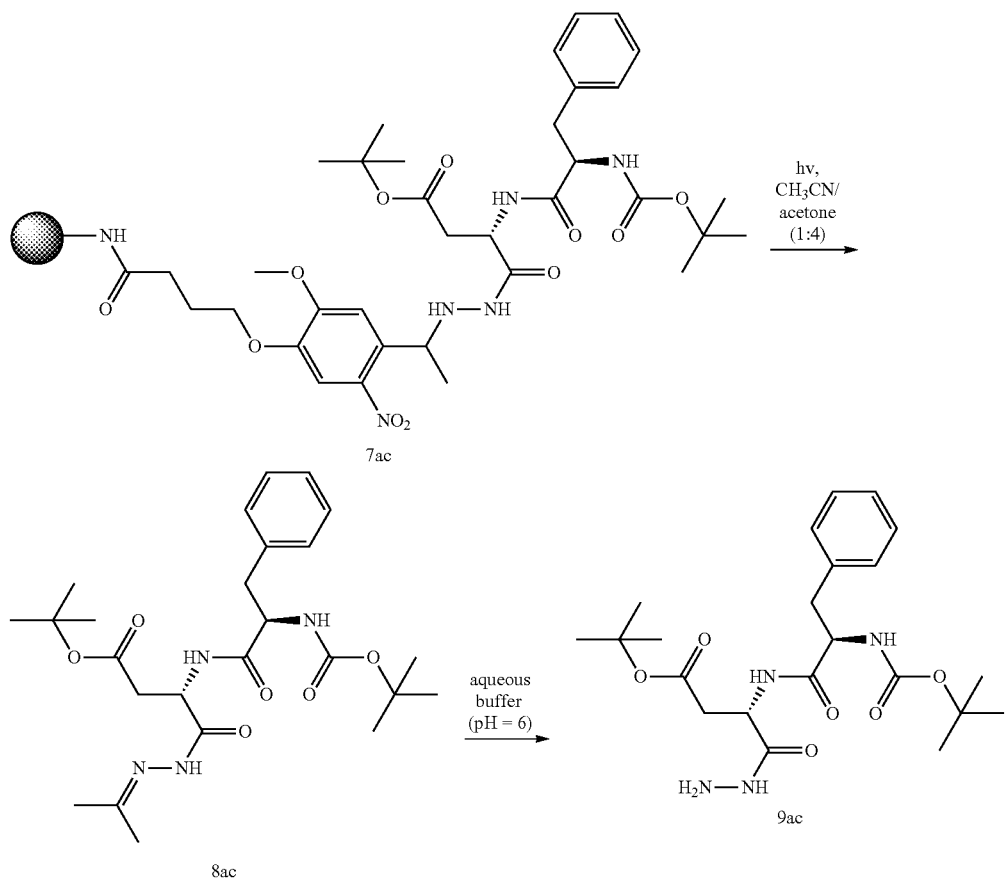

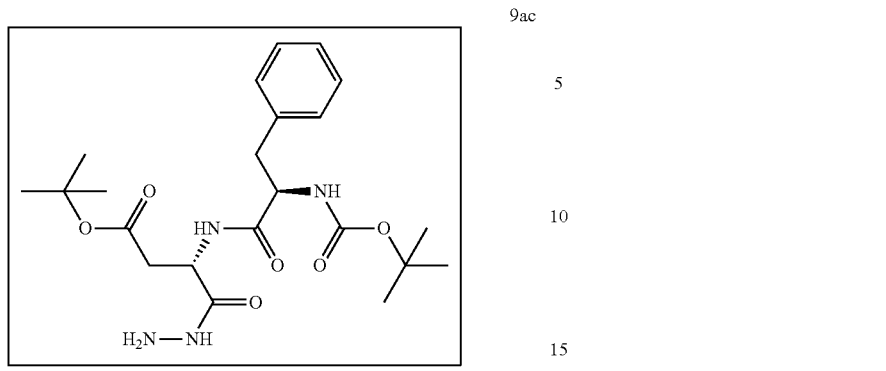
9ac
UPLC: Rt=1.63, 1.83 (corresponds to acetone hydrazone 8ac)
UPLC-MS (ESI) calculated for $C_{22}H_{35}N_4O_6[M+H]^-$: m/z=451.3, found m/z=451.3.
(S)-tert-butyl 2-(((S)-1-(((S)-5-(tert-butoxy)-1-hydrazinyl-1,5-dioxopentan-2-yl)amino)-1-oxo-3-phenylpropan-2-yl)carbamoyl)pyrrolidine-1-carboxylate; BocPro-Phe-Glu(tBu)-NHNH$_2$ (9ad)
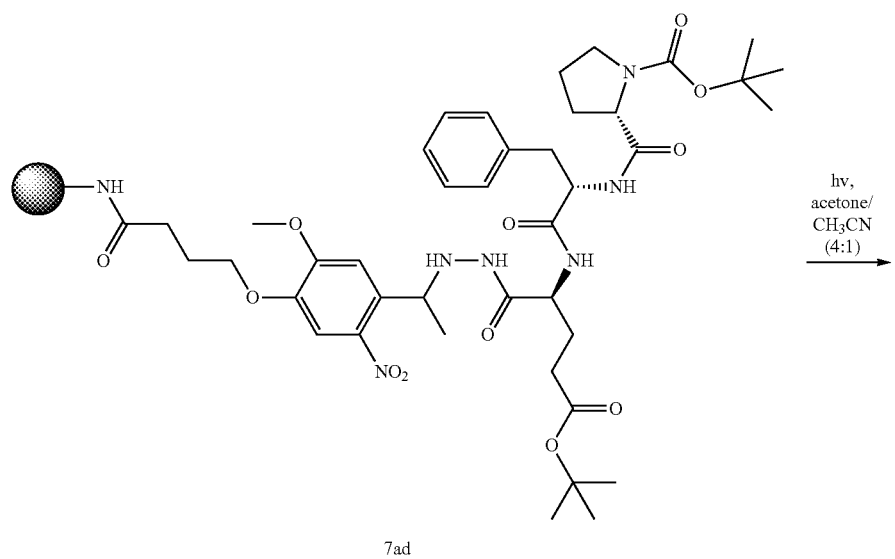
7ad
hv, acetone/ CH$_3$CN (4:1)

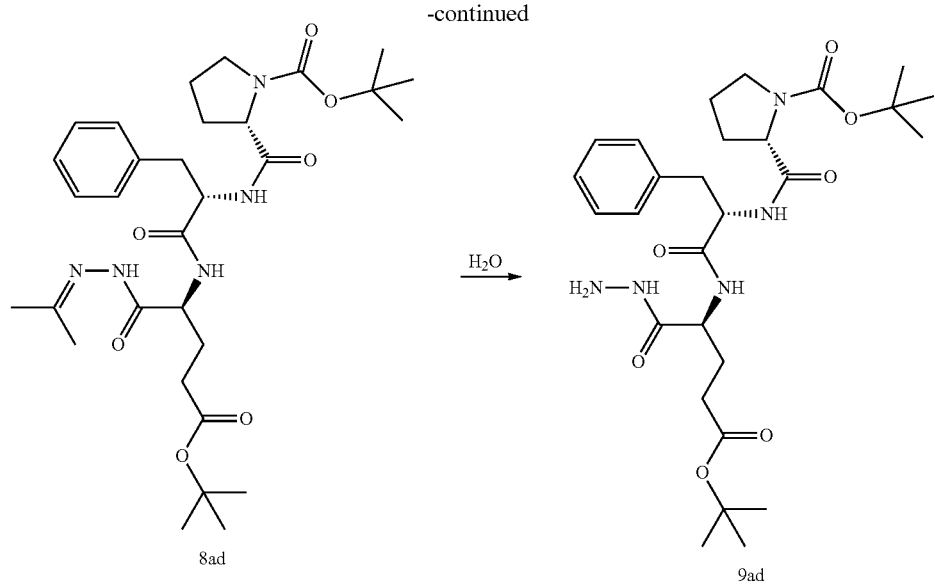

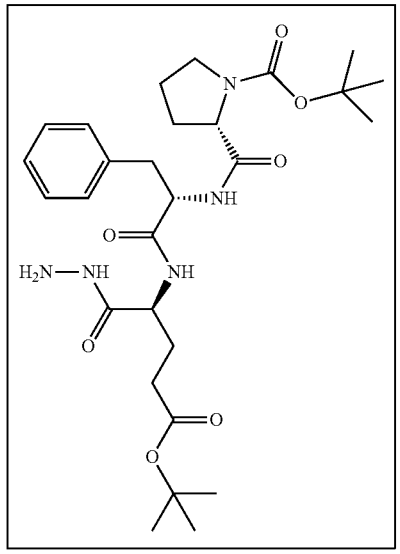

UPLC: Rt=1.76, 1.98 (corresponds to acetone hydrazone 8ad)

UPLC-MS (ESI) calculated for $C_{28}H_{44}N_5O_7$ [M+H]$^-$: m/z=562.7, found m/z=562.5.

Example 4

Synthesis of H-Cys-Lys-Tyr-Met-His-OH (SEQ ID NO: 4) (14)

Starting from an HMBA-functionalized ChemMatrix resin, the linear assembly was performed following the Fmoc-strategy according to the general procedure presented above.

Starting from hydrazine-functionalized ChemMatrix resin 6, the linear assembly was performed following the Fmoc-strategy according to the general procedure presented above.

Example 5

Ligation Experiments

Starting from hydrazine-functionalized ChemMatrix resin 6, the linear assembly of hydrazide-ligation peptide H-Leu-Tyr-Arg-Ala-Tyr-NHNH$_2$ (SEQ ID NO: 2) (13) was performed following the Fmoc-strategy according to the general procedure presented above. Resin sample (50 mg) was immersed in acetone (2 mL) in a 2.5 mL Petri dish with a quartz lid and irradiated from the top with a LED UV-lamp 400W for 2 h. The beads were filtered and washed with acetone. The solvent was removed with a steam of nitrogen and the crude products used directly for ligation experiments.

HPLC of crude H-Leu-Tyr-Arg-Ala-Tyr-NHNH$_2$ (SEQ ID NO: 2) (13)

Ligation with Cysteine:

H-Leu-Tyr-Arg-Ala-Tyr-NHNH$_2$ (SEQ ID NO: 2) (13) (1.73 mg, 2.48 µmol) and H-Cys-OH (0.40 mg, 3.30 umol) were dissolved in 0.82 mL of ligation buffer[a] containing 58 µL internal standard buffer[b]. The reaction mixture was held in a 5 mL glass vial at −10° C. (ice-salt bath). Then, 81 µL of NaNO2[c] (200 mM) was added dropwise, and the reaction mixture was stirred for 20 min at −10° C. After that, 0.81 mL of MPAA (200 mM)[d] was added, and the acidity of the mixed solution was adjusted to pH 7.0 with NaOH (2.0 M) slowly. The reaction mixture was stirred at room temperature overnight. The reaction was monitored by HPLC, and the ligation yield was determined according to the internal standard, BzNH2. Before analysis, the reaction solution was reduced by TCEP (30 mM, pH 7.0).

[a]The ligation buffer: 6.0 M Gn.HCl, 0.2 M Na2HPO4, and the acidity was adjusted to pH 3.0 with NaOH (2.0 M) or concentrated HCl slowly. [b]Internal standard buffer: 9.9 mg BzNH2, 2.0 mL ligation buffer, pH 7.0. [c]Oxidative solution: NaNO2 (41.4 mg, 0.6 mmol) in neat water (3.0 mL). [d]The solution of RSH: MPAA (33.6 mg, 0.2 mmol) in neutral ligation buffer (1 mL).

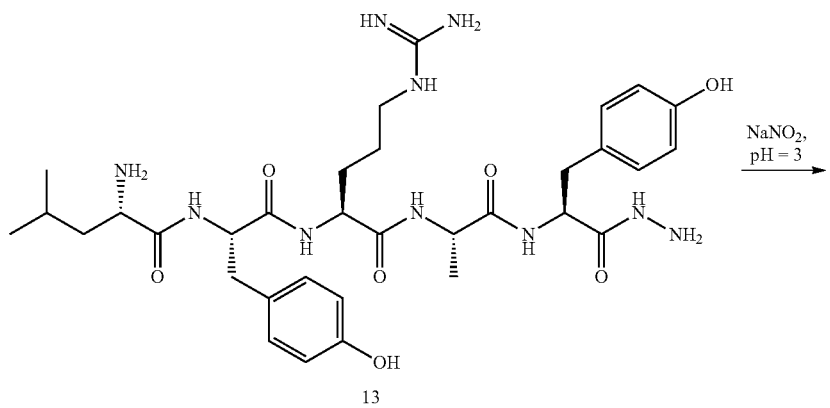

13

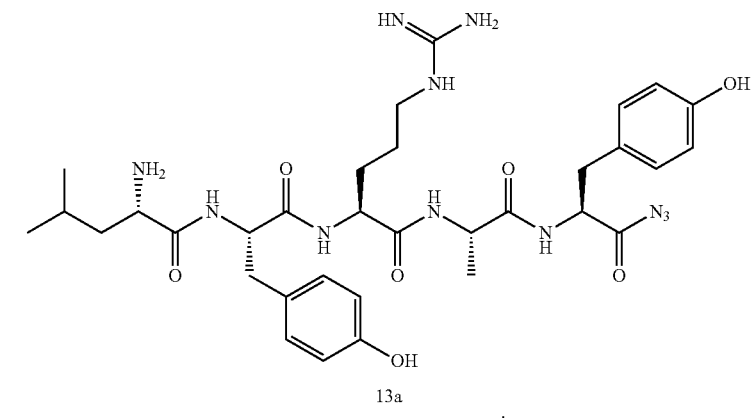

13a

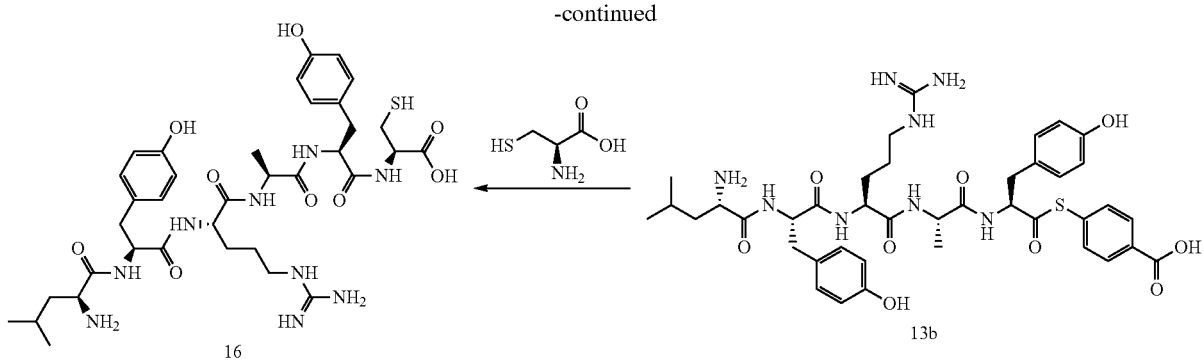

H-Leu-Tyr-Arg-Ala-Tyr-NHNH$_2$ (SEQ ID NO: 2) (13) (1.80 mg, 2.58 μmol) and H-Cys-Lys-Tyr-Met-His-OH (SEQ ID NO: 4) (14) (2.34 mg, 3.43 umol) were dissolved in 0.85 mL of ligation buffer[a] containing 60 μL internal standard buffer.[b] The reaction mixture was held in a 5 mL glass vial at −10° C. (ice-salt bath). Then, 84 μL of NaNO$_2$[c] (200 mM) was added dropwise, and the reaction mixture was stirred for 20 min at −10° C. After that, 0.84 mL of MPAA (200 mM)d was added, and the acidity of the mixed solution was adjusted to pH 7.0 with NaOH (2.0 M) slowly.

The reaction mixture was stirred at room temperature overnight. The reaction was monitored by HPLC, and the ligation yield was determined according to the internal standard, BzNH$_2$. Before analysis, the reaction solution was reduced by TCEP (30 mM, pH 7.0).

[a]The ligation buffer: 6.0 M Gn.HCl, 0.2 M Na$_2$HPO$_4$, and the acidity was adjusted to pH 3.0 with NaOH (2.0 M) or concentrated HCl slowly. [b]Internal standard buffer: 9.9 mg BzNH$_2$, 2.0 mL ligation buffer, pH 7.0. [c]Oxidative solution: NaNO$_2$ (41.4 mg, 0.6 mmol) in neat water (3.0 mL). [d]The solution of RSH: MPAA (33.6 mg, 0.2 mmol) in neutral ligation buffer (1 mL)

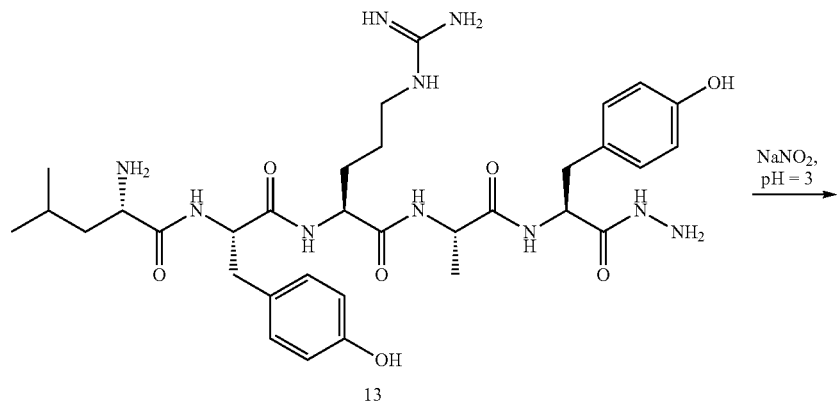

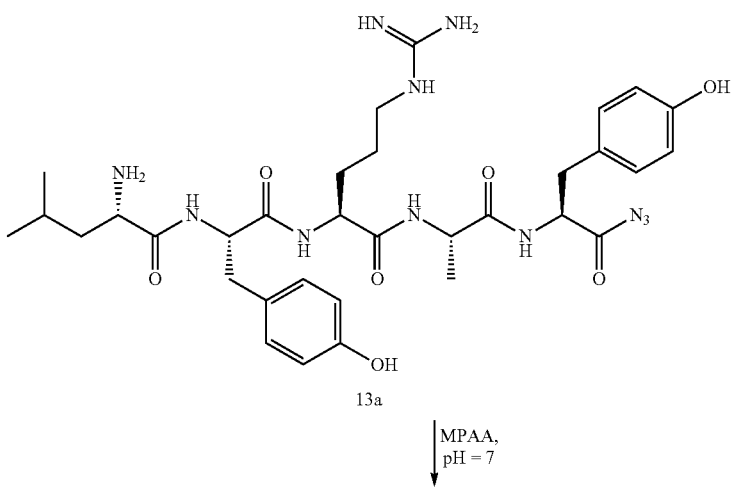

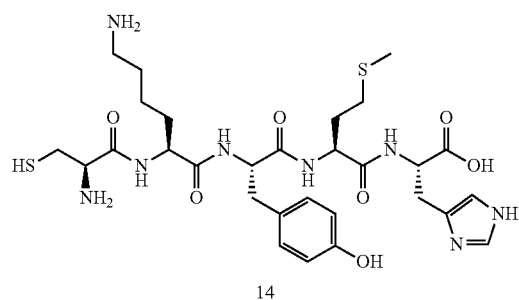

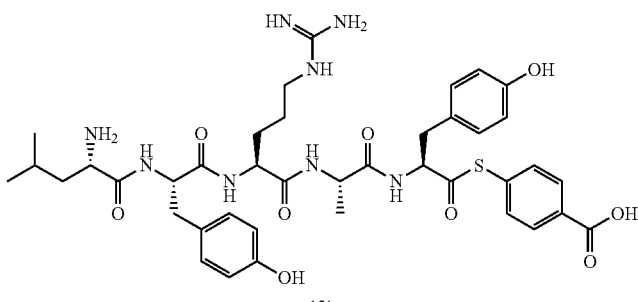

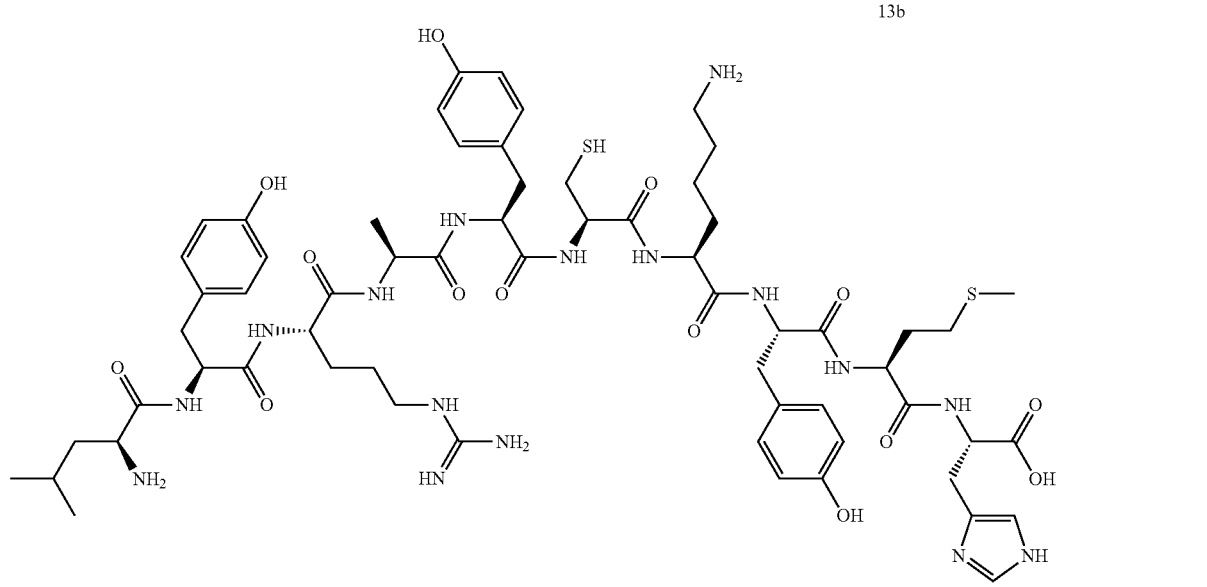

UPLC-MS (ESI) calculated for $C_{62}H_{91}N_{16}O_{14}S_2$ [M+H]$^-$: m/z=1348.6, found m/z=1348.2.

Example 6

Crude RP-HPLC and LC-MS Data for Pyranopyrazoles (12a-12h)

6-amino-3-benzyl-4-(4-methoxy-2,3-dimethylphenyl)-1,4-dihydropyrano[2,3-c]pyrazole-5-carbonitrile (12a)

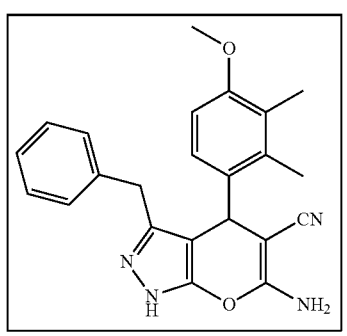 [SMILES: COc1ccc(C2C(C#N)=C(N)Oc3[nH]nc(Cc4ccccc4)c32)c(C)c1C]

UPLC: Rt=1.82, 1.90 (2,4-dihydro tautomer).

UPLC-MS (ESI) calculated for $C_{23}H_{23}N_4O_2$ [M+H]$^-$: m/z=387.2, found m/z=387.5.

6-amino-3-benzyl-4-(3-chlorophenyl)-1,4-dihydropyrano[2,3-c]pyrazole-5-carbonitrile (12b)

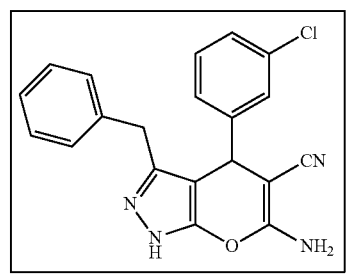 [SMILES: N#CC1=C(N)Oc2[nH]nc(Cc3ccccc3)c2C1c1cccc(Cl)c1]

UPLC: Rt=1.77, 1.84 (2,4-dihydro tautomer).

UPLC-MS (ESI) calculated for $C_{20}H_{16}ClN_4O$ [M+H]$^-$: m/z=363.1, found m/z=363.4.

6-amino-3-benzyl-4-(2,4-dimethylphenyl)-1,4-dihydropyrano[2,3-c]pyrazole-5-carbonitrile (18c)

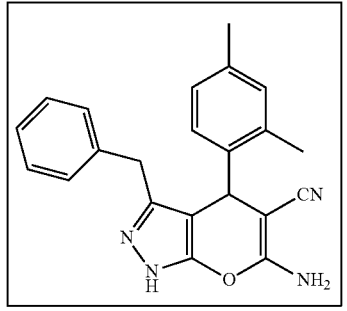 [SMILES: Cc1ccc(C2C(C#N)=C(N)Oc3[nH]nc(Cc4ccccc4)c32)c(C)c1]

UPLC: Rt=1.85, 1.94 (2,4-dihydro tautomer).
UPLC-MS (ESI) calculated for $C_{22}H_{21}N_4O$ [M+H]$^-$: m/z=357.2, found m/z=357.5.

6-amino-3-benzyl-4-(3-nitrophenyl)-1,4-dihydropyrano[2,3-c]pyrazole-5-carbonitrile (12d)

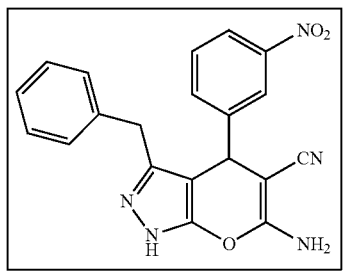 [SMILES: N#CC1=C(N)Oc2[nH]nc(Cc3ccccc3)c2C1c1cccc([N+](=O)[O-])c1]

UPLC: Rt=1.65, 1.68 (2,4-diydro tautomer).
UPLC-MS (ESI) calculated for $C_{20}H_{16}N_5O_3$ [M+H]$^-$: m/z=374.1, found m/z=374.4.

6-amino-3-benzyl-4-(3-fluorophenyl)-1,4-dihydropyrano[2,3-c]pyrazole-5-carbonitrile (12e)

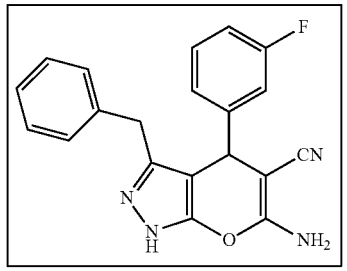 [SMILES: N#CC1=C(N)Oc2[nH]nc(Cc3ccccc3)c2C1c1cccc(F)c1]

UPLC: Rt=1.68, 1.74 (2,4-dihydro tautomer).
UPLC-MS (ESI) calculated for $C_{20}H_{16}FN_4O$ [M+H]$^-$: m/z=347.1, found m/z=347.4.

6-amino-3-benzyl-4-phenyl-1,4-dihydropyrano[2,3-c]pyrazole-5-carbonitrile (12f)

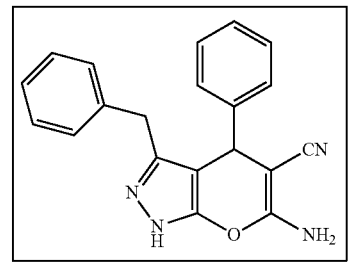 [SMILES: N#CC1=C(N)Oc2[nH]nc(Cc3ccccc3)c2C1c1ccccc1]

UPLC: Rt=1.81, 1.87 (2,4-dihydro tautomer).
UPLC-MS (ESI) calculated for $C_{20}H_{17}N_4O_2$ [M+H]$^-$: m/z=329.1, found m/z=329.3.

6-amino-3-benzyl-4-(p-tolyl)-1,4-dihydropyrano[2,3-c]pyrazole-5-carbonitrile (12g)

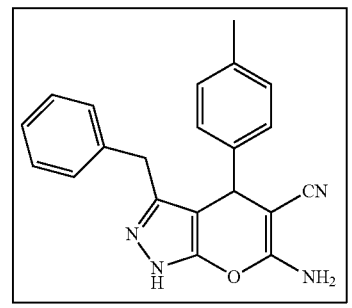 [SMILES: Cc1ccc(C2C(C#N)=C(N)Oc3[nH]nc(Cc4ccccc4)c32)cc1]

UPLC: Rt=1.72, 1.78 (2,4-dihydro tautomer).
UPLC-MS (ESI) calculated for $C_{21}H_{19}N_4O$ [M+H]$^-$: m/z=343.2, found m/z=343.3.

6-amino-4-(4-methoxy-2,3-dimethylphenyl)-3-methyl-1,4-dihydropyrano[2,3-c]pyrazole-5-carbonitrile (12h)

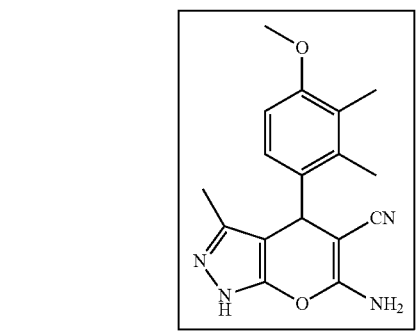 [SMILES: COc1ccc(C2C(C#N)=C(N)Oc3[nH]nc(C)c32)c(C)c1C]

UPLC: Rt=1.47 (2,4-dihydro tautomer seen as a shoulder).
UPLC-MS (ESI) calculated for $C_{17}H_{19}N_4O_2$ [M+H]$^-$: m/z=311.2, found m/z=311.1.

The invention claimed is:

1. A photolabile hydrazine linker having the formula I:

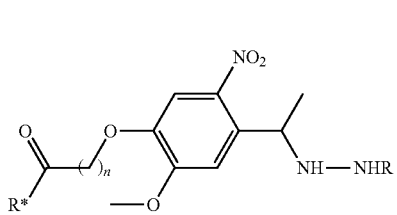

wherein R* is OR', wherein R' is hydrogen, $C_{1-12}$ alkyl, substituted $C_{1-10}$ alkyl, aryl, substituted aryl, heteroaryl, substituted heteroaryl or —($CH_2$—$CH_2$—O)—$_m$;

R is hydrogen or a protection group;

m is an integer from 1-100; and n is an integer from 1 to 10.

2. The photolabile hydrazine linker according to claim 1, wherein R* is OH and R is hydrogen or a protecting group.

3. The photolabile hydrazine linker according to claim 1, wherein n is an integer from 2 to 5, or from 3 to 5 or n is 3.

4. A method for the synthesis of a photolabile hydrazine linker according to claim 1, wherein R* is OH and R is a protecting group, comprising the steps of a) reacting a compound of formula 2:

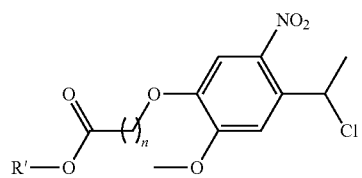

wherein R' is alkyl or substituted alkyl, n is an integer from 1 to 10 with PG-carbazate, where PG is a protecting group to obtain a compound of formula 3:

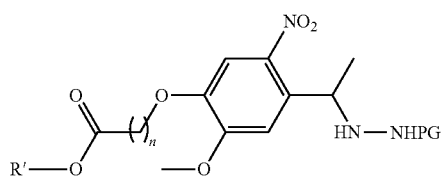

b) hydrolyzing the compound of formula 3 to obtain a compound of formula 4:

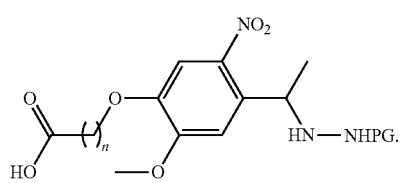

5. A solid phase having a formula of:

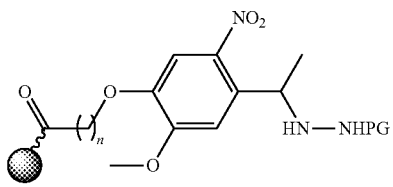

wherein

is a functionalized solid support;

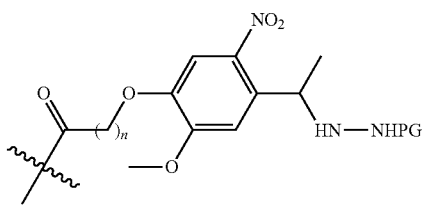

is a photolabile hydrazine linker, wherein n is an integer from 1 to 10; and

PG is a protecting group.

6. The solid phase according to claim 5, wherein the connection between the functionalized solid support and the photolabile hydrazine linker comprises a spacer and/or an orthogonally cleavable linker.

7. The solid phase according to claim 5, wherein

is a solid support functionalized with a group selected from amino, hydroxy, carboxy, acrylo, maleimido, halo (chloro, bromo, iodo), azido, alkynyl, alkenyl, and nitro.

8. The solid phase according to claim 5 having the following formula:

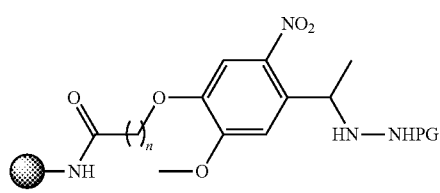

wherein

is an amino-functionalized solid support.

9. The solid phase according to claim 5, wherein PG is a protecting group selected from the group comprising Cbz (Z), multiple substituted methoxy-, nitro-, or chloro Cbz (including Z(4-MeO), Z(2-NO2), Z(4-NO2), Z(2-Cl), Z(3-Cl), Z(2,4-Cl), Z(3,5-OMe)), Ddz, Nvoc, Pz, Tmz, Bic, Bpoc, Azoc, iNoc Bocm Cyoc, Tcboc, Adoc, Adpoc, Iboc, Fmoc, Tsoc, Msc, Nsc, Bspoc, Bsmoc, Mspoc, Aloc, Teoc, Tipseoc, Pipoc, Poc, PTnm, Epoc, Mtr, Pmc, Pbf, Trt, 2-Cl-Trt, Dmt, Tmob, Tfa, Tos, o-Nbs, p-Nbs, dNBS, Bts, Nps, Dde, Nde, Trt, Bzl, Acm.

10. A method for the synthesis of a solid phase, comprising a step of reacting a functionalized solid support with a photolabile hydrazine linker according to claim 1, wherein R* is OH and R is a protecting group.

11. A solid phase having a formula of:

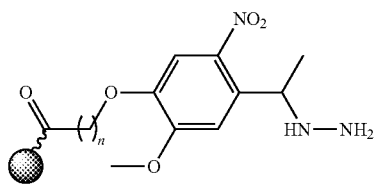

wherein

is a functionalized solid support,

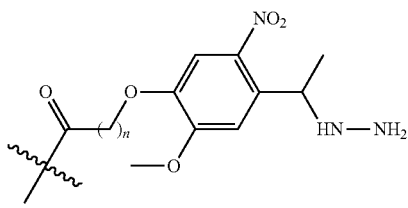

is a photolabile hydrazine linker, wherein n is an integer from 1 to 10; and the connection between the solid support and the photolabile hydrazine linker optionally comprises a spacer and/or an orthogonally cleavable linker.

12. The solid phase according to claim 11 having the formula

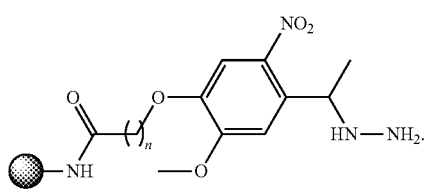

13. A method for the synthesis of a solid phase comprising an immobilized hydrazine-functionalized photolabile linker, comprising the step of removing the protecting group from the solid phase according to claim 5.

14. A method for the solid phase peptide synthesis (SPPS) of peptide hydrazides, comprising the steps of:
  a) Providing a solid phase according to claim 11,
  b) Coupling a first N-protected amino acid moiety to said immobilized hydrazine-functionalized photolabile linker,
  c) Deprotecting said coupled N-protected amino acid moiety,
  d) Coupling a second N-protected amino acid moiety to said immobilized amino acid moiety,
  e) Deprotecting said coupled N-protected amino acid moiety,
  f) repeating said coupling and deprotection steps d and e as many times as necessary to synthesize an immobilized peptide as desired,
  g) cleaving said immobilized peptide from the solid support by irradiation of the photolabile linker to obtain the peptide hydrazide.

15. A method according to claim 14, wherein cleaving in step g) is performed in acetone/$CH_3CN$ to obtain the acetone protected peptide hydrazide, which optionally is deprotected in the presence of water.

16. A method according to claim 14, wherein the amino acid moiety is selected among any natural and synthetic amino acids and derivatives thereof, preferable among the naturally occurring amino acids.

17. A method for the synthesis of oligo- or polypeptides, comprising the steps of:
  a) obtaining a peptide hydrazide or acetone hydrazone protected peptide hydrazide in a method according to claim 14, and
  b) Coupling said peptide hydrazide with a peptide in a ligation reaction to obtain an oligo- or polypeptide.

18. A method for the synthesis of dihydropyrano[2,3-c] pyrazoles of the formula:

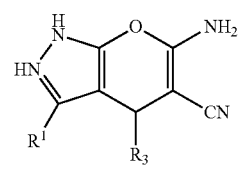

wherein $R_1$ is selected from $C_{1-8}$ alkyl, substituted $C_{1-8}$ alkyl, aryl, substituted aryl, heteroaryl and substituted heteroaryl and $R_3$ is selected from aryl, substituted aryl, heteroaryl and substituted heteroaryl comprising the steps of:
  a) providing a solid phase according to claim 11,
  b) reacting said hydrazine-functionalized photolabile linker with a β-keto ester with the formula:

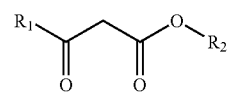

wherein $R_2$ is $C_{1-8}$ alkyl or substituted $C_{1-8}$ alkyl, preferably methyl or ethyl, to obtain an immobilized 1H-pyrazol-5(4H)-one with formula:

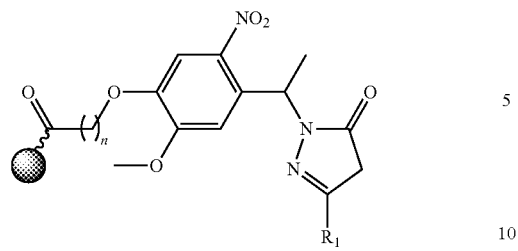

c) reacting the 1H-pyrazol-5(4H)-one with an aldehyde $R_3$—CO, wherein $R_3$ is selected from aryl, substituted aryl, heteroaryl and substituted heteroaryl, in the presence of malononitrile to obtain an immobilized dihydropyrano[2,3-c]pyrazole with the formula:

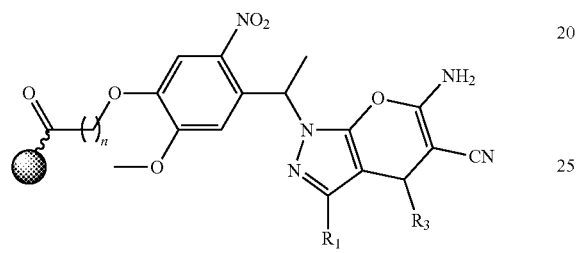

d) cleaving said immobilized peptide from the solid support by irradiation of the photolabile linker to obtain the dihydropyrano[2,3-c]pyrazole.

\* \* \* \* \*